(12) United States Patent
Buchold et al.

(10) Patent No.: US 9,434,763 B2
(45) Date of Patent: Sep. 6, 2016

(54) DERIVATIVES OF PYRIDINONE AS INHIBITORS FOR TISSUE TRANSGLUTAMINASE

(71) Applicant: ZEDIRA GMBH, Darmstadt (DE)

(72) Inventors: Christian Buchold, Bad Vilbel (DE); Uwe Gerlach, Bad Vilbel (DE); Martin Hils, Darmstadt (DE); Ralf Pasternack, Griesheim (DE); Johannes Weber, Darmstadt (DE)

(73) Assignee: ZEDIRA GMBH, Darmstadt (DE)

( * ) Notice: Subject to any disclaimer, the term of this patent is extended or adjusted under 35 U.S.C. 154(b) by 0 days.

(21) Appl. No.: 14/415,374

(22) PCT Filed: Jul. 12, 2013

(86) PCT No.: PCT/EP2013/064789
§ 371 (c)(1),
(2) Date: Jan. 16, 2015

(87) PCT Pub. No.: WO2014/012858
PCT Pub. Date: Jan. 23, 2014

(65) Prior Publication Data
US 2015/0203535 A1    Jul. 23, 2015

Related U.S. Application Data

(60) Provisional application No. 61/741,871, filed on Jul. 30, 2012.

(30) Foreign Application Priority Data

Jul. 17, 2012  (EP) .................................. 12176776

(51) Int. Cl.
*A61K 45/06* (2006.01)
*C07K 5/093* (2006.01)

(Continued)

(52) U.S. Cl.
CPC ............. *C07K 5/1021* (2013.01); *A61K 38/06* (2013.01); *A61K 38/07* (2013.01); *A61K 45/06* (2013.01);
(Continued)

(58) Field of Classification Search
CPC  C07D 213/75; C07D 401/06; C07D 401/12; C07D 405/12; C07D 409/12; C07D 413/12; C07D 417/12; C07D 493/10; C07K 5/0202; C07K 5/081; C07K 5/0819; C07K 5/1002; C07K 5/1021; C07K 5/1024
USPC ........................................... 546/297; 514/349
See application file for complete search history.

(56) References Cited

U.S. PATENT DOCUMENTS

2011/0229568 A1*  9/2011  Oertel ........................... 424/465

FOREIGN PATENT DOCUMENTS

WO    WO 2008/055488    5/2008

OTHER PUBLICATIONS

Warner; J. Med. Chem. 1994,37, 3090-3099.*
Golec; Bioorganic and Medicinal Chemistry Letters 1997, 7, 2181-2186.*

(Continued)

*Primary Examiner* — Noble Jarrell
*Assistant Examiner* — Daniel Carcanague
(74) *Attorney, Agent, or Firm* — Knobbe, Martens, Olson & Bear, LLP

(57) ABSTRACT

The invention relates to pyridinone derivatives of general formula (I) as inhibitors of tissue transglutaminase, to methods for producing the pyridinone derivatives, to pharmaceutical compositions containing said pyridinone derivatives and to their use for the prophylaxis and treatment of diseases associated with tissue transglutaminase.

13 Claims, 2 Drawing Sheets

(51) Int. Cl.

| | | |
|---|---|---|
| *A61K 38/07* | (2006.01) | |
| *C07K 1/06* | (2006.01) | |
| *C07K 5/113* | (2006.01) | |
| *A61K 38/06* | (2006.01) | |
| *C07K 5/10* | (2006.01) | |
| *C07D 213/75* | (2006.01) | |
| *C07D 401/12* | (2006.01) | |
| *C07D 405/12* | (2006.01) | |
| *C07D 409/12* | (2006.01) | |
| *C07D 413/12* | (2006.01) | |
| *C07D 417/12* | (2006.01) | |
| *C07D 493/10* | (2006.01) | |
| *C07D 401/06* | (2006.01) | |
| *C07K 5/02* | (2006.01) | |
| *C07K 5/083* | (2006.01) | |
| *C07K 5/117* | (2006.01) | |

(52) U.S. Cl.
CPC ........... *C07D 213/75* (2013.01); *C07D 401/06* (2013.01); *C07D 401/12* (2013.01); *C07D 405/12* (2013.01); *C07D 409/12* (2013.01); *C07D 413/12* (2013.01); *C07D 417/12* (2013.01); *C07D 493/10* (2013.01); *C07K 1/068* (2013.01); *C07K 5/0202* (2013.01); *C07K 5/081* (2013.01); *C07K 5/0819* (2013.01); *C07K 5/1002* (2013.01); *C07K 5/1024* (2013.01)

(56) References Cited

OTHER PUBLICATIONS

Willoughby; Bioorganic and Medicinal Chemistry Letters 2002, 12, 2197-2200.*
Schaertl; Journal of Biomolecular Screening 2010, 15, 478 487.*
Bannwarth; J. Med. Chem., 2006, 49, 4657-4664.*
Paris; Tetrahedron Letters 1999, 40, 5179-5182.*
Watts; J. Med. Chem. 2006, 49, 7493-7501.*
Rauhavirta; J. Clin. Immunol. 2013, 33, 134-142.*
Selimoglu; J. Clin. Gastroenterol. 2010, 44, 4-8.*
International Search Report for PCT Application No. PCT/EP2013/064789, filed Dec. 7, 2013 in 10 pages.
Choi, Kiang et al., "Chemistry and Biology of Dihydroisoxazole Derivatives: Selective Inhibitors of Human Transglutaminase 2," Chemistry & Biology, vol. 12, Issue 4, 2005, pp. 469-475.
Dafik, Laila et al., "Dihydroisoxazole Analogs for Labeling and Visualization of Catalytically Active Transglutaminase 2," Chemistry & Biology, vol. 18, dated Jan. 28, 2011, pp. 58-66.
Levitzki, Alexander et al., "Evidence for Participation of Transglutaminase in Receptor-Mediated Endocytosis," Proceedings of the National Academy of Sciences U S A., vol. 77, No. 5, May 1980, pp. 2706-2710.
Watts, R. Edward et al., Abstract of "Structure-Activity Relationship Analysis of the Selective Inhibition of Transglutaminase 2 by Dihydroisoxazoles," J. Med. Chem., 2006, vol. 49, No. 25, pp. 7493-7501.

* cited by examiner

DERIVATIVES OF PYRIDINONE AS INHIBITORS FOR TISSUE TRANSGLUTAMINASE

The invention relates to pyridinone derivatives as inhibitors of tissue transglutaminase, methods for synthesis of pyridinone derivatives, pharmaceutical compositions containing these pyridinone derivatives and to their use for the prophylaxis and treatment of diseases associated with tissue transglutaminase.

Transglutaminases are part of the class of transferases and according to EC nomenclature they are correctly designated as "protein-glutamine: amine γ-glutamyl transferases" and the EC number EC 2.3.2.13. has been assigned to them. They link the ε-amino group of the amino acid lysine and the γ-glutamyl group of the amino acid glutamine forming an isopeptide bond while ammonia is released.

Additionally, transglutaminases play an important role in many therapeutic areas such as the cardiovascular field (thrombosis), autoimmune diseases (coeliac disease, Duhring-Brocq-disease), neurodegenerative diseases (Alzheimer's disease, Parkinson's disease, Huntington's disease), dermatological diseases (ichthyosis, psoriasis, acne) as well as in wound healing and inflammatory diseases (tissue fibrosis) (J. M. Wodzinska, Mini-Reviews in medical chemistry, 2005, 5, 279-292).

Coeliac disease, a gluten intolerance, however, is one of the most important indications. Coeliac disease is characterized by a chronic inflammation of the mucosa of the small intestine. In patients concerned, the intestine epithelium is successively destroyed after ingestion of gluten-containing food resulting in reduced absorption of nutrients which again has massive impact on the patients concerned and is for example associated with symptoms such as loss of weight, anemia, diarrhea, nausea, loss of appetite and fatigue. Due to these findings, there is a large demand for the development of a medicament for the treatment of coeliac disease as well as of other diseases associated with tissue transglutaminase. The tissue transglutaminase is a central element during pathogenesis. The endogenous enzyme catalyses the deamidation of gluten/gliadine in the small intestinal mucosa and thus highly increases the inflammatory reaction. Therefore inhibitors of the tissue transglutaminase are suitable to be used as active agents for medication.

The present invention solves the problem to provide new inhibitors of tissue transglutaminases, pharmaceutical formulations containing said inhibitors and methods for the synthesis of said inhibitors. Furthermore, new uses for said inhibitors are indicated.

Said objective is realized by the technical teaching of the independent claims. Further advantageous embodiments, aspects and details of the invention result from the dependent claims, the description and the examples.

Surprisingly, it has been found that pyridinone derivatives having at least one acceptor-substituted double bond and further having a pyridinone fragment in molecularly proximity to the acceptor-substituted double bond are particularly good inhibitors of the tissue transglutaminase, which is also called transglutaminase 2 or TG2. Herein these terms are used synonymous. Preferably, such acceptor-substituted double bonds are Michael systems (MS) from a carbonyl function ($C=O$) or a sulfonyl function ($SO_2$) and a carbon-carbon double bond ($C=C$) conjugated therewith, consequently a Michael acceptor system of the $C=C-C=O$ or $C=C-SO_2$ type. Probably said pyridinone derivatives of the present invention are suicide inhibitors binding irreversibly to the transglutaminases.

Thus, the present invention relates to compounds of the general formula (I):

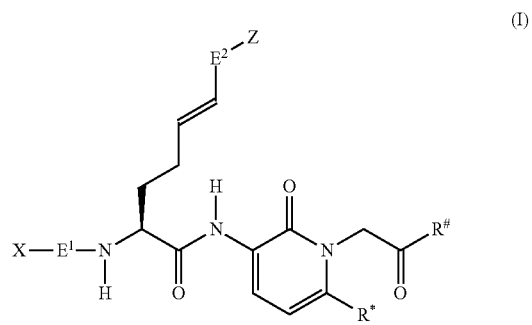

wherein $E^1$, $E^2$ represent independently of each other —CO— or —$SO_2$—,

R* represents one of the following rests —H, —$CH_3$, —$C_2H_5$, —$C_3H_7$, —$CH(CH_3)_2$, or —$C_4H_9$, R# represents one of the following rests —NYY', —OH, —OY, —NH—$CH_2$—COOH, —NH—$CH(CH_3)$—COOH, —NH—$CH(CH_2CH_2SCH_3)$—COOH, —NH—CH($CH_2OH$)—COOH, —NH—$CH(CH_2SH)$—COOH, —NH—$CH(CH_2CONH_2)$—COOH, —NH—CH($CH_2CH_2CONH_2$)—COOH, —NH—$CH(CH_2CH(CH_3)_2)$—$CH_2COOH$, —NH—$CH(CH_2Ph)$-COOH, —NH—CH($CH_2COOH$)—COOH, —NH—$CH(CH_2CH_2COOH)$—COOH, —NH—$CH(COOH)$—$CH(CH_3)_2$, —NH—CH(COOH)—$CH_2CH(CH_3)_2$, —NH—$CH_2$—COOY', —NH—$CH(CH_3)$—COOY', —NH—CH($CH_2CH_2SCH_3$)—COOY', —NH—$CH(CH_2OH)$—COOY', —NH—$CH(CH_2SH)$—COOY', —NH—CH($CH_2CONH_2$)—COOY', —NH—$CH(CH_2CH_2CONH_2)$—COOY', —NH—$CH(CH_2CH(CH_3)_2)$—$CH_2COOY'$, —NH—$CH(CH_2Ph)$-COOY', —NH—$CH(CH_2COOH)$—COOY', —NH—$CH(CH_2COOY')$—COOH, —NH—CH($CH_2COOY$)—COOY', —NH—$CH(CH_2CH_2COOY)$—COOY', —NH—$CH(COOH)$—$CH(CH_3)_2$, —NH—CH(COOH)—$CH_2CH(CH_3)_2$

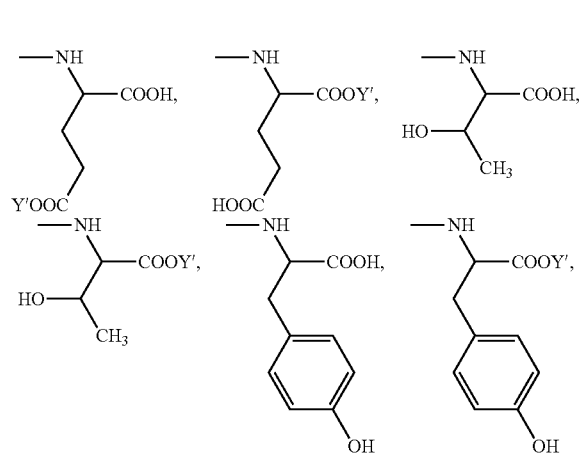

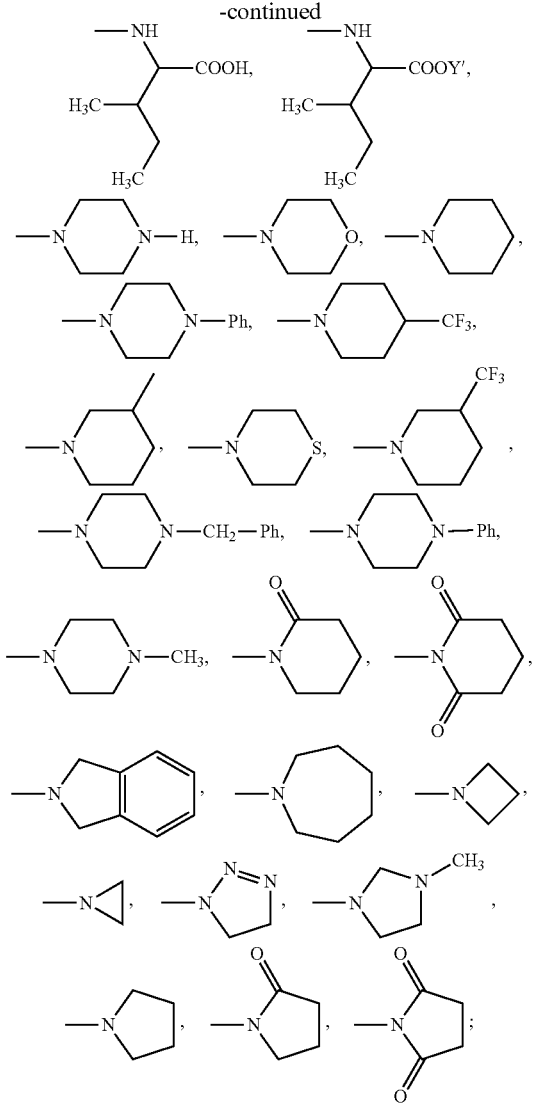

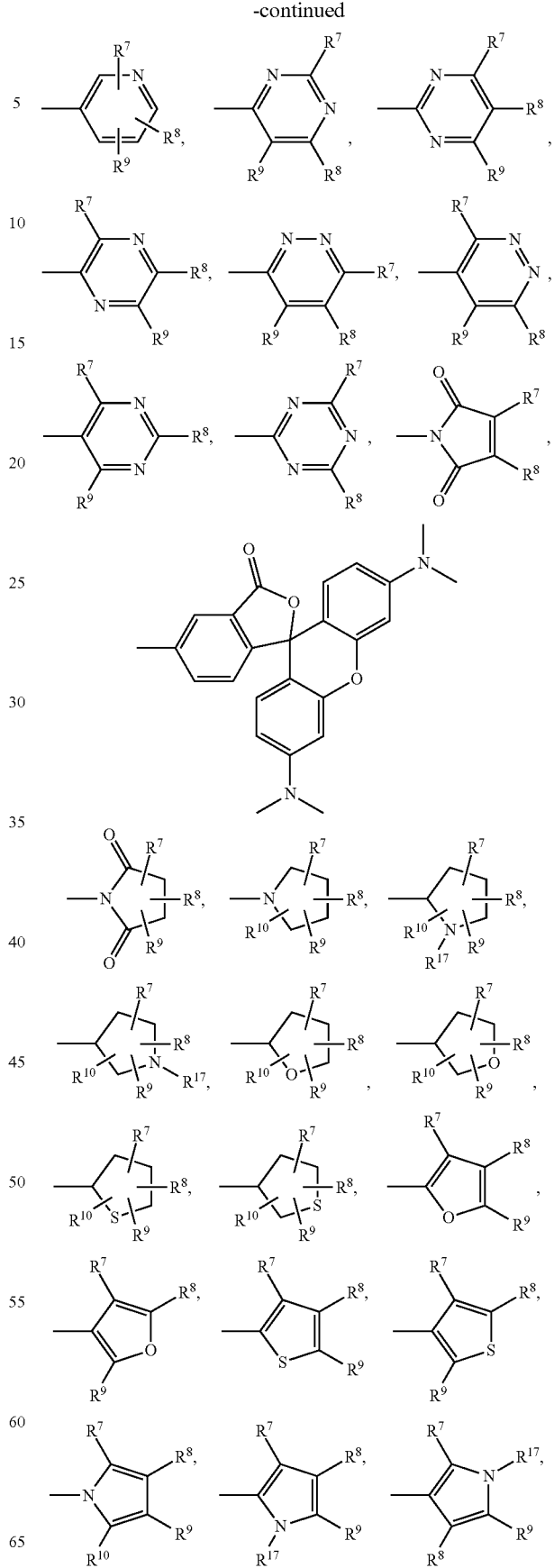

Y represents one of the following rests:
—CH$_2$R$^1$, —CHR$^1$—CH$_2$R$^2$, —CHR$^1$—CHR$^2$—CH$_2$R$^3$, —CHR$^1$—CHR$^2$—CHR$^3$—CH$_2$R$^4$, —CHR$^1$—CHR$^2$—CHR$^3$—CHR$^4$—CH$_2$R$^5$, —CHR$^1$—CHR$^2$—CHR$^3$—CHR$^4$—CHR$^5$—CH$_2$R$^6$ Y', R$^{17}$ to R$^{20}$ are selected independently of each other from:
—H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$ and —C$_2$H$_4$—CH(CH$_3$)$_2$, X represents: —CR$^7$R$^8$R$^9$, —CH$_2$R$^7$, —CHR$^7$—CH$_2$R$^8$, —O—CH$_2$R$^7$, —O—CR$^7$R$^8$R$^9$, —O—CHR$^7$—CH$_2$R$^8$,

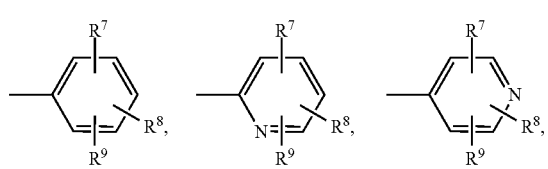

-continued
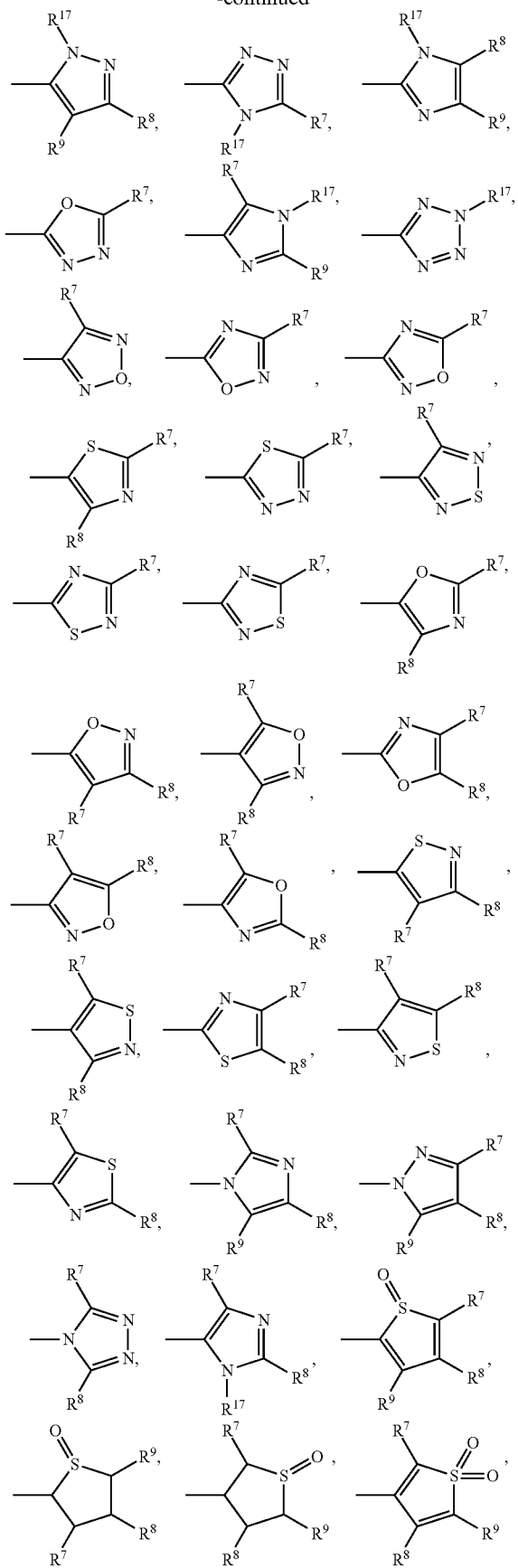
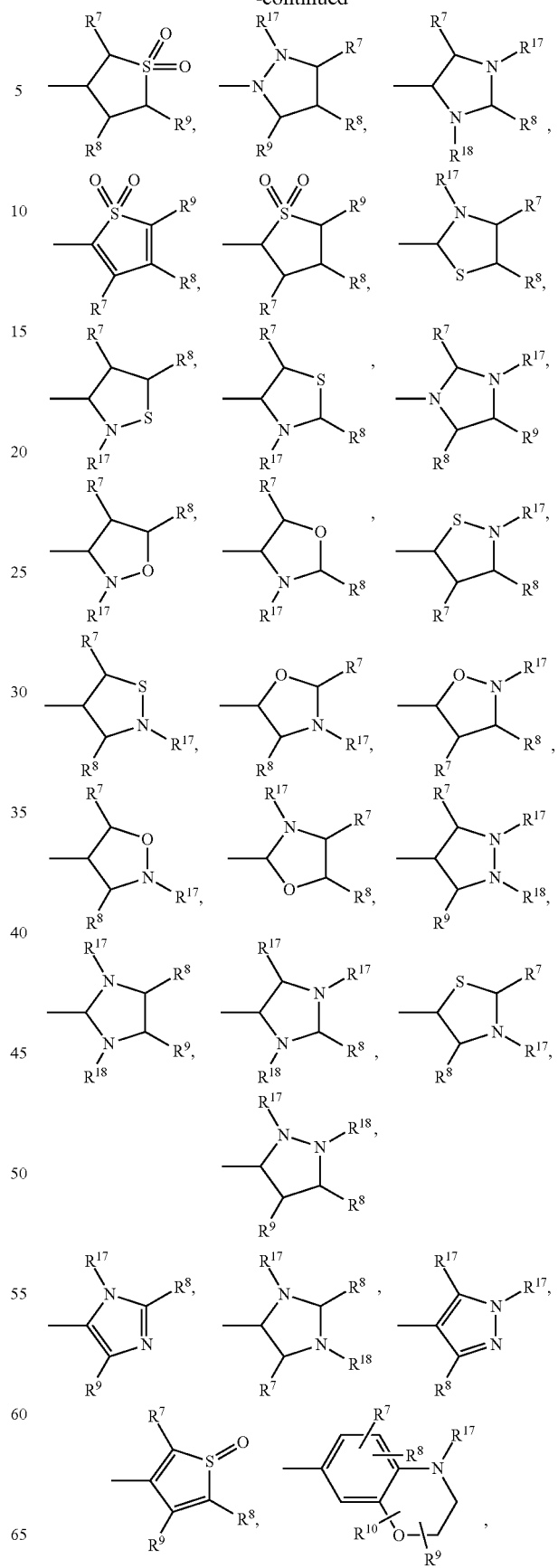

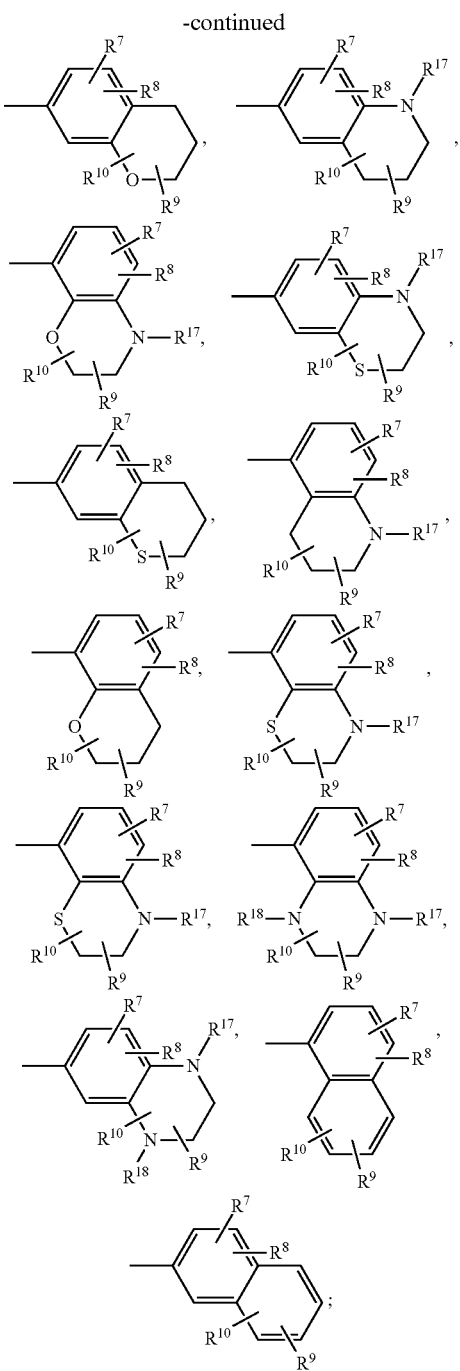

Z represents: —CH$_3$, —C$_2$H$_5$, —C$_3$H$_7$, —CH(CH$_3$)$_2$, —C$_4$H$_9$, -Ph, —CH$_2$-Ph, —OCH$_3$, —OC$_2$H$_5$, —OC$_3$H$_7$, —OCH(CH$_3$)$_2$, —OC$_4$H$_9$, —OPh, —OCH$_2$-Ph, —OCH═CH$_2$ or —OCH$_2$—CH═CH$_2$, R$^1$ to R$^{10}$ represent independently of each other the following groups: —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OCPh$_3$, —SH, —NO$_2$, —F, —Cl, —Br, —I, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NHCOCH$_3$, —NHCOC$_2$H$_5$, —NHCOC$_3$H$_7$, —NHCO-cyclo-C$_3$H$_5$, —NHCO—CH(CH$_3$)$_2$, —NHCO—C(CH$_3$)$_3$, —NHCO—OCH$_3$, —NHCO—OC$_2$H$_5$, —NHCO—OC$_3$H$_7$, —NHCO—O-cyclo-C$_3$H$_5$, —NHCO—OCH(CH$_3$)$_2$, —NHCO—OC(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SOC$_3$H$_7$, —SO-cyclo-C$_3$H$_5$, —SOCH(CH$_3$)$_2$, —SOC(CH$_3$)$_3$, —SO$_2$CH$_3$, —SO$_2$C$_2$H$_5$, —SO$_2$C$_3$H$_7$, —SO$_2$-cyclo-C$_3$H$_5$, —SO$_2$CH(CH$_3$)$_2$, —SO$_2$C(CH$_3$)$_3$, —SO$_3$H, —SO$_3$CH$_3$, —SO$_3$C$_2$H$_5$, —SO$_3$C$_3$H$_7$, —SO$_3$-cyclo-C$_3$H$_5$, —SO$_3$CH(CH$_3$)$_2$, —SO$_3$C(CH$_3$)$_3$, —SO$_2$NH$_2$, —OCF$_3$, —OC$_2$F$_5$, —O—COOCH$_3$, —O—COOC$_2$H$_5$, —O—COOC$_3$H$_7$, —O—COO-cyclo-C$_3$H$_5$, —O—COOCH(CH$_3$)$_2$, —O—COOC(CH$_3$)$_3$, —NH—CO—NH$_2$, —NH—CO—NHCH$_3$, —NH—CO—NHC$_2$H$_5$, —NH—CO—NHC$_3$H$_7$, —NH—CO—NH-cyclo-C$_3$H$_5$, —NH—CO—NH[CH(CH$_3$)$_2$], —NH—CO—NH[C(CH$_3$)$_3$], —NH—CO—N(CH$_3$)$_2$, —NH—CO—N(C$_2$H$_5$)$_2$, —NH—CO—N(C$_3$H$_7$)$_2$, —NH—CO—N(cyclo-C$_3$H$_5$)$_2$, —NH—CO—N[CH(CH$_3$)$_2$]$_2$, —NH—CO—N[C(CH$_3$)$_3$]$_2$, —NH—CS—NH$_2$, —NH—CS—NHCH$_3$, —NH—CS—NHC$_2$H$_5$, —NH—CS—NHC$_3$H$_7$, —NH—CS—NH-cyclo-C$_3$H$_5$, —NH—CS—NH[CH(CH$_3$)$_2$], —NH—CS—NH[C(CH$_3$)$_3$], —NH—CS—N(CH$_3$)$_2$, —NH—CS—N(C$_2$H$_5$)$_2$, —NH—CS—N(C$_3$H$_7$)$_2$, —NH—CS—N(cyclo-C$_3$H$_5$)$_2$, —NH—CS—N[CH(CH$_3$)$_2$]$_2$, —NH—CS—N[C(CH$_3$)$_3$]$_2$, —NH$_2$*HOOCCF$_3$, —CH$_2$F, —CF$_2$Cl, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, cyclo-C$_3$H$_5$, cyclo-C$_4$H$_7$, cyclo-C$_5$H$_9$, cyclo-C$_6$H$_{11}$, cyclo-C$_7$H$_{13}$, cyclo-C$_8$H$_{15}$, -Ph, —CH$_2$-Ph, —CPh$_3$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH═CH$_2$, —CH$_2$—CH═CH$_2$, —C(CH$_3$)═CH$_2$, —CH═CH—CH$_3$, —C$_2$H$_4$—CH═CH$_2$, —C$_7$H$_{15}$, —CH$_2$—CH═CH—CH$_3$, —CH═CH—C$_2$H$_5$, —CH$_2$—C(CH$_3$)═CH$_2$, —CH(CH$_3$)—CH═CH, —CH═C(CH$_3$)$_2$, —C(CH$_3$)═CH—CH$_3$, —CH═CH—CH═CH$_2$, —C$_3$H$_6$—CH═CH$_2$, —C$_2$H$_4$—CH═CH—CH$_3$, —CH$_2$—CH═CH—C$_2$H$_5$, —CH═CH—C$_3$H$_7$, —CH$_2$—CH═CH—CH═CH$_2$, —CH═CH—CH═CH—CH$_3$, —CH$_2$NH$_2$, —CH$_2$OH, —CH$_2$SH, —CH$_2$—CH$_2$NH$_2$, —CH$_2$—CH$_2$SH, —C$_6$H$_4$—OCH$_3$, —C$_6$H$_4$—OH, —CH$_2$—CH$_2$—OCH$_3$, —CH$_2$—CH$_2$OH, —CH$_2$—OCH$_3$, —CH$_2$—C$_6$H$_4$—OCH$_3$, —CH$_2$—C$_6$H$_4$—OH, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$,

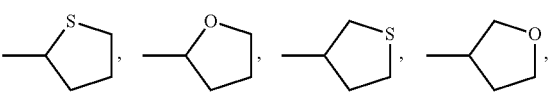

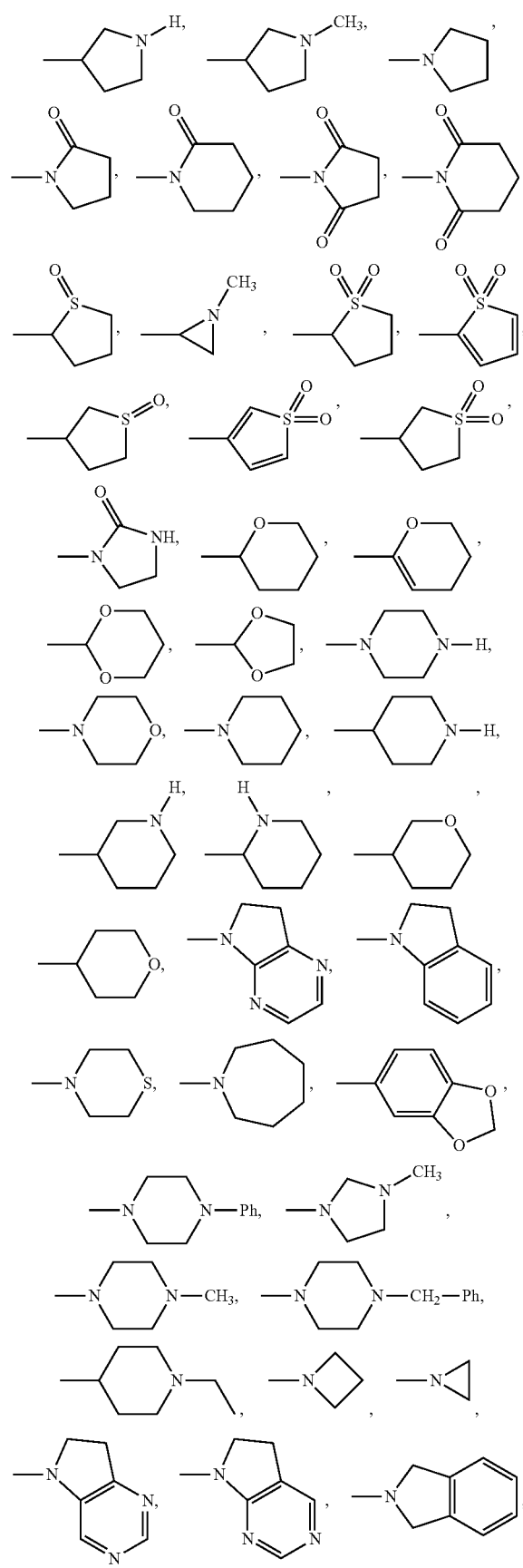
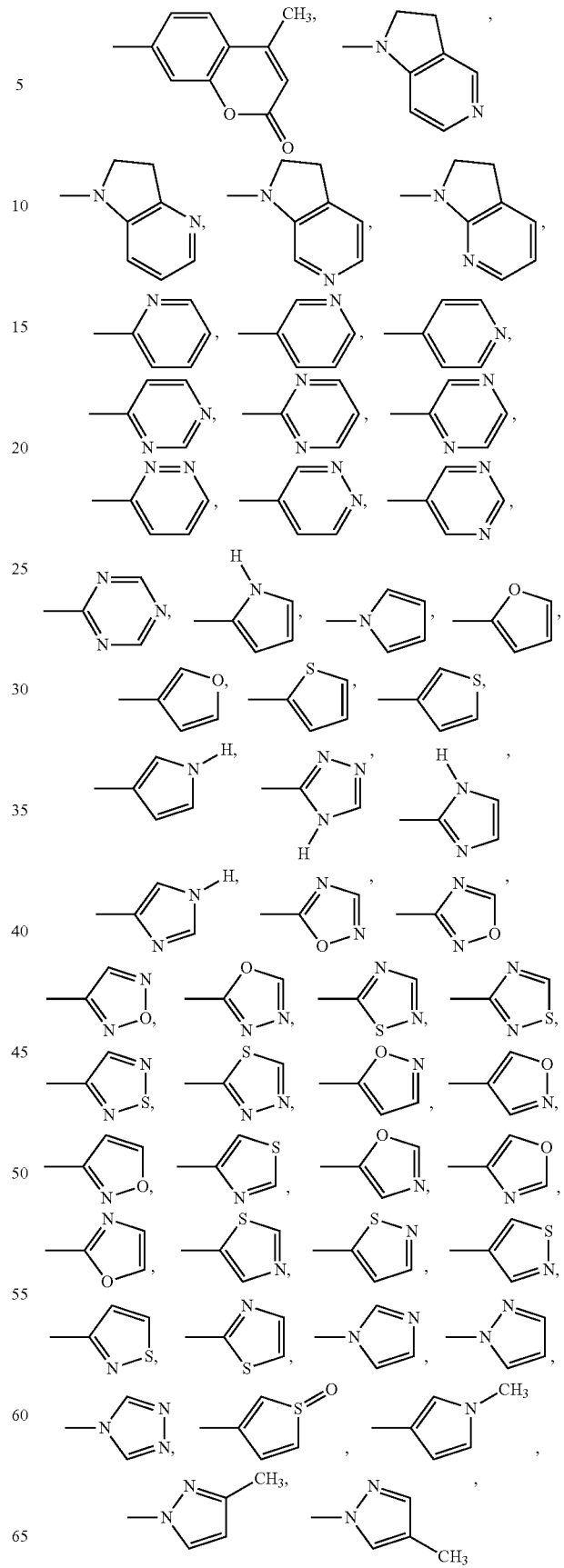

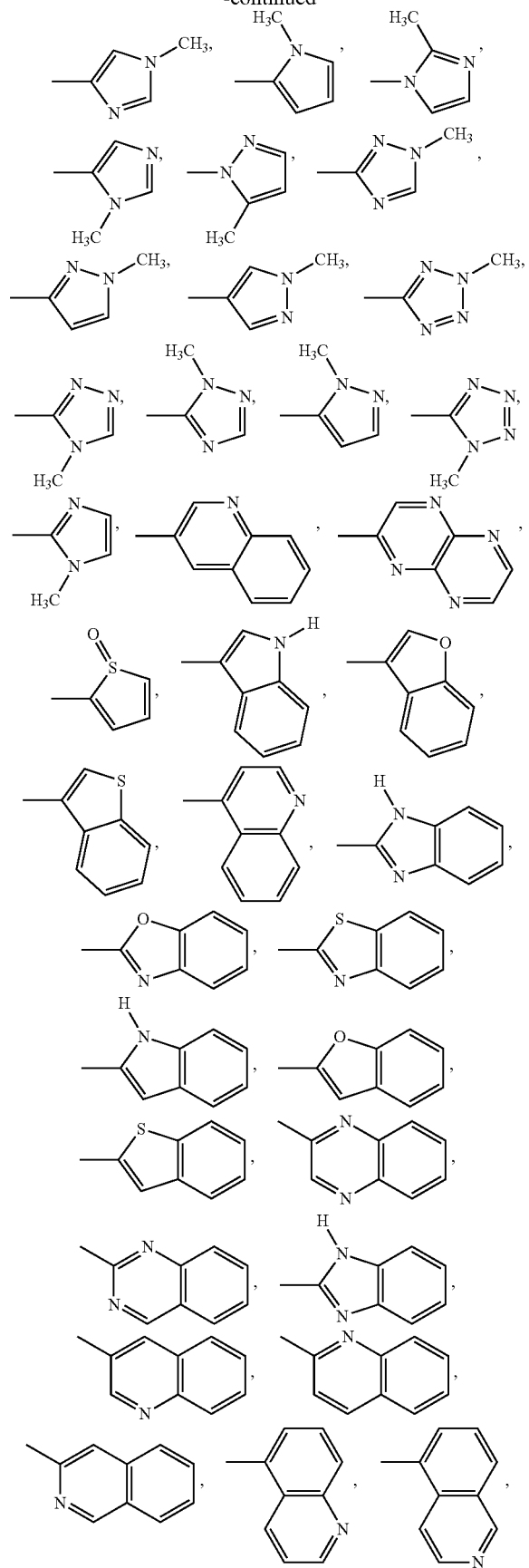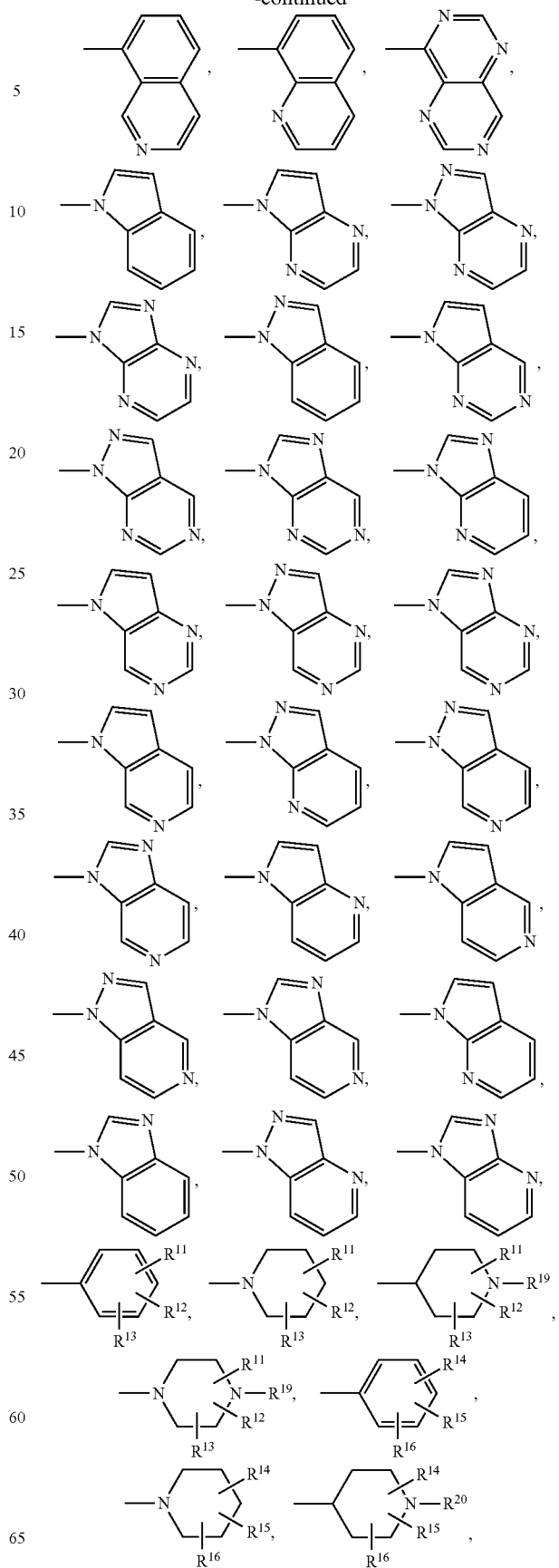

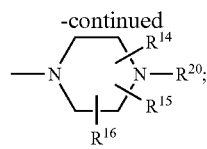

the rests $R^{11}$ to $R^{16}$ represent independently of each other the following groups:
—H, —$NH_2$, —OH, —$OCH_3$, —$OC_2H_5$, —$OC_3H_7$, —$OCF_3$, —$CF_3$, —F, —Cl, —Br, —I, —$CH_3$, —$C_2H_5$, —$C_3H_7$, —$CH(CH_3)_2$, -Ph and —ON;
as well as stereoisomeric forms, E/Z isomers, enantiomers, mixtures of enantiomers, diastereomers, mixtures of diastereomers, racemates, tautomers, anomers, keto-enol-forms, betaine forms, prodrugs, solvates, hydrates, and pharmaceutically acceptable salts of the above mentioned compounds.

The term "prodrug" describes a precursor of an active agent containing a compound according to general formula (I) to (VI) which further comprises groups cleavable under physiological conditions or which releases a compound according to general formula (I) to (VI) under physiological conditions. The term "prodrug" describes compounds according to one of the general formula (I) to (VI), wherein the rest $R^{\#}$ comprises at least one modified carboxylate group which is modified with a rest that is generally known by a person skilled in the art in that way that the carboxylate group of the rest $R^{\#}$ is released under physiological conditions and/or at least one modified hydroxyl group which is modified with a rest that is generally known by a person skilled in the art in that way that the hydroxyl group of the rest $R^{\#}$ is released under physiological conditions.

Surprisingly, it was found that the inventive compounds of general formula (I) have extraordinary potential for inhibition of tissue transglutaminase. Additionally, the pyridinone derivatives of the invention show selectivity for the TG2. It has also been found that the compounds of the invention to develop their potential have a great tolerance towards the substituents on the N-terminal end ("X" ligand). Due to this tolerance and by specific use of suitable functional groups it is possible to provide the compounds of the present invention with special features, such as a desired pH-dependent solubility profile, solubility, polarity and the like. Thus, it is possible via the N-terminal substituent to adjust the compounds of the invention to be alkaline, acidic or neutral. Due to the tolerance of the N-terminal substituent the solubility, membrane permeability, stability against microsomes and general compatibility can also be positively affected.

Due to the specially selected substituents on the C-terminal side of the compounds according to the invention the steric dimension can be adjusted very precisely, so that a binding pocket of a desired target molecule may be addressed with highly matching measurements. It has surprisingly been found that the tissue transglutaminase can selectively be inhibited by the compounds of the present invention.

Moreover, it appears that the 2-oxo-1,2-dihydropyridine residue or the 6-alkyl-2-oxo-1,2-dihydropyridine residue has an important task in order to place the acceptor-substituted double bond of the side chain in such a way in the active site of the TG2, that a thiol group of a cysteine amino acid of the TG2 can add to the Michael system. For this reason too, it is important that the amino acid in the inventive pyridinone derivatives which has the side chain with the Michael system, is attached by an amino group to position 3 of the pyridinone derivatives. Furthermore, the connection of a methylcarbamoyl group to the nitrogen in the ring of the pyridinone rest seems to be preferred for a very good inhibitory effect. Further, it has been found that a certain distance between the acceptor-substituted double bond and the alpha-carbon atom of the amino acid is necessary, by which the side chain with the Michael system is bonded. This optimal distance which should not be shorten but also not exceeded is achieved by the ethylenyl (—$CH_2$—$CH_2$—) linker. Methylenyl linker (—$CH_2$—) as well as propylenyl linker (—$CH_2$—$CH_2$—$CH_2$—) cause lower inhibition data.

Preferred are compounds of the general formula (I), (II), (III), (IV), (V) or (VI), wherein Z represents one of the following rests: —$CH_3$, —$C_2H_5$, —$C_3H_7$, —$CH(CH_3)_2$, —$OCH_2$-Ph, —$OCH_3$, —$OC_2H_5$, —$OC_3H_7$, —$OCH(CH_3)_2$, —$OCH=CH_2$ or —$OCH_2$—$CH=CH_2$, further preferred —$CH_3$, —$C_2H_5$, —$C_3H_7$, —$OCH_3$, —$OC_2H_5$, —$OC_3H_7$, —$OCH(CH_3)_2$ or —$OCH_2$-Ph, even more preferred —$CH_3$, —$C_2H_5$, —$OCH_3$, —$OC_2H_5$ or —$OCH_2$-Ph, even more preferred —$OCH_3$, —$OC_2H_5$ or —$OCH_2$-Ph, even more preferred —$OCH_3$ or —$OC_2H_5$ and especially preferred represents —$OCH_3$.

Further, compounds of the general formula (I) are preferred, wherein R* represents —H and —$CH_3$, and especially preferred, wherein R* represents —H.

$R^{\#}$ preferably represents one of the following rests: —NYY', —NH—$CH_2$—COOH, —NH—CH($CH_3$)—COOH, —NH—CH($CH_2CH_2SCH_3$)—COOH, —NH—CH($CH_2OH$)—COOH, —NH—CH($CH_2SH$)—COOH, —NH—CH($CH_2CONH_2$)—COOH, —NH—CH($CH_2CH_2CONH_2$)—COOH, —NH—CH($CH_2CH(CH_3)_2$)—$CH_2COOH$,

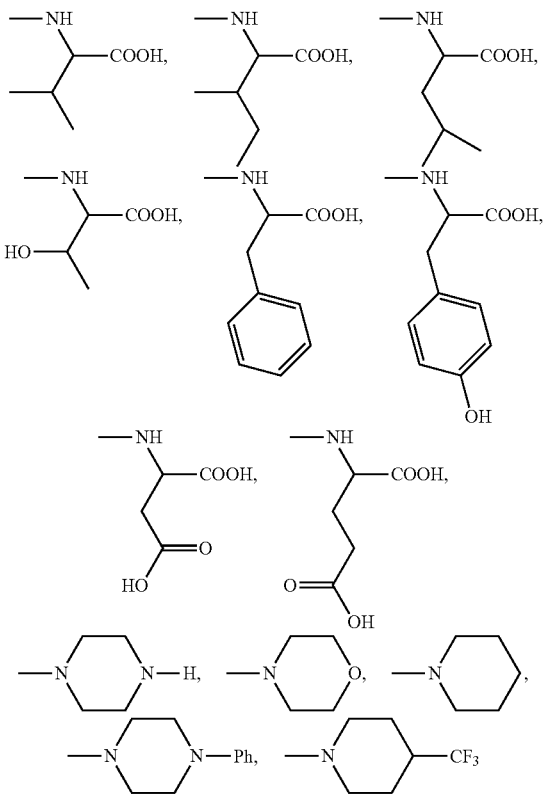

-continued

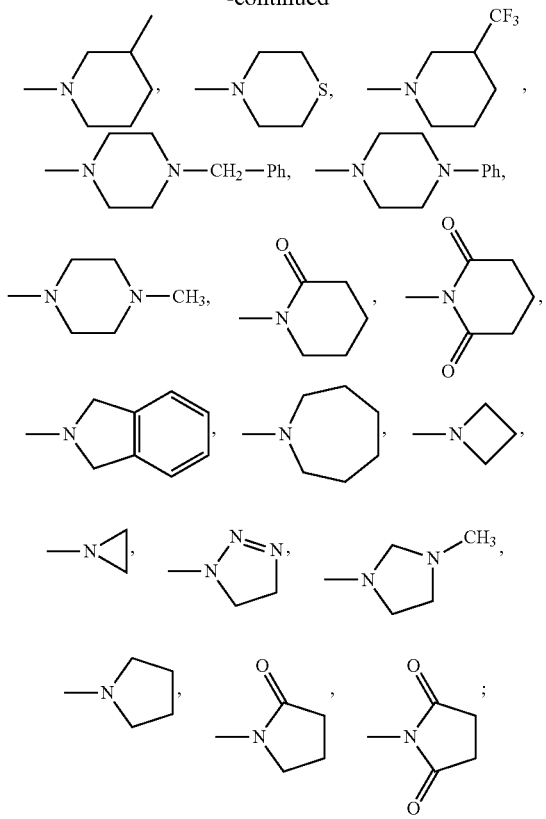

Further, compounds of the general formula (I), (II), (III), (IV), (V) or (VI) are preferred, wherein R[#] represents —NHY.

As rests Y and especially as rest Y within the rest —NHY are preferred —CHR[1]—CH$_2$R[2], —CHR[1]—CHR[2]—CH$_2$R[3], —CHR[1]—CHR[2]—CHR[3]—CH$_2$R[4], CHR[1]CHR[2]CHR[3]CHR[4]CH$_2$R[5] and CHR[1]CHR[2]CHR[3]CHR[4]CHR[5]CH$_2$R[6], further preferred —CHR[1]—CHR[2]—CH$_2$R[3], —CHR[1]—CHR[2]—CHR[3]—CH$_2$R[4] and CHR[1]CHR[2]CHR[3]CHR[4]CH$_2$R[5], even more preferred —CHR[1]—CHR[2]—CH$_3$, —CHR[1]—CHR[2]—CHR[3]—CH$_3$ and —CHR[1]—CHR[2]—CHR[3]—CH$_2$—CH$_3$ and most preferred are —CHR[1]—CH$_2$—CH$_3$, —CH$_2$—CHR[2]—CH$_3$, —CH$_2$—CHR[2]—CH$_2$—CH$_3$, —CHR[1]—CH$_2$—CH$_2$—CH$_3$, —CH$_2$—CH$_2$—CHR[3]—CH$_3$, —CH$_2$—CH$_2$—CHR[3]—CH$_2$—CH$_3$ and —CH$_2$—CHR[2]—CH$_2$—CH$_2$—CH$_3$.

In general and especially within the afore mentioned rest Y, R[1]-R[6] represent independently of each other preferably —H, —OCH$_3$, —OC$_2$H$_5$, —OC$_3$H$_7$, —CH$_2$F, —CHF$_2$, —CF$_3$, —CH$_2$Cl, —CH$_2$—CH$_2$F, —CH$_2$—CHF$_2$, —CH$_2$—CF$_3$, —CH$_3$, —C$_2$H$_5$, —C$_3$H$_7$, —CH(CH$_3$)$_2$ and —C$_4$H$_9$, further preferred —H, —CH$_2$F, —CF$_3$, —CH$_2$—CH$_2$F, —CH$_2$—CF$_3$, —CH$_3$, —C$_2$H$_5$, —C$_3$H$_7$, —CH(CH$_3$)$_2$ and —C$_4$H$_9$, even more preferred —H, —CH$_2$F, —CH$_2$—CH$_2$F, —CH$_3$, —C$_2$H$_5$, —C$_3$H$_7$ and —CH(CH$_3$)$_2$, even more preferred —H, —CH$_3$, —C$_2$H$_5$, —C$_3$H$_7$ and most preferred —H and —C$_2$H$_5$.

As rest —NHY are preferred: —NH(CH(CH$_3$)—CH$_2$—CH$_3$), —NH(CH$_2$—CH(CH$_3$)$_2$), —NH(CH(C$_2$H$_5$)$_2$), —NH(CH(CH$_3$)—CH$_2$—CH$_2$—CH$_3$), —NH(CH$_2$—CH(CH$_3$)—CH$_2$—CH$_3$), —NH(CH$_2$—CH$_2$—CH(CH$_3$)$_2$), —NH(CH(C$_2$H$_5$)—CH$_2$—CH$_2$—CH$_3$), —NH(CH$_2$—CH(C$_2$H$_5$)$_2$), —NH(CH$_2$—CH$_2$—CH(CH$_3$)—C$_2$H$_5$), —NH(CH(C$_3$H$_7$)$_2$) and —NH(CH$_2$—CH$_2$—CH(C$_2$H$_5$)$_2$).

Further, compounds of the general formula (I) are preferred, wherein
Z represents —OCH$_3$, —OCH$_2$CH$_3$, —OCH(CH$_3$)$_2$ or —OCH$_2$-Ph, R* represents —H or —CH$_3$, and R[#] represents —NHY.

Further, compounds of the general formula (I) are preferred, wherein
Z represents —OCH$_3$, —OCH$_2$CH$_3$, —OCH(CH$_3$)$_2$ or —OCH$_2$-Ph, R* represents —H or —CH$_3$, and R[#] represents —NHY,
Y represents —CH$_2$R[1], —CHR[1]—CH$_2$R[2], —CHR[1]—CHR[2]—CH$_2$R[3], CHR[1]CHR[2]CHR[3]CH$_2$R[4], or CHR[1]CHR[2]CHR[3]CHR[4]CH$_2$R[5], and
R[1] to R[5] are selected independently of each other from the following substituents: —COOH, —COOCH$_3$, —N(CH$_3$)$_2$, —N(C$_2$H$_5$)$_2$, -Ph, —CH$_3$, —C$_2$H$_5$, —CH$_2$—CH(CH$_3$)$_2$, —C(CH$_3$)$_3$,

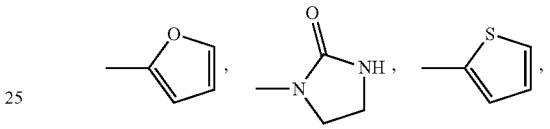

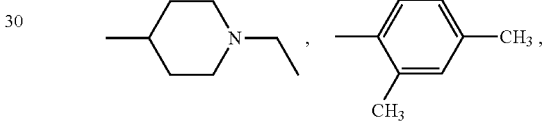

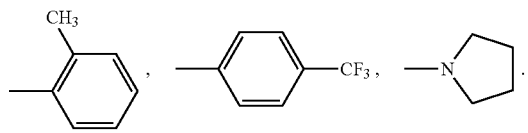

Further, compounds of the general formula (I) are preferred, wherein
Z represents —OCH$_3$, —OCH$_2$CH$_3$, —OCH(CH$_3$)$_2$ or —OCH$_2$-Ph, R* represents —H or —CH$_3$, R[#] represents —NHY, and
Y is selected from —CH$_3$, —C$_2$H$_5$, —C$_3$H$_7$, —C$_4$H$_9$, —C$_5$H$_{11}$, —C$_2$H$_4$—CH(CH$_3$)$_2$, —CH(CH$_3$)—CH$_2$—CH(CH$_3$)$_2$, —CH$_2$—CH(C$_2$H$_5$)$_2$, —CH$_2$—CH(CH$_3$)—C$_2$H$_5$, —C$_2$H$_4$—C(CH$_3$)$_3$, —C$_2$H$_4$—CH(C$_2$H$_5$)$_2$,

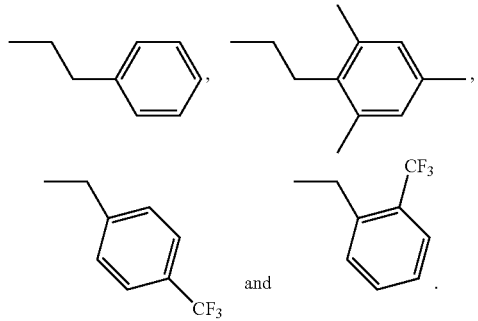

Furthermore compounds of the general formula (I) are preferred, wherein
X represents —CH$_2$R$^7$, —CHR$^7$—CH$_2$R$^8$,

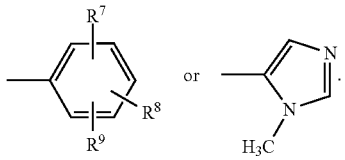 or 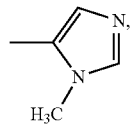

Also compounds of the general formula (I) are preferred, wherein
Z represents —OCH$_3$, —OCH$_2$CH$_3$ or —OCH$_2$-Ph,
X represents

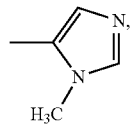

R* represents —H or —CH$_3$,
R$^\#$ represents —NHY,
Y is selected from —CH$_3$, —C$_2$H$_5$, —C$_3$H$_7$, —C$_4$H$_9$, —C$_5$H$_{11}$, —C$_2$H$_4$—CH(CH$_3$)$_2$, —CH(CH$_3$)—CH$_2$—CH(CH$_3$)$_2$, —CH$_2$—CH(C$_2$H$_5$)$_2$, —CH$_2$—CH(CH$_3$)—C$_2$H$_5$, —C$_2$H$_4$—C(CH$_3$)$_3$, —C$_2$H$_4$—CH(C$_2$H$_5$)$_2$,

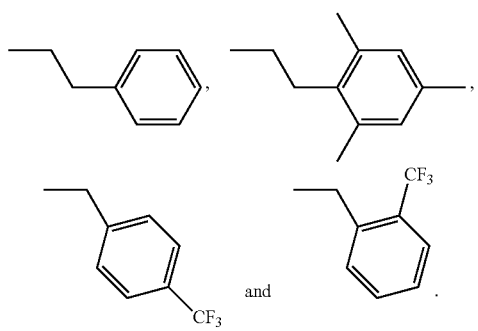

Equally, compounds of the general formula (I) are preferred, wherein
Z represents —OCH$_3$, —OCH$_2$CH$_3$ or —OCH$_2$-Ph,
X represents —CH$_2$R$^7$ or —CHR$^7$—CH$_2$R$^8$
R* represents —H or —CH$_3$,
R$^\#$ represents —NHY,
Y is selected from —CH$_3$, —C$_2$H$_5$, —C$_3$H$_7$, —C$_4$H$_9$, —C$_5$H$_{11}$, —C$_2$H$_4$—CH(CH$_3$)$_2$, —CH(CH$_3$)—CH$_2$—CH(CH$_3$)$_2$, —CH$_2$—CH(C$_2$H$_5$)$_2$, —CH$_2$—CH(CH$_3$)—C$_2$H$_5$, —C$_2$H$_4$—C(CH$_3$)$_3$, —C$_2$H$_4$—CH(C$_2$H$_5$)$_2$,

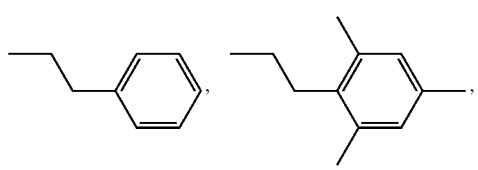

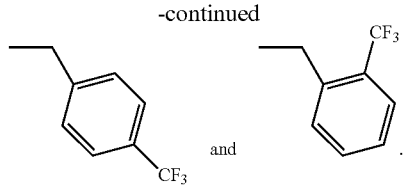

Additionally, compounds of the general formula (I) are preferred, wherein
Z represents —OCH$_3$, —OCH$_2$CH$_3$ or —OCH$_2$-Ph,
X represents

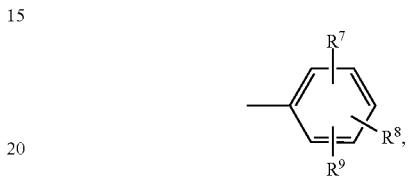

R* represents —H or —CH$_3$,
R$^\#$ represents —NHY,
Y is selected from —CH$_3$, —C$_2$H$_5$, —C$_3$H$_7$, —C$_4$H$_9$, —C$_5$H$_{11}$, —C$_2$H$_4$—CH(CH$_3$)$_2$, —CH(CH$_3$)—CH$_2$—CH(CH$_3$)$_2$, —CH$_2$—CH(C$_2$H$_5$)$_2$, —CH$_2$—CH(CH$_3$)—C$_2$H$_5$, —C$_2$H$_4$—C(CH$_3$)$_3$, —C$_2$H$_4$—CH(C$_2$H$_5$)$_2$,

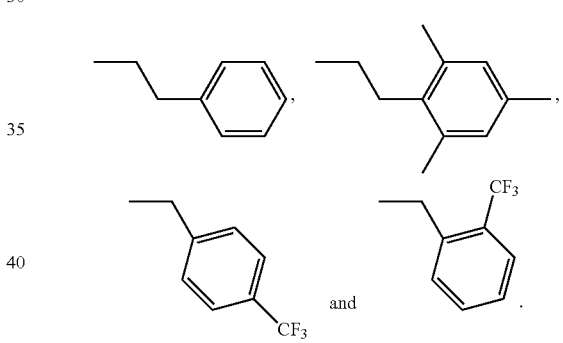

Furthermore compounds of the general formula (I) are especially preferred, wherein
Z represents —OCH$_3$, —OCH$_2$CH$_3$ or —OCH$_2$-Ph,
E$^1$ represents —CO— or —SO$_2$—,
E$^2$ represents —CO—,
R* represents one of the following rests: —H or —CH$_3$,
R$^\#$ represents one of the following rests: —NYY',

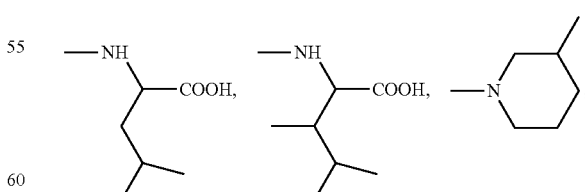

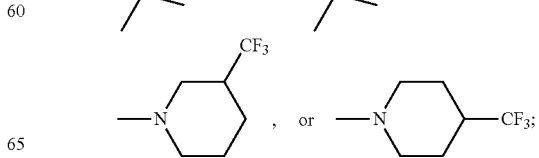

Y' represents —H;
Y represents —CH$_2$R$^1$, —CHR$^1$—CH$_2$R$^2$, —CHR$^1$—CHR$^2$—CH$_2$R$^3$, CHR$^1$CHR$^2$CHR$^3$CH$_2$R$^4$ or CHR$^1$CHR$^2$CHR$^3$CHR$^4$CH$_2$R$^9$,
R$^1$ to R$^5$ are selected independently of each other from: —H, —CH$_3$, —C$_2$H$_5$, -Ph, —CH$_2$—CH(CH$_3$)$_2$, —N(CH$_3$)$_2$, —N(C$_2$H$_5$)$_2$, —COOH, —COOCH$_3$, —C(CH$_3$)$_3$,

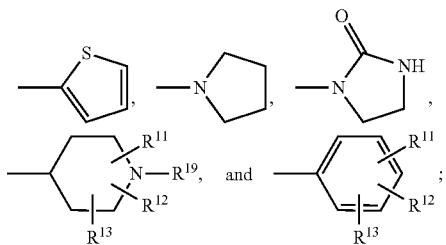

R$^{11}$ to R$^{13}$ independently of each other mean —H, —CH$_3$, —C$_2$H$_5$ or —CF$_3$,
R$^{19}$ means —C$_2$H$_5$,
X is selected from —CH$_2$R$^7$, —CHR$^7$—CH$_2$R$^8$, —O—CH$_2$R$^7$,

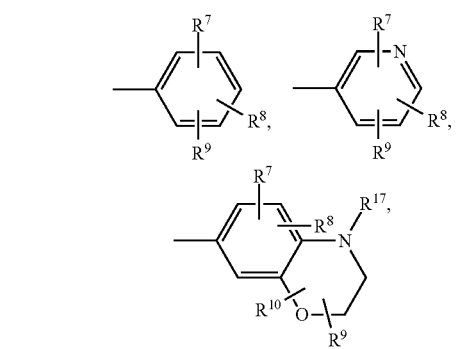

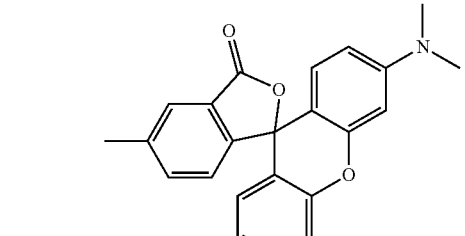

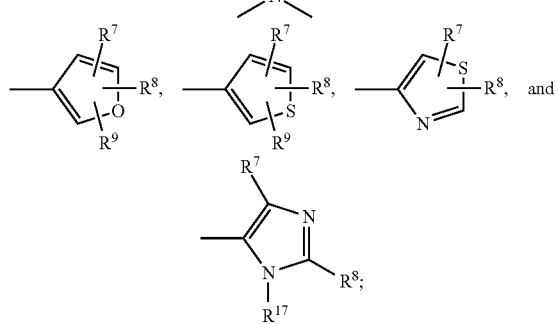

R$^7$ to R$^{10}$ independently of each other mean —H, —OH, —COOH, —SO$_2$NH$_2$, —CH$_3$, —CF$_3$, —NH—CO—NH$_2$, —NH$_2$*HOOCCF$_3$, —NH$_2$,

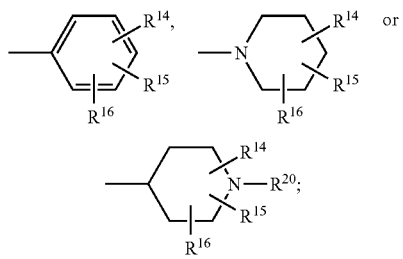

R$^{14}$ to R$^{16}$ independently of each other mean —H, —Cl or —CH$_3$, and
R$^{17}$ and R$^{20}$ mean —CH$_3$.

Furthermore compounds of the general formula (I) are preferred, wherein
Z represents —OCH$_3$,
E$^2$ represents —CO—,
R* represents —H or —CH$_3$,
R$^\#$ represents —NHY,
Y represents —C$_2$H$_4$—CH(CH$_3$)$_2$, —CH$_2$—CH(CH$_3$)—C$_2$H$_5$, —C$_2$H$_4$—C(CH$_3$)$_3$ or —C$_2$H$_4$—CH(C$_2$H$_5$)$_2$,
X means one of the following rests —CH$_2$R$^7$, —CHR$^7$—CH$_2$R$^8$, —O—CH$_2$R$^7$,

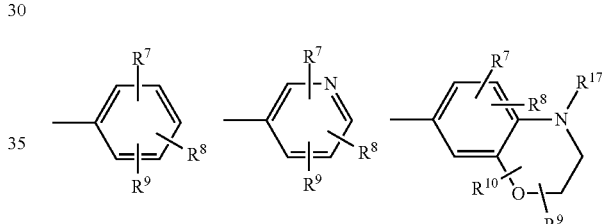

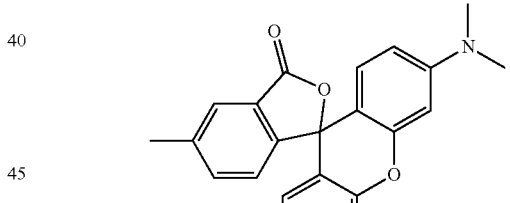

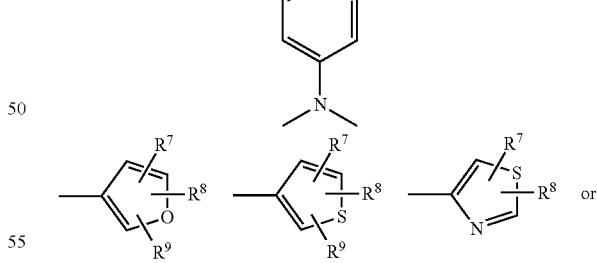

R$^7$ to R$^{10}$ means independently of each other —H, —OH, —COOH, —SO$_2$NH$_2$, —CH$_3$, —CF$_3$, —NH—CO—NH$_2$, —NH$_2$*HOOCCF$_3$, —NH$_2$,

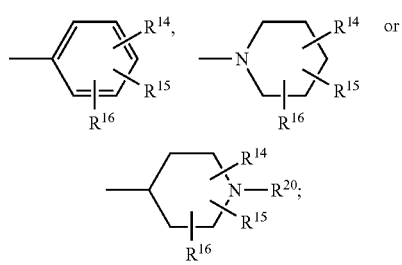

$R^{17}$ means —$CH_3$, $R^{14}$ to $R^{16}$ means independently of each other —H, —Cl or —$CH_3$, and $R^{20}$ means —$C_2H_5$.

Furthermore, $R^\#$ is preferably selected from the following rests:

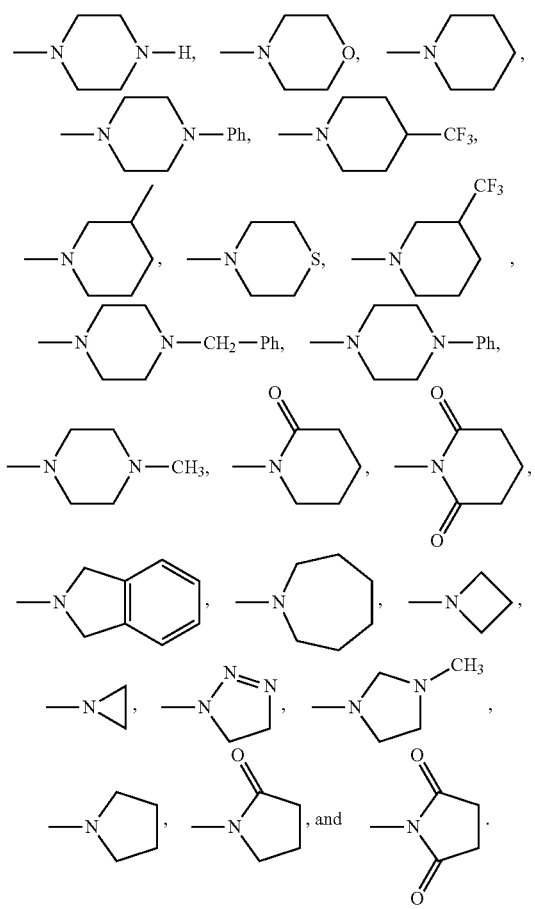

Of the above mentioned rests the following rests for $R^\#$ are especially preferred:

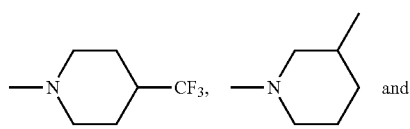

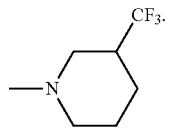

A preferred embodiment of the present invention relates to compounds of general formula (II):

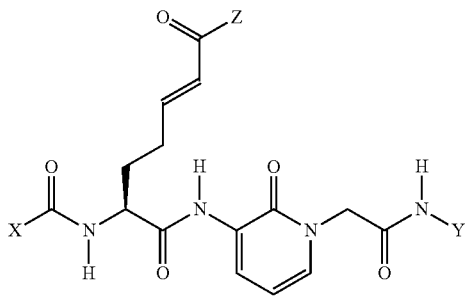

(II)

wherein

X, Y and Z have the meaning as defined above and preferably

Z represents —$OCH_3$, —$OCH_2CH_3$, —$OCH(CH_3)_2$ or —$OCH_2$-Ph.

Also, the compounds of general formula (II) are preferred

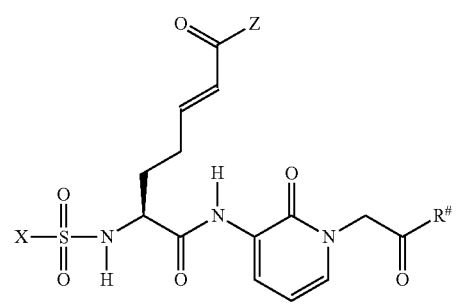

(III)

with X, Z and $R^\#$ as defined herein.

The compounds of general formulas (IV), (V) and (VI) are preferred, too:

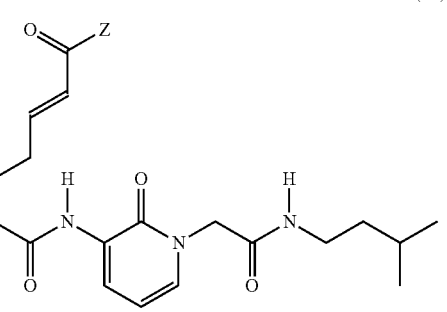

(IV)

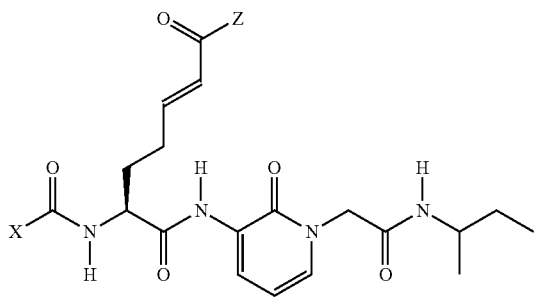

(V)

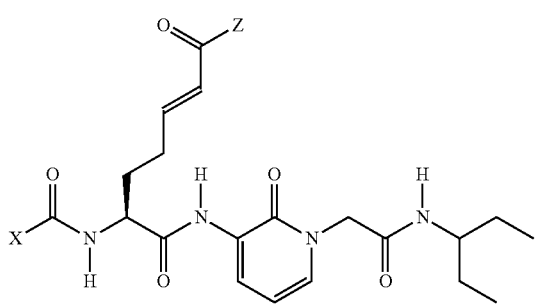

(VI)

with X and Z as defined herein, preferred with Z as —OCH$_3$, —OCH$_2$CH$_3$ or —OCH$_2$-Ph and even more preferred with Z as —OCH$_3$.

According to the present invention, compounds selected from the group consisting of:

(S,E)-ethyl 6-(benzyloxycarbonylamino)-7-oxo-7-(2-oxo-1-(2-oxo-2-(2,4,6-trimethylphenethylamino)ethyl)-1,2-dihydropyridin-3-ylamino)hept-2-enoate (A1)

(S,E)-ethyl 6-(benzyloxycarbonylamino)-7-(1-(2-(isopentylamino)-2-oxoethyl)-6-methyl-2-oxo-1,2-dihydropyridin-3-ylamino)-7-oxohept-2-enoate (A2)

(S,E)-ethyl 6-(benzyloxycarbonylamino)-7-(1-(2-(isopentylamino)-2-oxoethyl)-2-oxo-1,2-dihydropyridin-3-ylamino)-7-oxohept-2-enoate (A3)

(S,E)-ethyl 6-acetamido-7-(1-(2-(isopentylamino)-2-oxoethyl)-6-methyl-2-oxo-1,2-dihydropyridin-3-ylamino)-7-oxohept-2-enoate (A4)

3-(2-(3-((S,E)-2-(benzyloxycarbonylamino)-7-ethoxy-7-oxohept-5-enamido)-6-methyl-2-oxopyridin-1(2H)-yl)acetamido)-5-methylhexanoic acid (A5)

(S,E)-isopropyl 6-acetamido-7-(1-(2-(isopentylamino)-2-oxoethyl)-2-oxo-1,2-dihydropyridin-3-ylamino)-7-oxohept-2-enoate (A6)

(S,E)-ethyl 6-acetamido-7-(1-(2-(isopentylamino)-2-oxoethyl)-2-oxo-1,2-dihydropyridin-3-ylamino)-7-oxohept-2-enoate (A7)

(S,E)-ethyl 7-(6-methyl-2-oxo-1-(2-oxo-2-(phenethylamino)ethyl)-1,2-dihydropyridin-3-ylamino)-6-(nicotinamido)-7-oxohept-2-enoate (A8)

(S,E)-ethyl 6-((4-chlorophenyl)methylsulfonamido)-7-(1-(2-(isopentylamino)-2-oxoethyl)-2-oxo-1,2-dihydropyridin-3-ylamino)-7-oxohept-2-enoate (A9)

(S,E)-ethyl 6-benzamido-7-(1-(2-(isopentylamino)-2-oxoethyl)-2-oxo-1,2-dihydropyridin-3-ylamino)-7-oxohept-2-enoate (A10)

(S,E)-ethyl 6-(furan-3-carboxamido)-7-(1-(2-(isopentylamino)-2-oxoethyl)-2-oxo-1,2-dihydropyridin-3-ylamino)-7-oxohept-2-enoate (A11)

(S,E)-ethyl 7-(1-(2-(isopentylamino)-2-oxoethyl)-2-oxo-1,2-dihydropyridin-3-ylamino)-7-oxo-6-(thiophene-3-carboxamido)hept-2-enoate (A12)

(S,E)-ethyl 6-(furan-3-sulfonamido)-7-(1-(2-(isopentylamino)-2-oxoethyl)-2-oxo-1,2-dihydropyridin-3-ylamino)-7-oxohept-2-enoate (A13)

(S,E)-ethyl 7-(1-(2-(isopentylamino)-2-oxoethyl)-2-oxo-1,2-dihydropyridin-3-ylamino)-7-oxo-6-(4-sulfamoylbenzamido)hept-2-enoate (A14)

(S,E)-ethyl 7-(1-(2-(isopentylamino)-2-oxoethyl)-2-oxo-1,2-dihydropyridin-3-ylamino)-6-(5-methylthiazole-4-carboxamido)-7-oxohept-2-enoate (A15)

(S,E)-ethyl 7-(1-(2-(isopentylamino)-2-oxoethyl)-2-oxo-1,2-dihydropyridin-3-ylamino)-6-(nicotinamido)-7-oxohept-2-enoate (A16)

(S,E)-ethyl 6-(3,5-bis(trifluoromethyl)benzamido)-7-(1-(2-(isopentylamino)-2-oxoethyl)-2-oxo-1,2-dihydropyridin-3-ylamino)-7-oxohept-2-enoate (A17)

(S,E)-ethyl 7-(1-(2-(isopentylamino)-2-oxoethyl)-2-oxo-1,2-dihydropyridine-3-ylamino)-7-oxo-6-(4-(piperidin-1-yl)benzamido)hept-2-enoate (A18)

(S,E)-ethyl 7-(1-(2-(isopentylamino)-2-oxoethyl)-2-oxo-1,2-dihydropyridin-3-ylamino)-6-(1-methyl-1H-imidazole-5-carboxamido)-7-oxohept-2-enoate (A19)

(S,E)-ethyl 7-(1-(2-(isopentylamino)-2-oxoethyl)-2-oxo-1,2-dihydropyridin-3-ylamino)-6-(4-(4-methylpiperazine-1-yl)benzamido)-7-oxohept-2-enoate (A20)

(S,E)-ethyl 7-(1-(2-(isopentylamino)-2-oxoethyl)-2-oxo-1,2-dihydropyridin-3-ylamino)-6-(4-methyl-3,4-dihydro-2H-benzo[b][1,4]oxazine-7-carboxamido)-7-oxohept-2-enoate (A21)

(S,E)-ethyl 7-(1-(2-(isopentylamino)-2-oxoethyl)-2-oxo-1,2-dihydropyridin-3-ylamino)-7-oxo-6-(phenylsulfonamido)hept-2-enoate (A22)

(S,E)-5-(N-(7-ethoxy-1-(1-(2-(isopentylamino)-2-oxoethyl)-2-oxo-1,2-dihydropyridin-3-ylamino)-1,7-dioxohept-5-en-2-yl)sulfamoyl)-2-hydroxybenzoic acid (A23)

(S,E)-4-(7-ethoxy-1-(1-(2-(isopentylamino)-2-oxoethyl)-2-oxo-1,2-dihydropyridin-3-ylamino)-1,7-dioxohept-5-en-2-ylamino)-4-oxobutanoic acid (A24)

(S,E)-ethyl 6-acetamido-7-(1-(2-(2-(diethylamino)ethylamino)-2-oxoethyl)-2-oxo-1,2-dihydropyridin-3-ylamino)-7-oxohept-2-enoate (A25)

(5,E)-4-(1-(1-(2-(2-(diethylamino)ethylamino)-2-oxoethyl)-2-oxo-1,2-dihydropyridin-3-ylamino)-7-ethoxy-1,7-dioxohept-5-en-2-ylamino)-4-oxobutanoic acid (A26)

(S,E)-ethyl 6-acetamido-7-(1-(2-(2-(dimethylamino)ethylamino)-2-oxoethyl)-2-oxo-1,2-dihydropyridin-3-ylamino)-7-oxohept-2-enoate (A27)

(S,E)-methyl 6-acetamido-7-(1-(2-(isopentylamino)-2-oxoethyl)-2-oxo-1,2-dihydropyridin-3-ylamino)-7-oxohept-2-enoate (A28)

(S,E)-methyl 6-acetamido-7-(1-(2-(isopentylamino)-2-oxoethyl)-2-oxo-1,2-dihydropyridin-3-ylamino)-7-oxohept-2-enoate (A29)

(S,E)-4-(7-ethoxy-1-(1-(2-(2-ethyl butylamino)-2-oxoethyl)-2-oxo-1,2-dihydropyridin-3-ylamino)-1,7-dioxohept-5-en-2-ylamino)-4-oxobutanoic acid (A30)

(S,E)-ethyl 6-acetamido-7-(1-(2-((S)-1-methoxy-4-methyl-1-oxopentan-2-ylamino)-2-oxoethyl)-2-oxo-1,2-dihydropyridin-3-ylamino)-7-oxohept-2-enoate (A31)

4-((S,E)-7-ethoxy-1-(1-(2-((S)-1-methoxy-4-methyl-1-oxopentan-2-ylamino)-2-oxoethyl)-2-oxo-1,2-dihydropyridin-3-ylamino)-1,7-dioxohept-5-en-2-ylamino)-4-oxobutanoic acid (A32)

(S,E)-ethyl 6-acetamido-7-(1-(2-((R)-1-methoxy-4-methyl-1-oxopentan-2-ylamino)-2-oxoethyl)-2-oxo-1,2-dihydropyridin-3-ylamino)-7-oxohept-2-enoate (A33)

4-((S,E)-7-ethoxy-1-(1-(2-((R)-1-methoxy-4-methyl-1-oxopentan-2-ylamino)-2-oxoethyl)-2-oxo-1,2-dihydropyridin-3-ylamino)-1,7-dioxohept-5-en-2-ylamino)-4-oxobutanoic acid (A34)

(S,E)-ethyl 6-acetamido-7-(1-(2-((2S,3R)-1-methoxy-3-methyl-1-oxopentan-2-ylamino)-2-oxoethyl)-2-oxo-1,2-dihydropyridin-3-ylamino)-7-oxohept-2-enoate (A35)

4-((S,E)-7-ethoxy-1-(1-(2-((2S,3R)-1-methoxy-3-methyl-1-oxopentan-2-ylamino)-2-oxoethyl)-2-oxo-1,2-dihydropyridin-3-ylamino)-1,7-dioxohept-5-en-2-ylamino)-4-oxobutanoic acid (A36)

(S,E)-4-(7-ethoxy-1,7-dioxo-1-(2-oxo-1-(2-oxo-2-(4-(trifluoromethyl)benzylamino)ethyl)-1,2-dihydropyridin-3-ylamino)hept-5-en-2-ylamino)-4-oxobutanoic acid (A37)

(S,E)-4-(1-(1-(2-(3,3-dimethylbutylamino)-2-oxoethyl)-2-oxo-1,2-dihydropyridin-3-ylamino)-7-ethoxy-1,7-dioxohept-5-en-2-ylamino)-4-oxobutanoic acid (A38)

(S,E)-ethyl 6-acetamido-7-(1-(2-(3,3-dimethylbutylamino)-2-oxoethyl)-2-oxo-1,2-dihydropyridin-3-ylamino)-7-oxohept-2-enoate (A39)

(S,E)-ethyl 6-acetamido-7-(1-(2-((S)-1-methoxy-4,4-dimethyl-1-oxopentan-2-ylamino)-2-oxoethyl)-2-oxo-1,2-dihydropyridin-3-ylamino)-7-oxohept-2-enoate (A40)

4-((S,E)-7-ethoxy-1-(1-(2-((S)-1-methoxy-4,4-dimethyl-1-oxopentan-2-ylamino)-2-oxoethyl)-2-oxo-1,2-dihydropyridin-3-ylamino)-1,7-dioxohept-5-en-2-ylamino)-4-oxobutanoic acid (A41)

(S,E)-ethyl 6-acetamido-7-(1-(2-(3-ethylpentylamino)-2-oxoethyl)-2-oxo-1,2-dihydropyridin-3-ylamino)-7-oxohept-2-enoate (A42)

(S,E)-4-(7-ethoxy-1-(1-(2-(3-ethylpentylamino)-2-oxoethyl)-2-oxo-1,2-dihydropyridin-3-ylamino)-1,7-dioxohept-5-en-2-ylamino)-4-oxobutanoic acid (A43)

(S,E)-4-(7-ethoxy-1,7-dioxo-1-(2-oxo-1-(2-oxo-2-(2-(trifluoromethyl)benzylamino)ethyl)-1,2-dihydropyridin-3-ylamino)hept-5-en-2-ylamino)-4-oxobutanoic acid (A44)

(S,E)-4-(7-ethoxy-1,7-dioxo-1-(2-oxo-1-(2-oxo-2-(4-(trifluoromethyl)piperidine-1-yl)ethyl)-1,2-dihydropyridin-3-ylamino)hept-5-en-2-ylamino)-4-oxobutanoic acid (A45)

(S,E)-ethyl 6-acetamido-7-oxo-7-(2-oxo-1-(2-oxo-2-(2-(pyrrolidine-1-yl)ethylamino)ethyl)-1,2-dihydropyridin-3-ylamino)hept-2-enoate (A46)

(S,E)-4-(7-ethoxy-1,7-dioxo-1-(2-oxo-1-(2-oxo-2-(2-(thiophen-2-yl)ethylamino)ethyl)-1,2-dihydropyridin-3-ylamino)hept-5-en-2-ylamino)-4-oxobutanoic acid (A47)

(S,E)-ethyl 6-acetamido-7-(1-(2-((1-ethylpiperidin-4-yl)methylamino)-2-oxoethyl)-2-oxo-1,2-dihydropyridin-3-ylamino)-7-oxohept-2-enoate (A48)

(S,E)-4-(7-ethoxy-1,7-dioxo-1-(2-oxo-1-(2-oxo-2-(2-(2-oxoimidazolidin-1-yl)ethylamino)ethyl)-1,2-dihydropyridin-3-ylamino)hept-5-en-2-ylamino)-4-oxobutanoic acid (A49)

(6S,E)-ethyl 6-acetamido-7-(1-(2-(2-methylbutylamino)-2-oxoethyl)-2-oxo-1,2-dihydropyridin-3-ylamino)-7-oxohept-2-enoate (A50)

4-((2S,E)-7-ethoxy-1-(1-(2-(2-methylbutylamino)-2-oxoethyl)-2-oxo-1,2-dihydropyridin-3-ylamino)-1,7-dioxohept-5-en-2-ylamino)-4-oxobutanoic acid (A51)

(6S, E)-ethyl 6-acetamido-7-(1-(2-(3-methyl piperidine-1-yl)-2-oxoethyl)-2-oxo-1,2-dihydropyridine-3-ylamino)-7-oxohept-2-enoate (A52)

(2S,3R)-2-(2-(3-((S,E)-7-ethoxy-2-(1-methyl-1H-imidazole-5-carboxamido)-7-oxohept-5-enamido)-2-oxopyridin-1(2H)-yl)acetamido)-3-methylpentanoic acid (A53)

(S,E)-ethyl 6-acetamido-7-(1-(2-(isobutylamino)-2-oxoethyl)-2-oxo-1,2-dihydropyridin-3-ylamino)-7-oxohept-2-enoate (A54)

(6S, E)-ethyl 6-acetamido-7-(1-(2-(3-methylbutan-2-ylamino)-2-oxoethyl)-2-oxo-1,2-dihydropyridin-3-ylamino)-7-oxohept-2-enoate (A55)

(S,E)-ethyl 7-(1-(2-(isopentylamino)-2-oxoethyl)-2-oxo-1,2-dihydropyridin-3-ylamino)-7-oxo-6-(3-ureidopropanamido)hept-2-enoate (A56)

(S,E)-ethyl 6-acetamido-7-(1-(2-((S)-1-methoxy-3-methyl-1-oxobutan-2-ylamino)-2-oxoethyl)-2-oxo-1,2-dihydropyridin-3-ylamino)-7-oxohept-2-enoate (A57)

(S,E)-ethyl 7-(1-(2-(2-ethyl butylamino)-2-oxoethyl)-2-oxo-1,2-dihydropyridin-3-ylamino)-6-(1-methyl-1H-imidazole-5-carboxamido)-7-oxohept-2-enoate (A58)

(2S,3R)-2-(2-(3-((S,E)-2-benzamido-7-ethoxy-7-oxohept-5-enamido)-2-oxopyridin-1(2H)-yl)acetamido)-3-methylpentanoic acid (A59)

(2S,3R)-2-(2-(3-((S,E)-7-Methoxy-2-(1-methyl-1H-imidazole-5-carboxamido)-7-oxohept-5-enamido)-2-oxopyridin-1(2H)-yl)acetamido)-3-methylpentanoic acid (A60)

(2S,3R)-2-(2-(3-((S,E)-2-benzamido-7-methoxy-7-oxohept-5-enamido)-2-oxopyridin-1(2H)-yl)acetamido)-3-methylpentanoic acid (A61)

(S,E)-ethyl 6-acetamido-7-(1-(2-(2-ethylbutylamino)-2-oxoethyl)-2-oxo-1,2-dihydropyridin-3-ylamino)-7-oxohept-2-enoate (A62)

(S,E)-methyl 7-(1-(2-(2-ethyl butylamino)-2-oxoethyl)-2-oxo-1,2-dihydropyridin-3-ylamino)-6-(1-methyl-1H-imidazole-5-carboxamido)-7-oxohept-2-enoate A63

(6S, E)-methyl 6-acetamido-7-(1-(2-(3-methylpiperidin-1-yl)-2-oxoethyl)-2-oxo-1,2-dihydropyridin-3-ylamino)-7-oxohept-2-enoate (A64)

(S,E)-methyl 6-acetamido-7-oxo-7-(2-oxo-1-(2-oxo-2-(4-(trifluoromethyl)piperidin-1-yl)ethyl)-1,2-dihydropyridin-3-ylamino)hept-2-enoate (A65)

(6S, E)-methyl 6-acetamido-7-oxo-7-(2-oxo-1-(2-oxo-2-(3-(trifluoromethyl)piperidin-1-yl)ethyl)-1,2-dihydropyridin-3-ylamino)hept-2-enoate (A66)

(S,E)-methyl 7-(1-(2-(2-ethyl butylamino)-2-oxoethyl)-2-oxo-1,2-dihydropyridin-3-ylamino)-6-(nicotinamido)-7-oxohept-2-enoate (A67)

(6S, E)-methyl 6-(2-aminopropanamido)-7-(1-(2-(2-ethylbutylamino)-2-oxoethyl)-2-oxo-1,2-dihydropyridin-3-ylamino)-7-oxohept-2-enoate 2,2,2-trifluoroacetate (A68)

(S,E)-methyl 6-(2-aminoacetamido)-7-(3-((2-(2-ethylbutylamino)-2-oxoethyl)(methyl)amino)-3-oxoprop-1-en-2-ylamino)-7-oxohept-2-enoate 2,2,2-trifluoroacetate (A69)

(S,E)-methyl 6-(2-aminobenzamido)-7-(1-(2-(2-ethylbutylamino)-2-oxoethyl)-2-oxo-1,2-dihydropyridin-3-ylamino)-7-oxohept-2-enoate 2,2,2-trifluoroacetate (A70)

(S,E)-methyl 6-(3',6'-bis(dimethylamino)-3-oxo-3H-spiro[isobenzofuran-1,9'-xanthene]-5-ylcarboxamido)-7-(1-(2-(2-ethylbutylamino)-2-oxoethyl)-2-oxo-1,2-dihydropyridin-3-ylamino)-7-oxohept-2-enoate (A71)

(S,E)-ethyl 6-acetamido-7-(1-(2-(isopentylamino)-2-oxoethyl)-2-oxo-1,2-dihydropyridin-3-ylamino)-7-oxohept-2-enoate (A72)

(S,E)-methyl 6-acetamido-7-(1-(2-(isopentylamino)-2-oxoethyl)-2-oxo-1,2-dihydropyridin-3-ylamino)-7-oxohept-2-enoate (A73)

(S,E)-ethyl 7-(1-(2-(2-ethylbutylamino)-2-oxoethyl)-2-oxo-1,2-dihydropyridin-3-ylamino)-6-(1-methyl-1H-imidazole-5-carboxamido)-7-oxohept-2-enoate (A74)

(2S,3R)-2-(2-(3-((S,E)-2-benzamido-7-methoxy-7-oxohept-5-enamido)-2-oxopyridin-1(2H)-yl)acetamido)-3-methylpentanoic acid (A75)

(R,E)-methyl 7-(1-(2-(2-ethylbutylamino)-2-oxoethyl)-2-oxo-1,2-dihydropyridin-3-ylamino)-6-(1-methyl-1H-imidazole-5-carboxamido)-7-oxohept-2-enoate (A76)

(5,E)-2-acetamido-N-(1-(2-(isopentylamino)-2-oxoethyl)-2-oxo-1,2-dihydropyridin-3-yl)-6-(methylsulfonyl)hex-5-enamide (A77)

(S,E)-benzyl 6-acetamido-7-(1-(2-(isopentylamino)-2-oxoethyl)-2-oxo-1,2-dihydropyridin-3-ylamino)-7-oxohept-2-enoate (A78)

(S,E)-methyl 6-acetamido-7-(1-(2-(2-ethylbutylamino)-2-oxoethyl)-2-oxo-1,2-dihydropyridin-3-ylamino)-7-oxohept-2-enoate (A79)

are especially preferred.

Therefore another aspect of the present invention relates to compounds according to the general formula (I) as medicine as well as their use in medicine. Especially preferred is the use as inhibitor for the tissue transglutaminase.

Another aspect of the present invention comprises the use of the inventive compounds of the general formula (I) for the treatment or prophylaxis of coeliac disease, fibrosis, thrombosis, neurodegenerative diseases, Huntington's disease, Parkinson's disease, Alzheimer's disease, cataract, acne, psoriasis, skin aging, candidosis and other transglutaminase dependent diseases.

The term "transglutaminase dependent diseases" comprises all diseases, dysfunctions or other impairments of the health, which are caused by or in connection with a dysfunction, perturbance or hyperactivity of transglutaminase 2 in the body.

The particular suitability of the inventive compounds of the general formula (I) is directly connected to the sterical and electronical properties which result from the molecule structure. The vinyl group substituted with at least one electron withdrawing group (Michael acceptor group) appears to be an essential unit of the transglutaminase inhibitors, and, in combination with the pyridinone-containing backbone results in potent tissue transglutaminase inhibitors. It has surprisingly been found that this combination of a pyridinone containing backbone at which a plurality of functional groups used for adjusting desired (physico-) chemical properties may be attached to the N-terminal side, together with the side group bearing the acceptor-substituted double bond has higher activity and selectivity compared to known inhibitors having Michael systems. Thus, not only the presence of a Michael acceptor-system or an acceptor-substituted double bond appears to be important, but also its further concrete structure. It has proven to be very beneficial if the side group with acceptor-substituted double bond or with Michael system is bioisostere to glutamine.

The above mentioned residues may have D- or L-configuration, wherein L-configuration is preferred.

A further aspect of the present invention relates to the provision of compounds of the general formula (I). The compounds of the invention can be prepared by attaching protecting groups (PG1, PG2 and PG3) to the amino acid Glu (glutamic acid) at the C-terminal end (PG2), and the N-terminal end (PG1 and eventually PG1') as well as at the carboxyl function (PG3) of the side chain (1), subsequently the carboxyl function of the side chain is reduced to aldehyde (2) and the aldehyde obtained is converted into an acceptor-substituted, electrophilic double bond (3). In a preferred embodiment, the protecting groups at the N-terminal end as well as at the C-terminal end are removed (4/5) and the C-terminal end is extended with a pyridinone fragment (6). After extension of the C-terminal carboxyl function the N-terminal end is deprotected and subsequently extended (7/8). In another preferred embodiment, after introduction of the acceptor-substituted double bond the N-terminal end is deprotected (4) firstly and subsequently extended with a desired substituent (5). Thereafter the protecting group at the C-terminal end is removed (6) and extended with a pyridinone fragment (7). The systematical process of the synthesis with both different, preferred embodiments is shown in the following scheme.

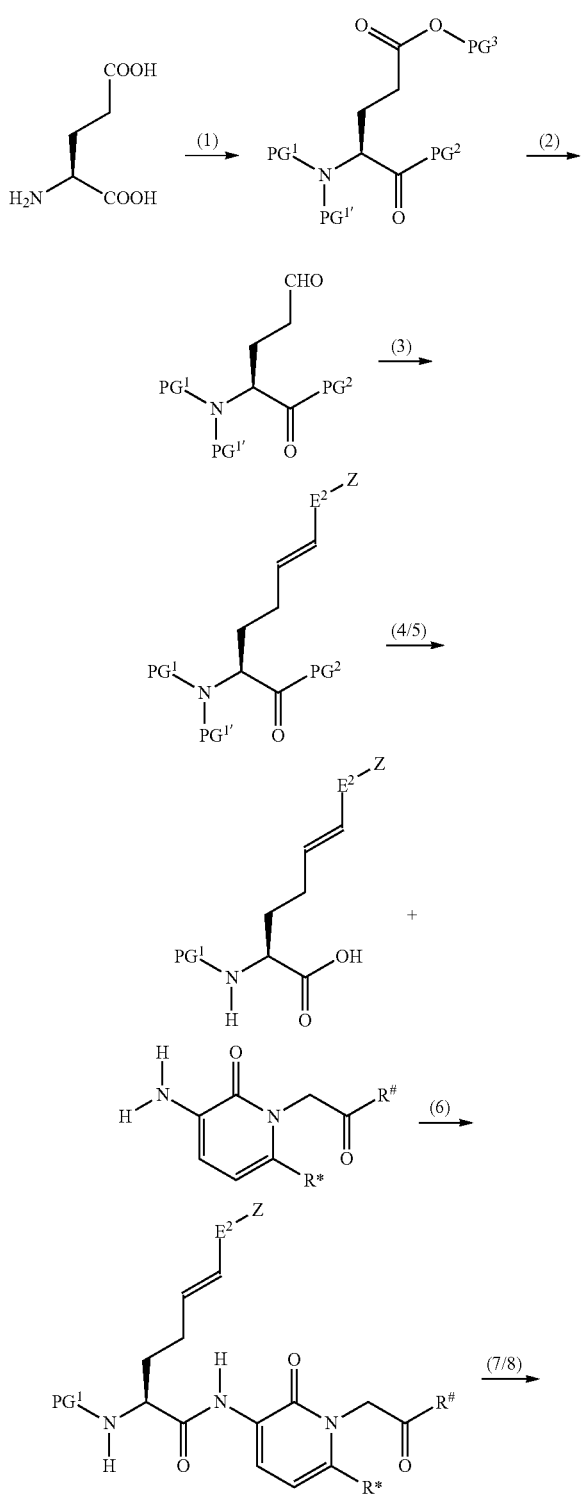

(0) Provision of glutamic acid,
(1) Attaching protecting groups (PG1, PG2 and PG3) at the C-terminal and N-terminal end as well as at the carbonyl function of the site chain of glutamic acid,
(2) Reduction of the carboxylic function of the side chain of glutamic acid to the aldehyde,
(3) Conversion of the resulting aldehyde to an acceptor-substituted electrophilic double bond
(4) Removal of a protecting group at the N-terminal end,
(5) Removal of the protecting group at the C-terminal end,
(6) Extension of the C-terminal end with a pyridinone fragment,
(7) Removal of the second protecting group at the N-terminal end,
(8) Extension of the N-terminal end.

or

Steps (0), (1), (2) and (3) as above
(4) Removal of the protecting groups at the N-terminal end,
(5) Extension of the N-terminal end,
(6) Removal of the protecting group at the C-terminal end,
(7) Extension of the C-terminal end with a pyridinone fragment wherein the rests X, Z, $E^1$, $E^2$, $R^\#$ and $R^*$ have the meaning as defined herein.

Precursors to the pyridinone fragments of the compounds according to the invention can be prepared according to the following process. Starting with a suitable 2-hydroxynicotinic acid derivative, initially, a protected amino group and at the nitrogen of the pyridine a protected carbonyl methylene group are attached and further the hydroxypyridine derivative is reacted to a pyridinone derivative (1). Subsequently, the rest $R^\#$ is inserted at the protected carbonyl function (2). Finally, the protected amino group is deprotected (3). The systematical process of the synthesis is shown in the following scheme:

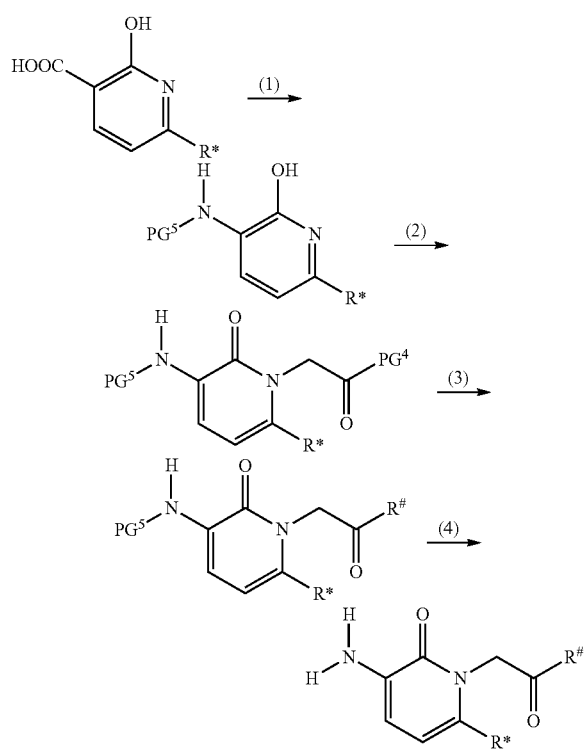

(1) Adding of a protected amino function into a 2-hydroxynicotinic acid derivative at the carboxyl function,
(2) Attaching a methyl group with a protected carbonyl function (PG4),
(3) Attaching the rest $R^\#$ at the protected carbonyl function,
(4) Deprotecting the pyridinonyl amino group, wherein the rests $R^\#$ and $R^*$ have the meaning as defined herein.

Alternatively, the precursors for the pyridinone fragments of the compounds according to the invention may also be prepared according to the following process. Starting with a suitable 2-hydroxy-3-nitropyridine derivative, initially, a protected carbonylmethylene group is added at the nitrogen of the pyridine and further the hydroxypyridine derivative is reacted to a pyridinone derivative (1). Subsequently the Rest $R^\#$ is introduced at the protected carbonyl function (2). Finally, the nitro group is reduced to an amino group (3). The systematical process of the synthesis is shown in the following scheme:

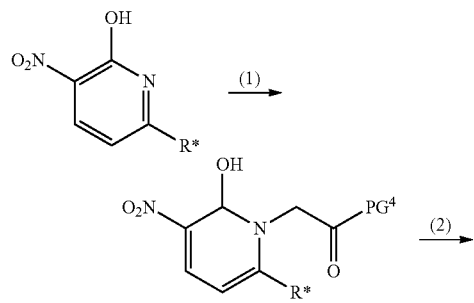

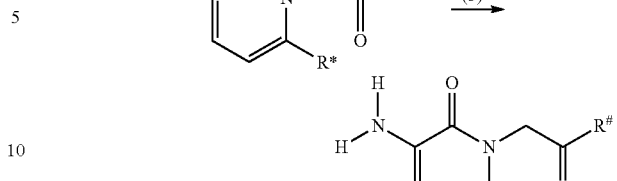

(1) Adding a methyl group with a protected carbonyl function (PG4) to a 2-hydroxy-3-nitropyridine derivative,
(2) Attachment of the rest $R^\#$ at the protected carbonyl function,
(3) Reducing the nitro group to an amino group, wherein the rests $R^\#$ and $R^*$ have the meaning as defined herein.

The compounds according to general formula (I) described herein are especially suitable for the treatment and prophylaxis of coeliac disease as well as other diseases associated with transglutaminase 2.

Coeliac disease is also designated as coeliac sprue, non-tropical or endemic sprue, gluten-sensitive enteropathy, gluten intolerance or intestinal infantilism. Coeliac disease is characterized by intolerance to "gluten" leading to a chronic inflammation of the small intestine mucosa if the immune system is genetically predisposed.

Gluten is a protein gluten of prolamin and glutenin and is present in many types of cereals, such as wheat, bulgur (wheat variety), spelt (wheat variety), one-grain wheat (wheat variety), emmer (wheat variety), kamut (wheat variety), barley, unripe spelt grains (Grunkern), rye, triticale (hybrid between wheat and rye). Said types of cereals include proteins to an amount of about 7-15% wherein about 90% of the proteins are gluten. In the case of wheat, the prolamin is referred to as gliadin and in the case of rye as secalin, and in the case of barley as hordein.

Among the other diseases associated with transglutaminase 2 are eg fibroses, neurodegenerative diseases, cataract, acne, psoriasis, skin ageing, inflammations—particularly the gastrointestinal track—and candidosis.

These diseases are examples for indications which may be treated using the compounds described herein.

Furthermore, another aspect of the present invention comprises a pharmaceutical composition comprising at least one compound of the general formulas (I), (II), (III), (IV), (V), or (VI) and at least one pharmacologically acceptable carrier, adjuvant or solvent. The present invention relates further to pharmaceutical compositions which comprise further an active agent selected from the group comprising vitamins, monoclonal antibodies, immune modulators, inhibitors of inflammation, peptidases, and/or proteinases.

Thus the compounds of formula (I) described herein or according to the present invention may be administered themselves or in form of a pharmacologically effective salt.

Furthermore, the present invention relates to pharmaceutical compositions comprising at least one compound according to the general formula (I), (II), (III), (IV), (V), or (VI) and/or pharmaceutically acceptable salts thereof and at least one pharmacologically acceptable carrier, adjuvant or at least one pharmacologically acceptable solvent.

Furthermore, combination preparations with other active agents are possible, wherein the one or more additional active agent is mixed or administered in combination with at least one compound of the general formula (I), (II), (III), (IV), (V) or (VI) as described herein. Preferably, the transglutaminase inhibitors are used for supporting a gluten-free diet. Obviously, supplementary administration of vitamins, minerals and trace elements can be indicated, too. Also support of enzyme preparations in which, for example, prolyl endopeptidases or other peptidases are used is suitable. Moreover, combinations with antiphlogistics (steroidal and non-steroidal), T-cell silencers or cytokines or with monoclonal antibodies or "tight junctions" modulators can also be considered.

The pharmaceutical compositions are used in particular for the treatment and prophylaxis of coeliac disease and other diseases associated with transglutaminase 2 or caused by transglutaminase 2.

Furthermore, the compounds of the general formula (I), (II), (III), (IV), (V) or (VI) can be administered in form of their pharmaceutically active salts, optionally using essentially non-toxic pharmaceutically acceptable carriers, adjuvants or extenders. Medications are prepared in a known manner in a conventional solid or fluid carrier or in extenders and a conventional pharmaceutically acceptable adjuvant/expedient in a suitable dose.

The preferred preparations are provided in an administrable form suitable for oral application, such as pills, tablets, film tablets, coated tablets, capsules and powders.

Tablets, film tablets, coated tablets, gelatin capsules and opaque capsules are the preferred pharmaceutical formulations. Any pharmaceutical compositions contains at least one compound of the general formula (I), (II), (III), (IV), (V), or (VI) and/or pharmaceutically acceptable salts thereof in an amount of 5 mg to 500 mg, preferably 10 mg to 250 mg and most preferred in an amount of 10 to 100 mg per formulation.

Besides, the object of the present invention also includes pharmaceutical preparations for oral, parenteral, dermal, intradermal, intragastric, intracutaneous, intravascular, intravenous, intramuscular, intraperitoneal, intranasal, intravaginal, intrabuccal, percutaneous, rectal, subcutaneous, sublingual, topic, transdermal or inhalative application, containing, in addition to typical vehicles and extenders, a compound of the general formula (I), (II), (III), (IV) (V) or (VI) and/or a pharmaceutically acceptable salt thereof as active component.

The pharmaceutical compositions of the present invention contain one of the pyridinone derivatives disclosed herein as active component, typically mixed with suitable carrier materials, selected with respect to the intended form of administration, i.e. tablets to be administered orally, capsules (filled either with a solid, a semi-solid or a liquid), powders, orally administrable gels, elixirs, dispersible granulates, syrups, suspensions and the like in accordance with conventional pharmaceutical practices. For example, the pyridinone derivative can as active agent component be combined with any oral, non-toxic, pharmaceutically acceptable, inert carrier, such as lactose, starch, sucrose, cellulose, magnesium stearate, dicalcium phosphate, calcium sulfate, talc, mannitol, ethyl alcohol (liquid forms) and the like for the oral administration in form of tablets or capsules. Moreover, suitable binders, lubricants, disintegrants and colorants can be added to the mixture if required. Powders and tablets can consist of said inert carriers to an extent from about 5% per weight to about 95% per weight of the inventive composition.

Suitable binders include starch, gelatin, natural sugars, sweeteners made of corn, natural and synthetic gums, such as acacia gum, sodium alginate, carboxymethylcellulose, polyethylene glycol and waxes. Possible lubricants for the use in said dosage forms include boric acid, sodium benzoate, sodium acetate, sodium chloride and the like. Disintegrants include starch, methylcellulose, guar gum and the like. If required, sweeteners and flavor additives and preservatives can also be included. Some of the terms used above, namely disintegrants, extenders, lubricants, binders and the like are discussed in greater detail below.

Additionally, the compositions of the present invention can be formulated in a form with sustained release to provide a controlled release rate of any one or more components or active components, in order to optimize the therapeutic effect, i.e. the inhibitory activity and the like. Suitable dosage forms for sustained release include layered tablets containing layers with varying degradation rates or controlled release polymeric matrices impregnated with the active components and in the form of a tablet or capsule containing such impregnated or encapsulated porous polymeric matrices.

Preparations in fluid form include solutions, suspensions and emulsions. Exemplarily mentioned are water or water propylene glycol solutions for parenteral injections or the addition of sweeteners and opacifiers for oral solutions, suspensions and emulsions.

Aerosol preparations suitable for inhalation may include solutions and solids in the form of powders which can be combined with a pharmaceutically acceptable carrier, such as a compressed inert gas, e.g. nitrogen.

For the preparation of suppositories a low melting wax, such as a mixture of fatty acid glycerides, e.g. cocoa butter, is melted firstly and the active component is homogenously dispersed therein by stirring or similar mixing operations. The melted homogenous mixture is then poured in fitting forms, cooled and thus hardened.

Further preparations in solid form which are to be converted into preparations in fluid form for either oral or parenteral administration shortly before use are included. Such fluid forms include solutions, suspensions and emulsions.

Furthermore, the compounds of the present invention may be administered via transdermal application. The transdermal compositions can have the form of crèmes, lotions, aerosols and/or emulsions.

The term capsule refers to a special container or casing composed of methylcellulose, polyvinyl alcohols or denatured gelatins or starches, in which the active agents can be enclosed. Typically, hard shell capsules are prepared from mixtures of bones and porcine skin gelatins having comparatively high gel strength. The capsule itself can contain small amounts of colorants, opacifiers, softening agents and preservatives.

Tablet means a compressed or cast solid dosage form containing the active components with suitable extenders. The tablet can be produced by compressing mixtures or granulates obtained by wet granulation, dry granulation or compaction, which are known to the one skilled in the art.

Oral gels refer to the active components dispersed or solubilized in a hydrophilic semi-solid matrix.

Powders for compositions refer to powder mixtures containing the active components and suitable extenders which can be suspended in water or juices.

Suitable extenders are substances which usually form the largest part of the composition or dosage form. Suitable extenders include sugars such as lactose, sucrose, mannitol and sorbitol; starches derived from wheat, corn, rice and potatoes; and celluloses such as microcrystalline cellulose. The amount of extenders in the composition can range from about 5 to about 95% per weight of the total composition, preferably form about 25 to about 75% per weight and further preferred from about 30 to about 60% per weight.

The term disintegrants refers to materials added to the composition in order to support disintegration and release of the medicinal substance. Suitable disintegrants include starches, modified starches which are soluble in cold water, such as sodium carboxymethyl starch; natural and synthetic gums such as locust bean gum, caraya, guar gum, tragacanth and agar; cellulose derivatives such as methylcellulose and sodium carboxymethylcellulose, microcrystalline celluloses and crosslinked microcrystalline celluloses such as croscarmellose sodium; alginates such as alginic acid and sodium alginate; clays such as bentonites and foaming mixtures. The amount of disintegrants used in the composition can range from about 2 to 20% per weight of the composition and further preferred from about 5 to about 10% per weight.

Binders characterize substances binding or "gluing" powders to each other and they consequently serve as "glue" in the formulation. Binders add a cohesion starch which is already available in the extenders or the disintegrant. Suitable binders include sugar, such as sucrose; starches derived from wheat, corn, rice and potatoes; natural gums such as acacia gum, gelatin and tragacanth; derivatives of sea weed such as alginic acid, sodium alginate and ammonium calcium alginate, cellulose materials such as methyl cellulose and sodium carboxymethylcellulose and hydroxypropyl methylcellulose, polyvinylpyrrolidone and inorganic compounds, such as magnesium aluminum silicate. The amount of binders in the composition can range from about 2 to about 20% per weight of the total composition, preferably form about 3 to about 10% per weight and further preferred from about 3 to about 6% per weight.

The term lubricant refers to a substance added to the dosage form in order to allow for the tablet, granulate, etc. to be released from the casting mold or pressing mold, after compression, by reducing the friction. Suitable lubricants include metallic stearates such as magnesium stearate, calcium stearate or potassium stearate; stearic acid; waxes with high melting points and water soluble lubricants such as sodium chloride, sodium benzoate, sodium acetate, sodium oleate, polyethylene glycols and D,L-leucine. Due to the fact that lubricants have to be present on the surface of the granulates as well as between the granulates and parts of the tablet press they are typically added during the last step prior to compression. The amount of lubricants in the composition can range from about 0.2 to about 5% per weight of the total composition, preferably form about 0.5 to about 2% per weight and further preferred from about 0.3 to about 1.5% per weight.

Lubricants are materials preventing caking and improving the flow characteristics of granulates so that the flow is smooth and uniform. Suitable lubricants include silicon dioxide and talc. The amount of lubricants in the composition can range from about 0.1 to about 5% per weight of the total composition, preferably about 0.5; to about 2% per weight.

Colorants are adjuvants coloring the composition or dosage form. Such adjuvants can include colorants having food quality which are adsorbed on a suitable adsorption means, such as clay or aluminum oxide. The amount of the colorant used can vary from about 0.1 to about 5% per weight of the composition and preferably from about 0.1 to about 1% per weight.

As used herein, a "pharmaceutically effective amount" of a transglutaminase inhibitor is the amount or activity effective for achieving the desired physiological result, either in cells treated in vitro or in a patient treated in vivo. Specifically, a pharmaceutical effective amount is such an amount which is sufficient for inhibiting, for a certain period of time, one or more of the clinically defined pathological processes associated with transglutaminase 2. The effective amount can vary according to the specific pyridinone derivative and additionally depends on a plurality of factors and conditions related to the subject to be treated and the severity of the disease. If, for example, an inhibitor is to be administered in vivo, factors such as age, weight and health of the patients as well as dose reaction curves and data regarding toxicity obtained from preclinical animal studies are amongst the data to be considered. If the inhibitor in form of the pyridinone derivatives described herein is to be brought in contact with the cells in vivo, a plurality of preclinical in vitro studies would be designed in order to determine parameters such as absorption, half-life, dose, toxicity, etc. Determining a pharmaceutically effective amount for a given pharmaceutically active ingredient is part of the ordinary skills of the one skilled in the art.

DESCRIPTION OF THE FIGURES

FIG. 2 shows the synthesis scheme for the preparation of the pyridinone derivative 2a.

Figure 1:
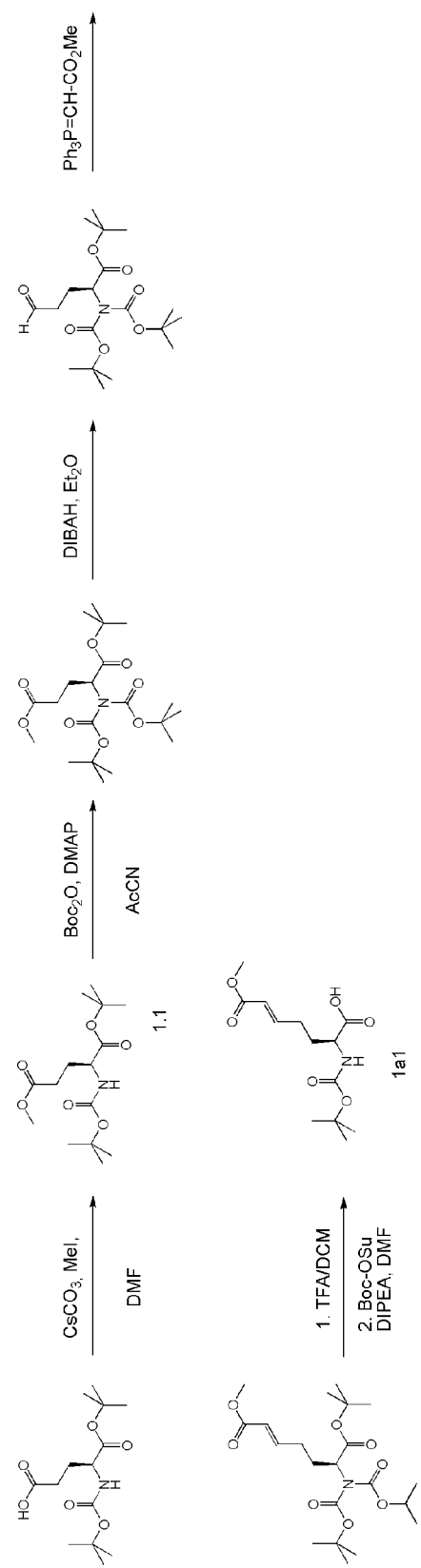
FIG. 1 shows the synthesis scheme for the preparation of the L-2-amino-hept-5-en-dicarboxylic acid derivative 1a1.
Figure 2:
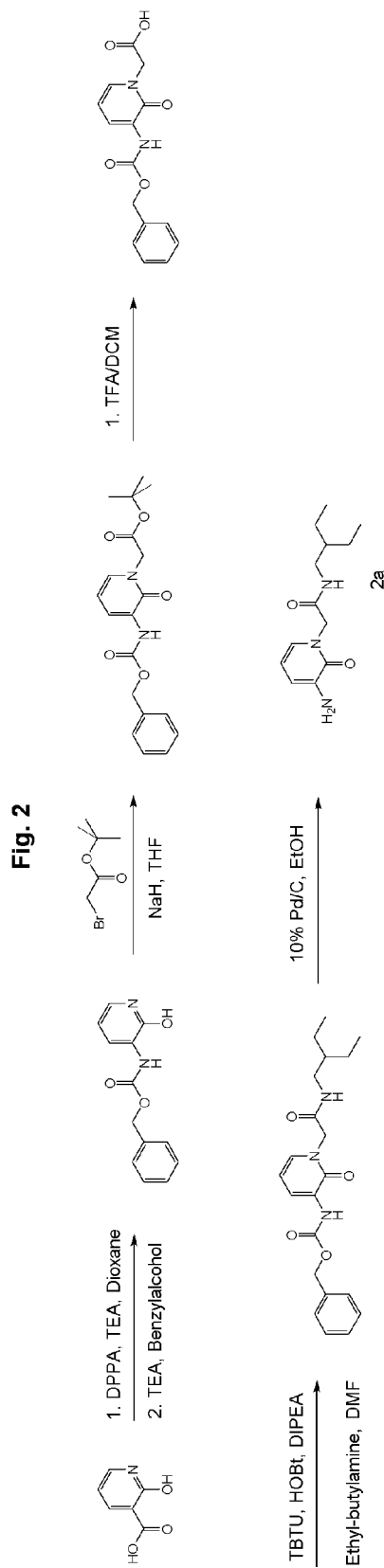
Figure 3:
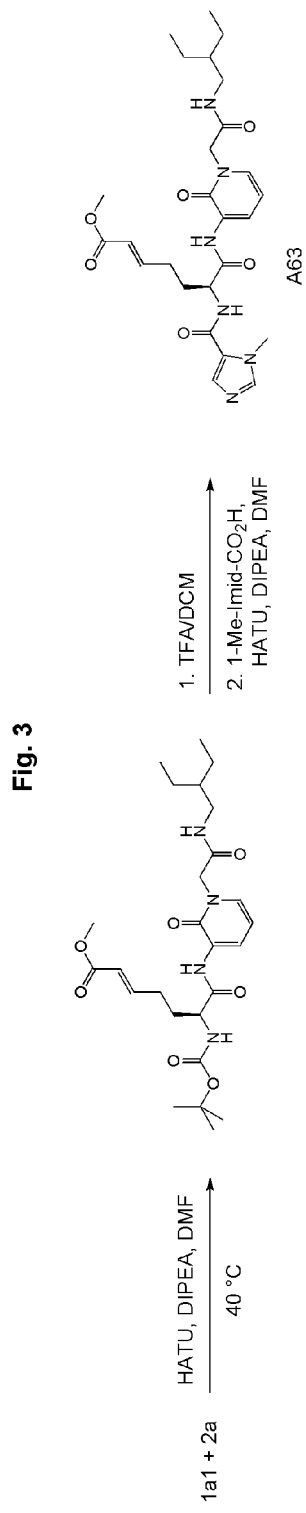
FIG. 3 shows the synthesis scheme for the preparation of the exemplar compound 63.

Following abbreviations have the following meaning within the FIGS. 1 to 3:
DMAP: 4-(Dimethylamino)-pyridine
DPPA: Diphenylphosphorylazide
TEA: Triethylamine
DMF: Dimethylformamide
ACN: Acetonitrile
TBTU: 0-(Benzotriazol-1-yl)-N,N,N',N'-tetramethyluroniumtetrafluoroborate
HOBt: 1-Hydroxybenzotriazole
DIPEA: N-Ethyldiisopropylamine
TFA: Trifluoroacetic acid

GENERAL DESCRIPTION OF SYNTHESIS

Design of Michael Acceptor System According to the Invention

Michael acceptors are olefins which are conjugated with at least one electron withdrawing substituent. For the design of such Michael acceptors, all reactions generating such an olefin are suitable. For example, but not limited for this purpose, alkenylation reactions of organometals, Corey-Winter reactions, Horner-Wadsworth-Emmons reactions, Knoevenagel reactions, Wittig reactions, Wittig-Horner reactions, Julia-Lytgoe reactions and Peterson olefinations would be stated. These and other olefination reactions are well known to the skilled person in the art. Especially preferred are the reactions in which an aldehyde reacts with a suitable substituted phosphonium ylide or a corresponding phosphonate (Wittig reaction, Wittig-Horner reaction, Horner-Wadsworth-Emmons reaction). Dragovich et al. show the broad application of these reaction types for design of Michael acceptor systems (Dragovich et al., J. Med. Chem., 1998, 41, 15, 2806-2818). The reagents required for this application are extensively commercially available (e.g. Sigam-Aldrich) or described in the literature. In the following, a general synthetic procedure for these olefination reactions is given. Specific execution examples are shown below.

It is started from a suitable substituted aldehyde, i.e. from an aldehyde of the general formula, wherein X is any residue:

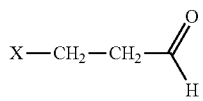

This aldehyde can be prepared exemplary from glutamic acid derivates.

One equivalent of phosphonium ylide (e.g. triphenyl phosphonium ylide) is dissolved in a suitable solvent (e.g. benzene, toluene or DMF) and deprotonated with a base (e.g. NaH, n-BuLi, NaNH$_2$). After the reaction, one equivalent of the respective aldehyde is added. After the reaction, the solvent is removed in vacuo and the obtained olefin is purified by chromatographic methods.

General Procedure 1:

General synthetic procedure for compounds with an alkoxycarbonylethenyl Michael system:

It is provided from amino acid Glu (glutamic acid) which is provide with protecting group at C-terminal and N-terminal as well as at the carboxyl function of side chain. As protecting group acid-labile protecting groups like, for example tert-butyloxycarbonyl, tert-butylester, methylester or 2-phenyl isopropylester can be used. By diisobutyl aluminum hydride the side chain is reduced selectively to aldehyde and after that reacted with a phosphorane to produce the Michael system. After acid-induced cleavage, for example by trifluoroacetic acid, of the protecting group, a pyridinone fragment is introduced at the C-terminal end with a peptidic bond. Subsequently, a side chain is introduced at the N-terminal end. This is preferably performed by an activated carboxylic acid, for example like active ester or acid anhydride. These reactions are universally applicable and well known to the person skilled in the art and a plurality of different residues can thus be added to the amino acid with the Michael system both at C- and N-terminal.

EXAMPLES

The following examples are intended to illustrate the invention with selected compounds without limiting the protecting scope of the present intellectual property right on these concrete examples. It is clear for a person skilled in the art that analogous compounds and compounds produced according to analogous synthetic ways fall under the protecting scope of the present intellectual property right.

1. Preparation of Example Compound A63 (ZED1227)

1.1 Preparation of 6-amino-hept-2-en-dicarboxyl acid derivatives (S)-1-tert-Butyl 5-methyl 2-(tert-butoxycarbonylamino)pentanedioate

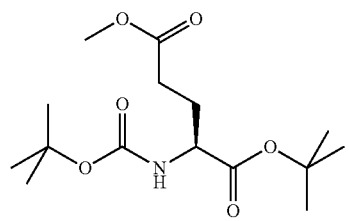

Molecular formula: C15H27NO6
Molecular weight: 387.47

12.0 g of Boc-Glu-OtBu (39.6 mmol) are dissolved in 200 mL of DMF. Under argon atmosphere, 7.09 g of cesium carbonate (21.8 mmol, 0.55 eq.) are added and the resulting suspension is stirred for 1 hour at RT. After this time, 2.47 mL of methyl iodide (39.6 mmol) are added and stirred at RT overnight. The solvent is removed in vacuo and the obtained residue is taken up in 400 mL of ethyl acetate. The undissolved solid is filtered and the filtrate is washed with respectively 75 mL of 10% citric acid, 10% NaHCO$_3$ solution and brine 3 times. After drying of the organic phase over Na$_2$SO$_4$ the solvent is removed in vacuo. The product is obtained as yellow oil. The product can be used without further purification in the following reaction.

Yield: 13.4 g, >100%
ESI-MS: 340.2 [M+Na]$^+$
Alternatively:
2.3 g of N-tert-butyloxycarbonyl-L-glutamic acid-1-tert-butylester (7.58 mmol) are dissolved in 80 mL of methanol and a fresh prepared diazomethane solution (23 mmol Diazald®) is dropped into this solution at RT. After 1 hour, the solvent is removed in vacuo. The purification of the compound is performed by chromatography on silica gel (column: 18.5*4 cm, DCM/MeOH=99/1, R$_f$=0.99)
Yield: 1.3 g (S)-1-tert-Butyl 5-methyl 2-(bis(tert-butoxycarbonyl)amino)pentanedioate

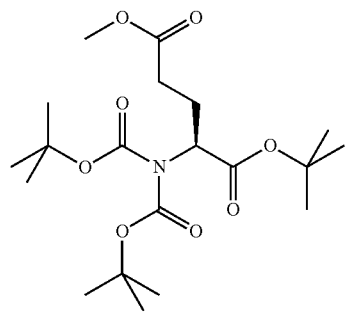

Molecular formula: C20H35NO8
Molecular weight: 417.49

13.4 g of Boc-Glu(OMe)-OtBu (~39.6 mmol) are dissolved in 30 mL of acetonitrile and treated with 986 mg of DMAP (7.91 mmol, 0.2 eq). Under nitrogen atmosphere a solution of 17.6 g of di-tert-butylbicarbonate (77.1 mmol, 2 eq) in 100 mL of acetonitrile is added. After stirring overnight, the solvent is removed in vacuo and the obtained crude product is purified by chromatography on silica gel (column: 31*6.0 cm, petroleum ether/ethyl acetate 9:1)

Column chromatography: collected in 250 mL fractions, product: fractions 6-13

TLC control: petroleum ether/ethyl acetate 8:2, $R_f$=0.70

Yield: 13.7 g, 32.8 mmol, 83%

ESI-MS: 440.3 [M+Na]$^+$ (S)-tert-Butyl 2-(bis(tert-butoxycarbonyl)amino)-5-oxopentanoate

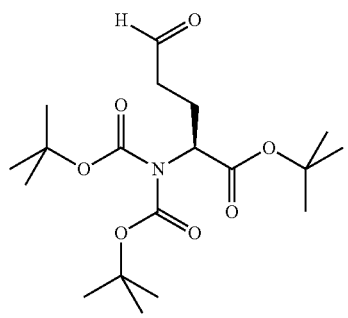

Molecular formula: C19H33NO7
Molecular weight: 387.47

13.7 g of Boc$_2$-Glu(OMe)-OtBu (32.8 mmol) are dissolved in 200 mL of absolute diethylether and cooled to −78° C. under argon atmosphere. At this temperature 36.1 mL (36.1 mmol, 1.1 eq) of a solution of diisobutyl aluminum hydride (1 M in hexane) is dropped slowly. After the addition, the solution is stirred for further 15 min at −78° C., before the reacting mixture is quenched by addition of 50 mL of water at the same temperature. With vigorous stirring, it is warmed up to RT and the cloudy solution is filtered over Celite. The filtrate is concentrated in dryness and the residual water is removed by codestillation with toluene. Light-colored oil is obtained and it is used without further purification in the subsequent reaction.

TLC control: petroleum ether/ethyl acetate 8:2, $R_f$=0.54

Yield: 13.3 g, >100% (purity 86.1%)

500-MHz-$^1$H-NMR-cosy (DMSO$_{d6}$): δ [ppm]=9.65 (s, 1H, H-4), 4.63 (dd, 1H, H-1, $J_{1/2a}$=4.8 Hz, $J_{1/2b}$=9.85 Hz), 2.51-2.50 (m, 1H, H-3$_a$), 2.48-4.40 (m, 1H, H-3$_b$), 2.27-2.20 (m, 1H, H-2a), 1.98-1.91 (m, 1H, H-2$_b$), 1.44 (s, 18H, 6*CH$_3$(Boc)), 1.92 (s, 9H, 3*CH$_3$(O-tBu))

ESI-MS: 410.4 [M+Na]$^+$ (S,E)-7-tert-Butyl 1-methyl 6-(bis(tert-butoxycarbonyl)amino)hept-2-enedioate

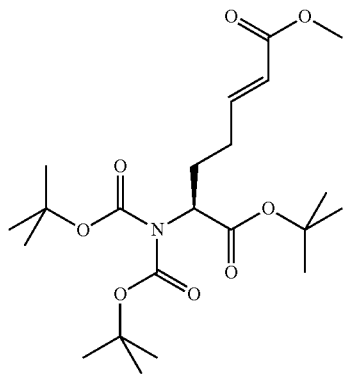

Molecular formula: C22H37NO8
Molecular weight: 443.53

13.2 g of Boc$_2$-Glu(H)—OtBu (~32.8 mmol) are provided in 20 mL of dried benzene and under argon atmosphere at RT a solution of 11.2 g of (methoxycarbonylmethylen)-triphenyl-phosphorane (32.8 mmol) is added. After stirring overnight, the solvent is removed in vacuo and the obtained oily residue is purified by chromatography on silica gel (column: 39*6.0 cm, petroleum ether/ethyl acetate 9:1).

Column chromatography: collected in 250 mL fractions, product: fractions 2-12

TLC control: petroleum ether/ethyl acetate 8:2, $R_f$=0.54

Yield: 12.0 g, 27.1 mmol, 83%

500-MHz-$^1$H-NMR-cosy (DMSO$_{d6}$): δ [ppm]=6.66 (dt, 1H, H-4, $J_{4/3}$=6.8 Hz $J_{4/5}$=15.9 Hz), 5.64 (d, 1H, H-5, $J_{5/4}$=15.9 Hz), 4.45-4.2 (m, 1H, H-1), 3.44 (s, 3H, CH$_3$-6), 2.01-1.95 (m, 2-H, H-3$_a$, H-3$_b$), 1.95-1.86 (m, 1H, H-2$_a$), 1.78-1.67 (m, 1H, H-2$_b$), 1.24 (s, 18H, 6*CH$_3$(Boc)), ESI-MS: 466.3 [M+Na]$^+$ (S,E)-2-(tert-Butoxycarbonylamino)-7-methoxy-7-oxohept-5-enoic acid (1a1)

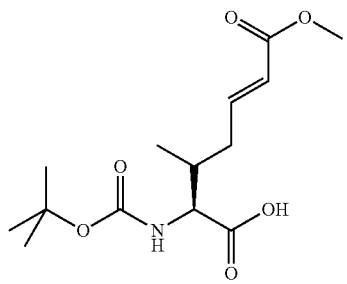

Molecular formula: C13H21NO6
Molecular weight: 287.31

7.0 g of (S,E)-7-tert-butyl 1-methyl 6-(bis(tert-butoxycarbonyl)amino)hept-2-enedioate (15.8 mmol) are dissolve in 40 mL of dichloromethane and added into the solution of 70 mL of trifluoroacetic acid. It is stirred at RT for 4 h. The solvent is removed in vacuo and the green residue is dried under high vacuum. The obtained oil is further used without purification. By successive addition of DIPEA the pH value is adjusted to ca. 7. The oil is taken up in 50 mL of DMF and treated with 5.37 mL of DIPEA. 4.08 g of Boc-OSu (18.9 mmol, 1.2 eq) are added and stirred at RT overnight. The solvent is removed in vacuo and the residue is suspended in 130 mL of 5% $KHSO_4$ solution. It is extracted with ethyl acetate (1×150 mL, 2×100 mL) and the corrected organic phases are washed with brine (75 mL). After drying of the organic phase over $Na_2SO_4$ the solvent is removed in vacuo. The residue is purified by chromatography on silica gel (column: 13*6.0 cm, toluene/ethyl acetate 65:35, 0.5% acetic acid). Colorless oil is obtained.

Column chromatography: collected in 200 mL fractions, product: fractions 2-5, first running 500 mL TLC control: toluene/ethyl acetate 1:1, 0.5% acetic acid, $R_f$=0.35

Yield: 4.04 g, 14.1 mmol, 89% (purity 88.6%)

ESI-MS: 310.1 $[M+Na]^+$ 1.2 Preparation of Pyridinone Derivatives

Variant A

Benzyl-3-hydroxypyridin-3-yl-carbamate

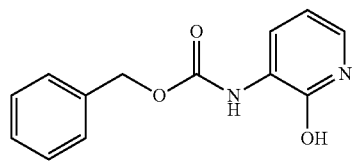

Molecular formula: C13H12N2O3
Molecular weight: 244.25

15 g of 2-hydroxy-nicotinic acid (108 mmol) are suspended in 180 mL of dried dioxane. After addition of 14.9 mL of triethylamine (108 mmol), the suspension is clear extensively. 24 mL of diphenyl phosphoryl azide (DPPA, 108 mmol) are added and the reaction solution is refluxed (130° C.) under argon atmosphere. Thereby, a gas emission is observed. After 16 h, further 16.3 mL of TEA and 12.8 mL of benzyl alcohol (117 mmol, 1.1 eq) are added successively and refluxed for further 24 h. The solvent is removed in vacuo and the obtained brown residue is taken up in a mixture of 300 mL of DCM and 300 mL of brine. By 1M HCl solution the pH value is adjusted to ca. 1 (ca. 22 mL), the phases are separated and subsequently the water phase is extracted two times with each 200 mL of DCM. The corrected organic phases are washed with 10% $NaHCO_3$ solution (3×150 mL) and brine (1×150 mL), dried over $Na_2SO_4$, filtered and concentrated in vacuo in dryness. The obtained brown solid is recrystallized from 300 mL of methanol.

TLC control: DCM/MeOH 9:1, $R_f$=0.70

Yield: 16.2 g, 66.4 mmol, 62% (pale brown, felt-like solid)

ESI-MS: 245.1 $[M+H]^+$ tert-Butyl 2-(3-(benzyloxycarbonylamino)-2-oxopyridin-1(2H)-yl)acetate

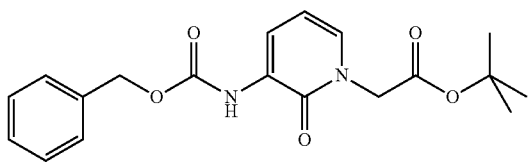

Molecular formula: C19H22N2O5
Molecular weight: 358.59

16.2 g of benzyl-3-hydroxypyridin-3-yl-carbamate (66.4 mmol) are suspended in 900 mL of absolute THF and cooled to 0° C. under argon atmosphere and 2.92 g of NaH (60% in mineral oil, 73.1 mmol, 1.1 eq) are added. To the resulting solution after the end of gas emission (ca. 15 min) 13.7 mL of bromoacetic acid tert-butylester (89.7 mmol, 1.35 eq) are added. It is stirred still for 15 minutes at 0° C. and subsequently at RT overnight. The reaction mixture is filtered and the filtrate is concentrated in dryness. The residue is taken up in 5 mL of ethyl acetate and treated with ca. 50 mL of diethylether and the resulting suspension is precipitated in the refrigerator overnight. The crystals are filtered off and washed with a little amount of ether.

The filtrate is concentrated and purified by chromatography on silica gel. (bed: 20×6 cm, eluent: petroleum ether/ethyl acetate=8/2)

Column chromatography: collected in 250 mL fractions, product: fractions 10-25 TLC control: petroleum ether/ethyl acetate=7/3, $R_f$=0.46

Yield: 19.3 g, 54.0 mmol, 81%

ESI-MS: 359.1 $[M+H]^+$ 2-(3-(Benzyloxycarbonylamino)-2-oxopyridin-1(2H)-yl)acetic acid

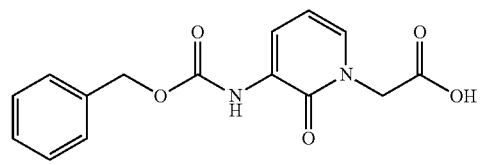

Molecular formula: C15H14N2O5
Molecular weight: 302.28

4.00 g of tert-butyl 2-(3-(benzyloxycarbonylamino)-2-oxopyridin-1(2H)-yl)acetate (11.2 mmol) are dissolved in 50 mL of dichloromethane and treated with 50 mL of trifloroacetic acid. It is stirred at RT for 3 h, before the volatile components are removed in vacuo. After drying under high vacuum a brown solid is obtained and it is suitable for the further use without purification.

Yield: 3.70 g, >100%

ESI-MS: 303.2 $[M+H]^+$

Benzyl-1-(2-(2-ethylbutylamino)-2-oxoethyl)-2-oxo-1,2-dihydropyridin-3-ylcarbamate

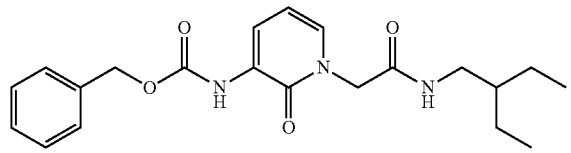

Molecular formula: C21H27N3O4
Molecular weight: 385.46

A mixture of 3.70 g of 2-(3-(benzyloxycarbonylamino)-2-oxopyridin-1(2H)-yl)acetic acid (~11.2 mmol), 3.58 g of TBTU (11.2 mmol), 1.51 g of HOBt (11.2 mmol) is dissolved in 60 mL of DMF. By addition of 5.70 mL of DIPEA (33.5 mmol, 3 eq) a pH value is adjusted to ~10. 1.50 mL of 2-ethyl-butylamine (11.2 mmol) is added and the mixture is stirred at RT overnight. The solvent is removed in vacuo and the obtained residue is taken up in 300 mL of DCM and subsequently washed with 10% citric acid (3×75 mL), saturated NaHCO₃ solution (3×75 mL) and brine (75 mL). The organic phase is dried over Na₂SO₄, filtered and concentrated in dryness. Pale brown solid is obtained and it is suitable for further processing without further purification.

Yield: 5.22 g, >100%
ESI-MS: 386.3 [M+H]⁺

2-(3-Amino-2-oxopyridin-1(2H)-yl)-N-(2-ethylbutyl)acetamide (2a)

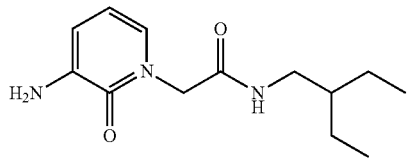

Molecular formula: C13H21N3O2
Molecular weight: 251.32

5.22 g of benzyl-1-(2-(2-ethylbutylamino)-2-oxoethyl)-2-oxo-1,2-dihydropyridin-3-yl-carbamate (2.4, ~11.2 mmol) are dissolved under nitrogen atmosphere in 60 mL of methanol. To this solution, 500 mg of Pd/C (10%) are added and stirred under hydrogen atmosphere at atmosphere pressure for 2.5 h. The catalysis is separated by filtration over silica gel, before the solvent is removed in vacuo. Dark oil is obtained and it is suitable for further processing without further purification.

Yield: 3.62 g, >100%
ESI-MS: 252.2 [M+H]⁺

Variant B tert-Butyl 2-(3-nitro-2-oxopyridin-1(2H)-yl)acetate

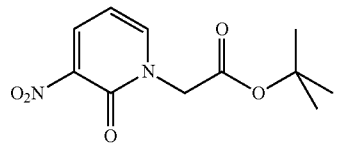

Molecular formula: C11H14N2O5
Molecular weight: 254.24

3.00 g (21.0 mmol) of 2-hydroxy-3-nitropyridine are suspended in 175 mL of THF (argon atmosphere) and 923 mg (23.1 mmol, 1.1 eq) of NaH (60%) is slowly added at 0° C. After 30 min-stirring at 0° C., 4.24 mL (28.3 mmol, 1.35 eq) of tert-butyl bromoacetate are dropped and stirred overnight at RT. The solution is poured into 300 g of ice and the THF-portion is removed in vacuo. The residue is extracted with ethyl acetate (2×200 mL), the organic phase is dried over sodium sulfate and the solvent is removed in vacuo (column:41*6.0 cm, petroleum ether/ethyl acetate 1:9).

Column chromatography: collected in 50 mL fractions, product: fractions 7-16
TLC control: ethylacetate, $R_f$=0.72
Yield: 3.73 g, 14.7 mmol, 70%
ESI-MS: 255.1 [M+H]⁺

2-(3-Nitro-2-oxopyridin-1(2H)-yl)acetic acid

Molecular formula: C7H6N2O5
Molecular weight: 198.13

3.73 g (14.7 mmol) of tert-butyl 2-(3-nitro-2-oxopyridin-1(2H)-yl)acetate are dissolved in 10 mL of dichloromethane and treated with 40 mL of trifluoroacetic acid. It is stirred at RT for 3 h, before the volatile components are removed in vacuo. The product is further used without purification.

Yield: 3.05 g, >100%
ESI-MS: 199.0 [M+H]⁺

N-(2-Ethylbutyl)-2-(3-nitro-2-oxopyridin-1(2H)-yl)acetamide

Molecular formula: C13H19N3O4
Molecular weight: 281.31

The crude product 2-(3-nitro-2-oxopyridin-1(2H)-yl)acetic acid (~14.7 mmol), 4.71 g (14.7 mmol) of TBTU, 1.98 g (14.7 mmol) of HOBT and 4.99 mL (29.3 mmol, 2 eq) of DIPEA are dissolved in 60 mL of DMF (argon atmosphere). 1.97 mL (14.7 mmol) of 2-ethyl-butylamine ((→pH=6) and another eq DIPEA (→pH=8) are added. After 1 h a half eq DIPEA is further titrated and stirred overnight at RT. If the TLC control shows incomplete conversion, it is stirred for further 3 h at 45° C. The solvent is removed in vacuo and the residue is taken up in 500 mL of DCM/MeOH (8/2). It is subsequently washed with 10% citric acid (3×100 mL), saturated NaHCO$_3$ solution (3×100 mL) and brine (75 mL). The organic phase is dried over sodium sulfate and the solvent is removed in vacuo. The crude product (3.5 g) is treated with 10 mL of ethyl acetate, 30 mL of PE (40-60) is added and stirred for 15 min at RT. The solid is filtered off, washed with some amount of PE and dried.

Yield: 2.90 g, 10.9 mmol, 70%
ESI-MS: 282.2 [M+H]$^+$ 2-(3-amino-2-oxopyridin-1(2H)-yl)-N-(2-ethylbutyl)acetamide

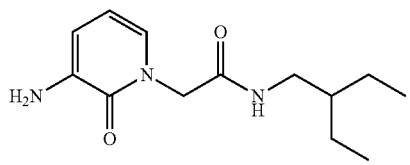

Molecular formula: C13H21N3O2
Molecular weight: 251.32

100 mg (0.36 mmol) of N-(2-ethylbutyl)-2-(3-nitro-2-oxopyridin-1(2H)-yl)acetamide are suspended under nitrogen atmosphere in 7 mL of methanol. To this solution 10 mg of Pd/C (10%) is added and stirred under hydrogen atmosphere at atmosphere pressure for 2 h at RT. The catalysis is separated by filtration over silica gel, before the solvent is removed in vacuo. Green-gray solid is obtained and it is suitable for further processing without purification.

Yield: 92 mg, >100%
ESI-MS: 252.2 [M+H]$^+$ 1.3 Preparation of Pyridinone Inhibitors (S,E)-Methyl 6-(tert-butoxycarbonylamino)-7-(1-(2-(2-ethylbutylamino)-2-oxoethyl)-2-oxo-1,2-dihydropyridin-3-ylamino)-7-oxohept-2-enoate

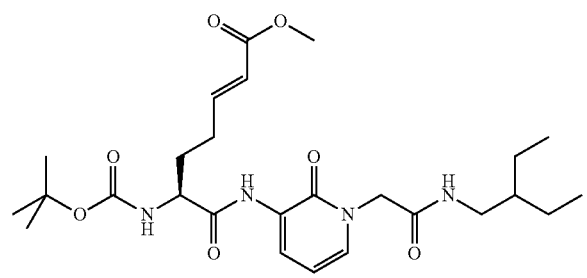

Molecular formula: C26H40N4O7
Molecular weight: 520.62

A solution of 3.36 g of 2-(3-amino-2-oxopyridin-1(2H)-yl)-N-(2-ethylbutyl)acetamide (2a, ~10.4 mmol) in 20 mL of DMF is provided. To this solution, a solution of 2.97 g of (S,E)-2-(tert-butoxycarbonylamino)-7-ethoxy-7-oxohept-5-enoic acid (1a1, 10.4 mmol), 3.93 g of HATU (10.4 mmol) and 3.52 mL of DIPEA (20.7 mmol, 2 eq) in 40 mL of DMF is added. By successive addition of DIPEA the pH value is adjusted to ca. 7. The reaction mixture is stirred at 40° C. for 2.5 hours, as well as at RT overnight, before the solvent is removed in vacuo. The obtained brown residue is taken up in 250 mL of ethyl acetate and subsequently washed with 10% citric acid (3×75 mL), saturated NaHCO$_3$ solution (3×75 mL) and brine (75 mL). The organic phase is dried over Na$_2$SO$_4$ and concentrated in vacuo in dryness. The residue is purified by chromatography on silica gel (bed: 13×6 cm, eluent: toluene/acetone=7/3).

Column chromatography: 150 mL first running, corrected in 40 mL fractions, product: fraction 6-15
TLC control: DCM/MeOH=97/3, R$_f$=0.40
Yield: 3.34 g, 6.42 mmol, 62%
ESI-MS: 543.4 [M+Na]$^+$ (S,E)-Methyl 7-(1-(2-(2-ethylbutylamino)-2-oxoethyl)-2-oxo-1,2-dihydropyridin-3-ylamino)-6-(1-methyl-1H-imidazole-5-carboxamido)-7-oxohept-2-enoate A63 (ZED1227)

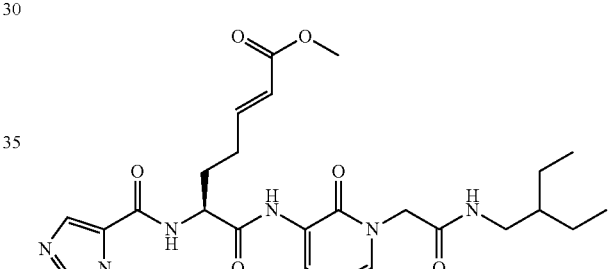

Molecular formula: C26H36N6O6
Molecular weight: 528.60

3.14 g of (S,E)-methyl 6-(tert-butoxycarbonylamino)-7-(1-(2-(2-ethylbutylamino)-2-oxoethyl)-2-oxo-1,2-dihydropyridin-3-ylamino)-7-oxohept-2-enoate (3.1, 6.03 mmol) are dissolved in a mixture of 25 mL of dichloromethane and 35 mL of TFA and stirred for 3 hours at RT, before the volatile components are removed in vacuo. The obtained brown oil is dried under high vacuum and dissolved in 10 mL of DMF and 1.03 mL of DIPEA (6.03 mmol) is added. To this a solution of 2.29 g of HATU (6.03 mmol) and 1.03 mL of DIPEA (6.03 mmol) in 30 mL of DMF is added. By successive addition of DIPEA the pH value is adjusted to ca. 7. It is stirred overnight at RT. The residue is taken up in 200 mL of ethyl acetate and subsequently washed with 10% citric acid, saturated NaHCO$_3$ solution and brine (each 75 mL). The organic phase is dried over Na$_2$SO$_4$, filtered and concentrated in vacuo in dryness. The residue is purified by chromatography on silica gel (bed: 12×6 cm, eluent: DCM/MeOH=97/3, after 2 Liters 95/5).

Column chromatography: 1000 mL first running, corrected in 50 mL fractions, product: fraction 43-66
TLC control: DCM/MeOH=97/3, R$_f$=0.30
Yield: 1.42 g, 2.69 mmol, 45%
ESI-MS: 551.3 [M+Na]$^+$ ¹H-NMR (DMSO-d6, 500 MHz): δ [ppm]=9.29 (s, 1H), 8.63 (d, 1H), 8.21 (dd, 1H), 8.04 (t, 1H), 7.75 (d, 2H), 7.33 (dd, 1H), 6.93 (dt, 1H, J=15.63; 6.93), 6.25 (t, 1H), 5.86 (d, 1H, J=15.69), 4.58 (s, 2H), 3.79 (s, 3H), 3.62 (s, 3H), 3.01 (t, 2H), 2.33 (m, 2H), 2.03 (m, 1H), 1.90 (m, 1H), 1.26 (m, 5H), 0.83 (t, 6H)

2. Preparation of Example Compound A29 (ZED1098)

Benzyl 1-(2-(isopentylamino)-2-oxoethyl)-2-oxo-1,2-dihydropyridin-3-ylcarbamate (ZED1020)

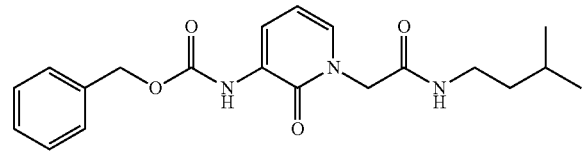

Molecular formula: C20H25N3O4
Molecular weight: 371.43

A mixture of 900 mg of 2-(3-(benzyloxycarbonylamino)-2-oxopyridin-1(2H)-yl)acetic acid (~2.32 mmol), 744 mg of TBTU (2.32 mmol), 313 mg of HOBt (2.32 mmol) is dissolved in 25 mL of DMF. By addition of 985 μL of DIPEA (5.79 mmol, 2.5 eq) a pH value is adjusted to ~9. 539 μL of isopentylamine (4.63 mmol) is added and the mixture is stirred at RT for 2.5 h. The solvent is removed in vacuo and the obtained residue is taken up in 100 mL of DCM and subsequently washed with 10% citric acid (3×75 ml), saturated NaHCO₃ solution (3×75 ml) and brine (75 mL). The organic phase is dried over Na₂SO₄, filtered and concentrated in vacuo in dryness. Brown solid is obtained and it is suitable for further processing without purification.
Yield: 573 mg, 1.54 mmol, 67%
ESI-MS: 372.3 [M+H]⁺

2-(3-Amino-2-oxopyridin-1(2H)-yl)-N-isopentylacetamide (ZED1022)

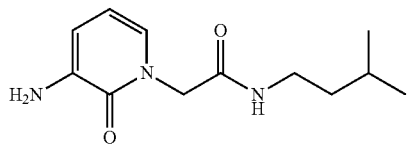

Molecular formula: C12H19N3O2
Molecular weight: 237.30

573 mg of benzyl 1-(2-(isopentylamino)-2-oxoethyl)-2-oxo-1,2-dihydropyridin-3-ylcarbamate (ZED1020, 1.54 mmol) are dissolved under nitrogen atmosphere in 100 mL of ethanol. To this solution 50 mg of Pd/C (10%) is added and stirred under hydrogen atmosphere at atmosphere pressure for 1 h at RT. The catalysis is separated by filtration over silica gel, before the solvent is removed in vacuo. Green solid is obtained and it is suitable for further processing without purification.
Yield: 381 mg, >100%
ESI-MS: 238.3 [M+H]⁺

(S,E)-methyl 6-(tert-butoxycarbonylamino)-7-(1-(2-(isopentylamino)-2-oxoethyl)-2-oxo-1,2-dihydropyridin-3-ylamino)-7-oxohept-2-enoate (ZED1096)

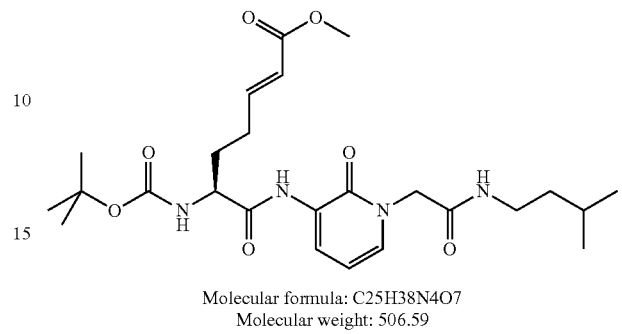

Molecular formula: C25H38N4O7
Molecular weight: 506.59

A solution of 381 mg of 2-(3-amino-2-oxopyridin-1(2H)-yl)-N-isopentylacetamide (ZED1022, ~1.54 mmol) in 5 mL of DMF is provided. To this solution, a solution of 443 mg of (S,E)-2-(tert-butoxycarbonylamino)-7-ethoxy-7-oxohept-5-enoic acid (1a1, 1.54 mmol), 586 mg of HATU (1.54 mmol) and 524 μL of DIPEA (3.08 mmol, 2 eq) in 5 mL of DMF is added. By successive addition of DIPEA the pH value is adjusted to ca. 7. The reaction mixture is stirred at 40° C. for 2.5 hours, as well as at RT overnight, before the solvent is removed in vacuo. The obtained residue is taken up in 75 mL of ethyl acetate and subsequently washed each three times with 10% citric acid, saturated NaHCO₃ solution and brine. The organic phase is dried over Na₂SO₄, filtered and concentrated in vacuo in dryness. The bluish residue is further processed without purification.
Yield: 556 mg, 1.10 mmol, 72%
ESI-MS: 507.3 [M+H]⁺

(S,E)-methyl 6-acetamido-7-(1-(2-(isopentylamino)-2-oxoethyl)-2-oxo-1,2-dihydropyridin-3-ylamino)-7-oxohept-2-enoate (A29) (ZED1098)

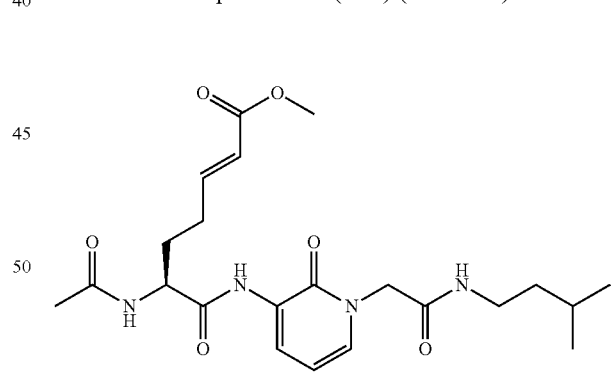

Molecular formula: C22H32N4O6
Molecular weight: 448.51

556 mg of (S,E)-methyl 6-(tert-butoxycarbonylamino)-7-(1-(2-(isopentylamino)-2-oxoethyl)-2-oxo-1,2-dihydropyridin-3-ylamino)-7-oxohept-2-enoate (ZED1096, 1.10 mmol) are dissolved in a mixture of 15 mL of dichloromethane and 15 mL of TFA and stirred for 1 h at RT, before the volatile components are removed in vacuo. The obtained oil is dried under high vacuum and dissolved in 20 mL of DMF and 412 μL of DIPEA (2.42 mmol) as well as 125 μL of acid anhydride (1.32 mmol) are added. By successive addition of DIPEA the pH value is adjusted to ca. 7. It is stirred for 3 h at RT, before the solvent is removed in vacuo. The residue is purified by preparative HPLC (35% ACN in water, 50 mL/min, gradient 1% pro min).

Yield: 238 mg, 0.53 mmol, 48%

471.4 [M+Na]+

$^1$H-NMR (DMSO-d6, 500 MHz): δ [ppm]=9.22 (s, 1H), 8.35 (d, 1H), 8.18 (dd, 1H), 8.11 (t, 1H), 7.75 (d, 1H), 7.32 (dd, 1H), 6.90 (dt, 1H, J=15.64; 6.85), 6.24 (t, 1H), 5.85 (d, 1H, J=15.64), 4.58 (s, 2H), 4.41 (m, 1H), 3.63 (s, 3H), 3.09 (t, 2H), 2.27 (m, 2H), 1.90 (m, 1H), 1.89 (s, 3H), 1.73 (m, 1H), 1.59 (m, 1H), 1.31 (m, 2H), 0.86 (d, 6H)

3. Preparation of Example Compound (A61) (ZED1219)

tert-Butyl 2-(3-amino-2-oxopyridin-1(2H)-yl)acetate (ZED1095)

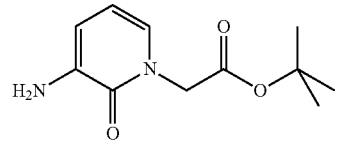

Molecular formula: C11H16N2O3
Molecular weight: 224.26

2.00 g of tert-butyl 2-(3-(benzyloxycarbonylamino)-2-oxopyridin-1(2H)-yl)acetate are dissolved under nitrogen atmosphere in 70 mL of ethanol. To this solution 200 mg of Pd/C (10%) is added and stirred under hydrogen atmosphere at atmosphere pressure for 1.5 h at RT. The catalysis is separated by filtration over silica gel, before the solvent is removed in vacuo. The crude product is used for further processing without purification.

Yield: 1.35 g, >100%

ESI-MS: 225.1 [M+H]+

(S,E)-Methyl 7-(1-(2-tert-butoxy-2-oxoethyl)-2-oxo-1,2-dihydropyridin-3-yl-amino)-6-(tert-butoxycarbonylamino)-7-oxohept-2-enoate (ZED1209)

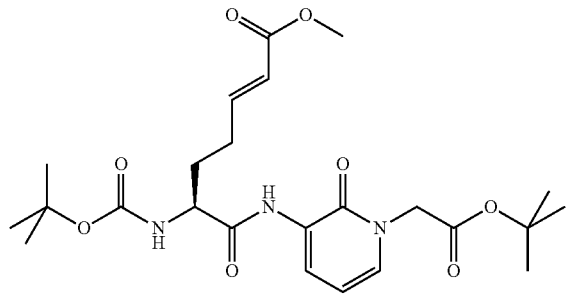

Molecular formula: C24H35N3O8
Molecular weight: 493.55

A solution of 292 mg of tert-butyl 2-(3-amino-2-oxopyridin-1(2H)-yl)acetate (ZED1095, 1.30 mmol) in 5 mL of DMF is provided. To this solution, a solution of 2.97 g of (S,E)-2-(tert-butoxycarbonylamino)-7-ethoxy-7-oxohept-5-enoic acid Oat 1.30 mmol), 494 mg of HATU (1.30 mmol) and 442 µL of DIPEA (2 eq) in 5 mL of DMF is added. By successive addition of DIPEA the pH value is adjusted to ca. 7. The reaction mixture is stirred at RT overnight, before the solvent is removed in vacuo. The obtained residue is taken up in 75 mL of ethyl acetate and subsequently washed each three times with 10% citric acid, saturated NaHCO$_3$ solution and brine. The organic phase is dried over Na$_2$SO$_4$, filtered and concentrated in vacuo in dryness. Blue gel is obtained and it is suitable for further processing without further purification.

Yield: 590 mg, 1.20 mmol, 92%

ESI-MS: 494.2 [M+H]+

(S,E)-2-(3-(2-(tert-butoxycarbonylamino)-7-methoxy-7-oxohept-5-enamido)-2-oxopyridin-1(2H)-yl)acetic acid (ZED1211)

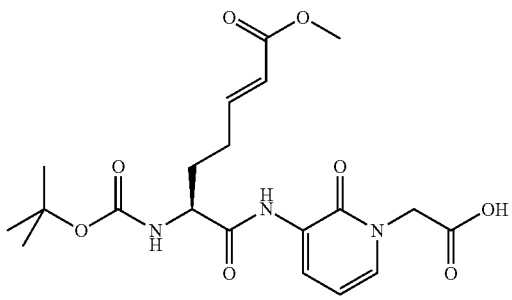

Molecular formula: C20H27N3O8
Molecular weight: 437.44

590 mg of (S,E)-methyl 7-(1-(2-tert-butoxy-2-oxoethyl)-2-oxo-1,2-dihydropyridin-3-yl-amino)-6-(tert-butoxycarbonylamino)-7-oxohept-2-enoate (ZED1209, 1.20 mmol) are dissolved in 10 mL of dichloromethane and to this solution 10 mL of trifluoroacetic acid is added. It is stirred at RT for 1 h. The solvent is removed in vacuo and the residue is dried under high vacuum. The obtained oil is further reacted without purification. The oil is taken up in 15 mL of DMF and treated with 173 µL of DIPEA. By successive addition of DIPEA the pH value is adjusted to ca. 7. To this solution, 285 mg of Boc-OSu (1.1 eq) are added and stirred at RT overnight. The solvent is removed in vacuo and the residue is purified by preparative HPLC (30% ACN in water, 8 mL/min, gradient 1% pro min).

Yield: 201 mg, 0.46 mmol, 38%

ESI-MS: 438.2 [M+H]+

(S,E)-methyl 7-(1-(2-(((2S,3R)-1-tert-butoxy-3-methyl-1-oxopentan-2-ylamino)-2-oxoethyl)-2-oxo-1,2-dihydropyridin-3-ylamino)-6-(tert-butoxycarbonylamino)-7-oxohept-2-enoate (ZED1215)

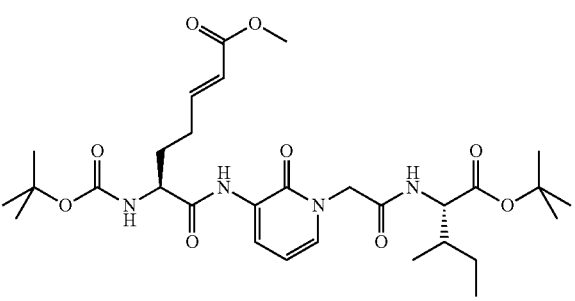

Molecular formula: C30H46N4O9
Molecular weight: 606.71

A solution of 129 mg of H-Ile-OtBu*HCl (0.58 mmol, 1.25 eq) in 4 mL of DMF is provided. To this solution, a solution of 201 mg of (S,E)-2-(tert-butoxycarbonylamino)-7-methoxy-7-oxohept-5-enamido)-2-oxopyridin-1(2H)-yl) acetic acid (ZED1211, 0.46 mmol), 129 mg of HATU (0.46 mmol) and 176 µL of DIPEA (2.25 eq) in 4 mL of DMF is added. By successive addition of DIPEA the pH value is adjusted to ca. 7. The reaction mixture is stirred at RT overnight, before the solvent is removed in vacuo. The obtained residue is taken up in 75 mL of ethyl acetate and subsequently washed each three times with 10% citric acid, saturated NaHCO₃ solution and brine. The organic phase is dried over Na₂SO₄, filtered and concentrated in vacuo in dryness. Oil is obtained and it is suitable for further processing without further purification.

Yield: 310 mg, >100%

ESI-MS: 607.3 [M+H]⁺

(2S,3R)-2-(2-(3-((S,E)-2-benzamido-7-methoxy-7-oxohept-5-enamido)-2-oxopyridin-1(2H)-yl)acetamido)-3-methylpentanoic acid (A61) (ZED1219)

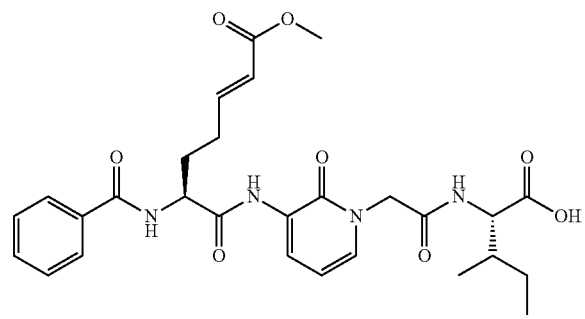

Molecular formula: C28H34N4O8
Molecular weight: 554.59

155 mg of (S,E)-methyl 7-(1-(2-((2S,3R)-1-tert-butoxy-3-methyl-1-oxopentan-2-ylamino)-2-oxoethyl)-2-oxo-1,2-dihydropyridin-3-ylamino)-6-(tert-butoxycarbonylamino)-7-oxohept-2-enoate (ZED1215, 0.46 mmol) are dissolved in a mixture of 10 mL of dichloromethane and 10 mL of TFA and stirred for 1.5 h at RT, before the volatile components are removed in vacuo and are dried under high vacuum. 137 mg (0.23 mmol) of the obtained oil are dissolved in 2.5 mL of DMF. To this solution a solution of 87 mg of HATU (0.23 mmol), 23 mg of benzoic acid (0.23 mmol) and 78 µL of DIPEA (2 eq) in 2 mL of DMF is added. By successive addition of DIPEA the pH value is adjusted to ca. 7. It is stirred overnight at RT, before the solvent is removed in vacuo. The residue is purified by preparative HPLC (30% ACN in water, 8 mL/min, gradient 1% pro min).

Yield: 74 mg, 0.13 mmol, 58%

ESI-MS: 577.4 [M+Na]⁺

¹H-NMR (DMSO-d6, 500 MHz): [[ppm]=12.64 (br, 1H), 9.33 (s, 1H), 8.83 (d, 1H), 8.41 (d, 1H), 8.22 (dd, 1H), 7.89 (m, 2H), 7.51 (m, 3H), 7.33 (dd, 1H), 6.94 (dt, 1H, J=15.68; 6.83), 6.24 (t, 1H), 5.86 (d, 1H, J=15.74), 4.69 (m, 3H), 4.21 (m, 1H), 3.61 (s, 3H), 2.34 (m, 2H), 2.00 (m, 2H), 1.77 (m, 1H), 1.43 (m, 1H), 1.19 (m, 1H), 0.86 (m, 6H)

4. Preparation of Example Compound (A58) (ZED1213)

(S,E)-7-tert-Butyl 1-ethyl 6-(bis(tert-butoxycarbonyl)amino)hept-2-enedioate (ZED724)

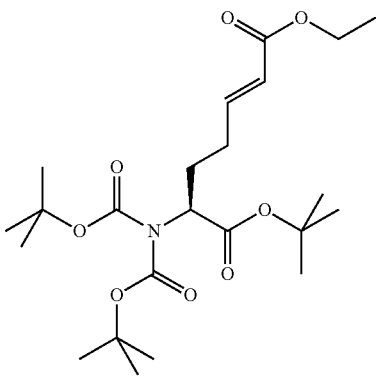

Molecular formula: C23H39NO8
Molecular weight: 457.56

1.06 g of Boc₂-Glu(H)—OtBu (2.74 mmol) are provided in 27 mL of dried benzene and under argon atmosphere at RT a solution of 1.00 g of (ethoxycarbonylmethylen)-triphenyl-phosphorane (2.74 mmol) in 13 mL of benzene is dropped. After stirring overnight, the solvent is removed in vacuo and the obtained residue is purified by chromatography on silica gel (column: 25*6.0 cm, dichloromethane/methanol 99.5:0.5).

Column chromatography: collected in 50 mL fractions, product: fractions 17-55

TLC control: Dichloromethane/Methanol 99.5:0.5, R_f=0.23

Yield: 972 mg, 2.72 mmol, 78%

ESI-MS: 480.3 [M+Na]⁺

(S,E)-2-(tert-butoxycarbonylamino)-7-ethoxy-7-oxohept-5-enoic acid (ZED775)

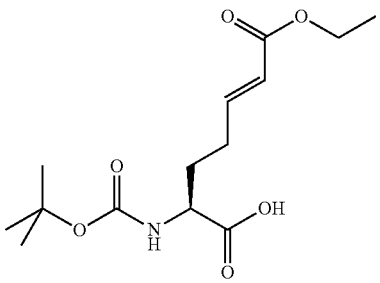

Molecular formula: C14H23NO6
Molecular weight: 301.34

972 mg of (S,E)-7-tert-butyl 1-ethyl 6-(bis(tert-butoxycarbonyl)amino)hept-2-enedioate (ZED724, 2.12 mmol) are dissolve in 15 mL of dichloromethane and to this solution 15 mL of trifluoroacetic acid is added. It is stirred at RT for 2 h. The solvent is removed in vacuo and the residue is dried under high vacuum. The obtained oil is further reacted without purification.

The oil is taken up in 30 mL DMF and treated with 361 µL of DIPEA. By successive addition of DIPEA the pH value is adjusted to ca. 7. 502 mg of Boc-OSu (2.33 mmol, 1.1 eq) are added and stirred at RT overnight. The solvent is removed in vacuo and the residue is purified by chromatography on silica gel (column: 23*6.0 cm, dichloromethane/methanol 9:1). Colorless oil is obtained.

Column chromatography: corrected in 50 mL fractions, product: fractions 35-80

TLC control: Dichloromethane/Methanol 9:1, $R_f$=0.21

Yield: 249 mg, 0.83 mmol, 39%

ESI-MS: 302.2 [M+H]$^+$ (S,E)-Ethyl 6-(tert-butoxycarbonylamino)-7-(1-(2-(2-ethylbutylamino)-2-oxoethyl)-2-oxo-1,2-dihydro-pyridin-3-ylamino)-7-oxohept-2-enoate (ZED1105)

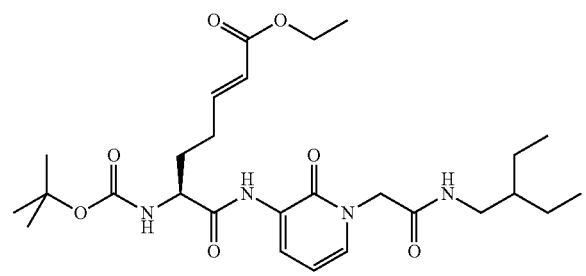

Molecular formula: C27H42N4O7
Molecular weight: 534.64

A solution of 101 mg of 2-(3-amino-2-oxopyridin-1(2H)-yl)-N-(2-ethyl-butyl)acetamide (2a, 0.40 mmol) in 2.5 mL of DMF is provided. To this solution, a solution of 121 mg of (S,E)-2-(tert-butoxycarbonylamino)-7-ethoxy-7-oxohept-5-enoic acid (ZED775, 0.40 mmol), 152 mg of HATU (0.40 mmol) and 136 µL of DIPEA (2 eq) in 2.5 mL of DMF is added. By successive addition of DIPEA the pH value is adjusted to ca. 7. The reaction mixture is stirred at 40° C. for 1.5 hours and subsequently at RT overnight, before the solvent is removed in vacuo. The obtained residue is taken up in 75 mL of ethyl acetate and subsequently washed each three times with 10% citric acid, saturated NaHCO$_3$ solution and brine. The organic phase is dried over Na$_2$SO$_4$, filtered and concentrated in vacuo in dryness. Gel is obtained and it is suitable for further processing without further purification.

Yield: 155 mg, 0.29 mmol, 73%

ESI-MS: 535.3 [M+H]$^+$ (S,E)-Ethyl 7-(1-(2-(2-ethylbutylamino)-2-oxo-ethyl)-2-oxo-1,2-dihydropyridin-3-ylamino)-6-(1-methyl-1H-imidazole-5-carboxamido)-7-oxohept-2-enoate (A58) (ZED1213)

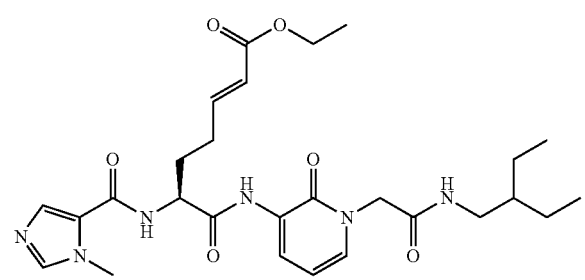

Molecular formula: C27H38N6O6
Molecular weight: 542.63

155 mg of (S,E)-methyl 6-(tert-butoxycarbonylamino)-7-(1-(2-(2-ethylbutylamino)-2-oxoethyl)-2-oxo-1,2-dihydro-pyridin-3-ylamino)-7-oxohept-2-enoate (ZED1223, 0.29 mmol) are dissolved in a mixture of 10 mL of dichloromethane and 10 mL of TFA and stirred for 1 h at RT, before the volatile components are removed in vacuo.

The obtained green oil is dried under high vacuum and dissolved in 2 mL of DMF. To this solution, a solution of 110 mg of HATU (0.29 mmol), 38 mg of 1-methyl-1H-imidazol-5-carboxylic acid (0.29 mmol) and 99 µL of DIPEA (2 eq) in 2 mL of DMF is added. By successive addition of DIPEA the pH value is adjusted to ca. 7. It is stirred overnight at RT, before the solvent is removed in vacuo. The residue is purified by HPLC (30% ACN in water, 8 mL/min, gradient 1% pro min). Yield: 64 mg, 0.12 mmol, 41%

ESI-MS: 543.4 [M+H]$^+$ $^1$H-NMR (DMSO-d6, 500 MHz): δ [ppm]=9.47 (s, 1H), 8.99 (d, 1H), 8.94 (s, 1H), 8.19 (m, 2H), 8.06 (d, 1H), 7.34 (dd, 1H), 6.92 (dt, 1H, J=15.63; 6.83), 6.25 (t, 1H), 5.85 (d, 1H, J=15.66), 4.73 (m, 1H), 4.59 (s, 2H), 4.08 (q, 2H), 3.95 (s, 3H), 3.02 (t, 2H), 2.34 (m, 2H), 2.02 (m, 1H), 1.89 (m, 1H), 1.27 (m, 5H), 1.19 (t, 3H), 0.83 (t, 6H)

5. Preparation of Example Compound (A6) (ZED1029)

(S,E)-7-tert-butyl 1-isopropyl 6-(bis(tert-butoxycarbonyl)amino)hept-2-enedioate (ZED855)

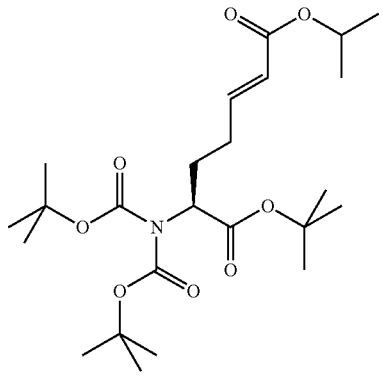

Molecular formula: C24H41NO8
Molecular weight: 471.58

951 mg of Boc$_2$-Glu(H)—OtBu (2.45 mmol) are provided in 20 mL of dried benzene and under argon atmosphere at RT a solution of 889 mg of (isopropoxycarbonylmethylen)-triphenyl-phosphorane (2.45 mmol) in 10 mL of benzene is dropped. After stirring overnight, the solvent is removed in vacuo. The obtained residue is purified by chromatography on silica gel (column: 39*3.2 cm, dichloromethane/methanol 99.5:0.5).

Column chromatography: collected in 50 mL fractions, product: fractions 9-20

TLC control: Dichloromethane/Methanol 99.5:0.5, $R_f$=0.32

Yield: 961 mg, 2.04 mmol, 83%

ESI-MS: 472.3 [M+H]$^+$

(S,E)-2-(tert-butoxycarbonylamino)-7-isopropoxy-7-oxohept-5-enoic acid (ZED902)

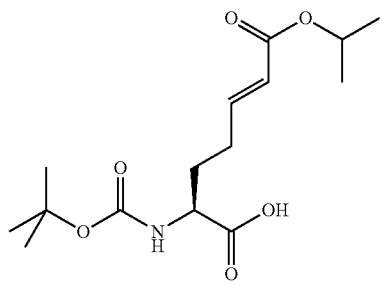

Molecular formula: C15H25NO6
Molecular weight: 315.36

518 mg of (S,E)-7-tert-butyl 1-isopropyl 6-(bis(tert-butoxycarbonyl)amino)hept-2-enedioate (ZED855, 1.10 mmol) are dissolve in 10 mL of dichloromethane and to this solution 10 mL of trifluoroacetic acid is added. It is stirred at RT for 2 h. The solvent is removed in vacuo and the residue is dried under high vacuum. The obtained oil is further reacted without purification.

The oil is taken up in 2.5 mL DMF and treated with 185 µL of DIPEA. By successive addition of DIPEA the pH value is adjusted to ca. 7. 259 mg of Boc-OSu (1.21 mmol, 1.1 eq) are added and stirred at RT overnight. The solvent is removed in vacuo and the residue is taken up in 75 mL of ethyl acetate and washed two times with 10% citric acid and once with brine. After drying of the organic phase over Na₂SO₄, the solvent is removed in vacuo. The residue is purified by preparative HPLC (40% ACN in water, 8 mL/min, gradient 1% pro min).

Yield: 267 mg, 0.85 mmol, 77%
ESI-MS: 316.2 [M+H]⁺

(S,E)-Isopropyl 6-(tert-butoxycarbonylamino)-7-(1-(2-(isopentylamino)-2-oxoethyl)-2-oxo-1,2-dihydropyridin-3-ylamino)-7-oxohept-2-enoate (ZED1024)

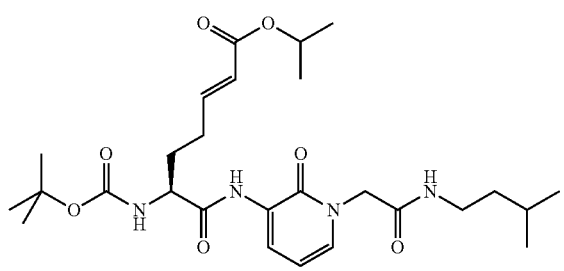

Molecular formula: C27H42N4O7
Molecular weight: 534.64

A solution of 214 mg of 2-(3-amino-2-oxopyridin-1(2H)-yl)-N-isopentylacetamide (ZED1022, 0.90 mmol) in 10 mL of DMF is provided. To this solution, a solution of 284 mg of (S,E)-2-(tert-butoxycarbonylamino)-7-isopropoxy-7-oxohept-5-enoic acid (ZED902, 0.90 mmol), 342 mg of HATU (0.90 mmol) and 306 µL of DIPEA (2 eq) in 10 mL of DMF is added. By successive addition of DIPEA the pH value is adjusted to ca. 7. The reaction mixture is stirred at 40° C. for 2.5 hours as well as at RT overnight, before the solvent is removed in vacuo. The obtained residue is taken up in 75 mL of ethyl acetate and subsequently washed each three times with 10% citric acid, saturated NaHCO₃ solution and brine. The organic phase is dried over Na₂SO₄, filtered and concentrated in vacuo in dryness. The residue is purified by preparative HPLC (50% ACN in water, 8 mL/min, gradient 1% pro min).

Yield: 295 mg, 0.55 mmol, 61%
ESI-MS: 535.4 [M+H]⁺

(S,E)-isopropyl 6-acetamido-7-(1-(2-(isopentylamino)-2-oxoethyl)-2-oxo-1,2-dihydropyridin-3-ylamino)-7-oxohept-2-enoate (A6) (ZED1029)

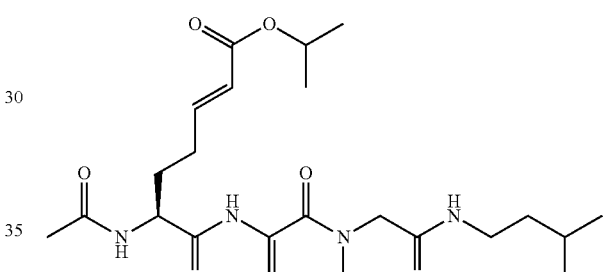

Molecular formula: C24H36N4O6
Molecular weight: 476.57

171 mg of (S,E)-isopropyl 6-(tert-butoxycarbonylamino)-7-(1-(2-(isopentylamino)-2-oxoethyl)-2-oxo-1,2-dihydropyridin-3-ylamino)-7-oxohept-2-enoate (ZED1024, 0.32 mmol) are dissolved in a mixture of 5 mL of dichloromethane and 5 mL of TFA and stirred for 1 h at RT, before the volatile components are removed in vacuo. The obtained oil is dried under high vacuum and dissolved in 10 mL of DMF and 113 µL of DIPEA (2 eq) as well as 36 µL of acid anhydride are added. By successive addition of DIPEA the pH value is adjusted to ca. 7. It is stirred for 3 h at RT, before the solvent is removed in vacuo. The residue is purified by preparative HPLC (40% ACN in water, 8 mL/min, gradient 1% pro min).

Yield: 111 mg, 0.23 mmol, 73%
ESI-MS: 477.3 [M+H]⁺
¹H-NMR (CDCl₃, 500 MHz): ⌊[ppm]=8.96 (s, 1H), 8.41 (dd, 1H), 7.14 (dd, 1H), 6.88 (dt, 1H, J=15.64; 6.86), 6.79 (s, 1H), 6.33 (t, 1H), 5.80 (d, 1H, J=15.66), 5.17 (s, 1H), 5.01 (m, 1H), 4.58 (m, 2H), 4.41 (s, 1H), 3.24 (m, 2H), 2.31 (m, 2H), 2.09 (m, 1H), 1.86 (s, 3H), 1.83 (m, 1H), 1.56 (m, 1H), 1.37 (m, 2H), 1.24 (d, 6H), 0.88 (d, 6H)

6. Preparation of Example Compound (A77) (ZED1393)

(S,E)-tert-butyl 2-(bis(tert-butoxycarbonyl)amino)-6-(methylsulfonyl)hex-5-enoate (ZED865)

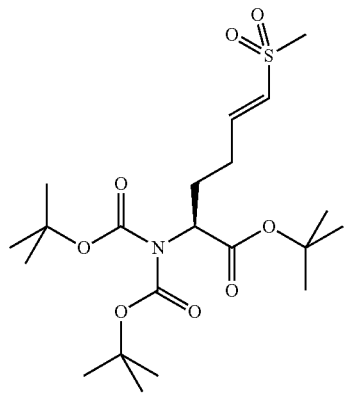

Molecular formula: C21H37NO8S
Molecular weight: 463.59

10 mg of NaH (60%, 0.26 mmol) are provided under argon atmosphere. A solution of 59 mg of diethyl-methylsulfonylmethylphosphonate (0.26 mmol) in 3 mL of DMF is added and stirred at RT, until the gas emission is finished. A solution of 100 mg Boc$_2$-Glu(H)—OtBu (0.26 mmol) in 0.5 ml of DMF is dropped and stirred at RT overnight. The solvent is removed in vacuo. The obtained residue is purified by chromatography on silica gel (column: 29*2.3 cm, dichloromethane/methanol 99:1).

Column chromatography: collected in 50 mL fractions, product: fractions 6-9
TLC control: Dichloromethane/Methanol 99:1, R$_f$=0.29
Yield: 89 mg, 0.19 mmol, 74%
ESI-MS: 464.2 [M+H]$^+$ (S,E)-2-(tert-butoxycarbonylamino)-6-(methylsulfonyl)hex-5-enoic acid (ZED1021)

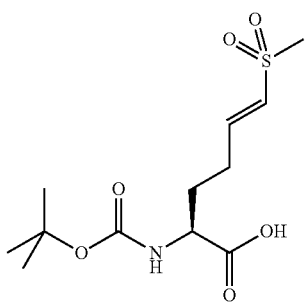

Molecular formula: C12H21NO6S
Molecular weight: 307.36

356 mg of (S,E)-tert-butyl 2-(bis(tert-butoxycarbonyl)amino)-6-(methylsulfonyl)hex-5-enoate (ZED865, 0.77 mmol) are dissolve in 10 mL of dichloromethane and to this solution 10 mL of trifluoroacetic acid is added. It is stirred at RT for 1 h. The solvent is removed in vacuo and the residue is dried under high vacuum. The obtained oil is further reacted without purification.

The oil is taken up in 5 mL of DMF and treated with 131 µL of DIPEA. By successive addition of DIPEA the pH value is adjusted to ca. 7. 182 mg of Boc-OSu (0.85 mmol, 1.1 eq) are added and stirred at RT overnight. The solvent is removed in vacuo and the residue is purified by preparative HPLC (5% ACN in water, 8 mL/min, gradient 1% pro min).
Yield: 148 mg, 0.48 mmol, 63%
ESI-MS: 308.1 [M+H]$^+$ (S,E)-tert-Butyl 1-(1-(2-(isopentylamino)-2-oxoethyl)-2-oxo-1,2-dihydropyridin-3-ylamino)-6-(methylsulfonyl)-1-oxohex-5-en-2-ylcarbamate (ZED1025)

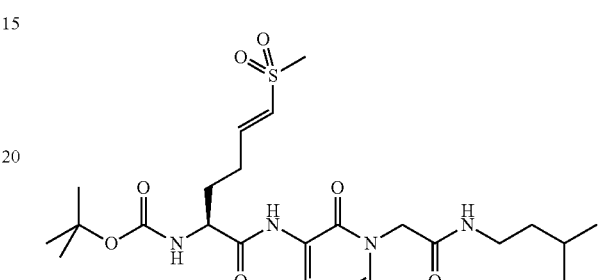

Molecular formula: C24H38N4O7S
Molecular weight: 526.65

A solution of 160 mg of 2-(3-amino-2-oxopyridin-1(2H)-yl)-N-isopentylacetamide (ZED1022, 0.90 mmol) in 5 mL of DMF is provided. To this solution, a solution of 212 mg of (S,E)-2-(tert-butoxycarbonylamino)-6-(methylsulfonyl)hex-5-enoic acid (ZED1021, 0.69 mmol), 260 mg of HATU (0.69 mmol) and 234 µL of DIPEA (2 eq) in 5 mL of DMF is added. By successive addition of DIPEA the pH value is adjusted to ca. 7. The reaction mixture is stirred at 40° C. for 2.5 hours as well as at RT overnight, before the solvent is removed in vacuo. The obtained residue is taken up in 75 mL of ethyl acetate and subsequently washed each three times with 10% citric acid, saturated NaHCO$_3$ solution and brine. The organic phase is dried over Na$_2$SO$_4$, filtered and concentrated in vacuo in dryness. The residue is further used without purification.
Yield: 251 mg, 0.48 mmol, 69%
ESI-MS: 527.3 [M+H]$^+$ (S,E)-2-acetamido-N-(1-(2-(isopentylamino)-2-oxoethyl)-2-oxo-1,2-dihydropyridin-3-yl)-6-(methylsulfonyl)hex-5-enamide (A77) (ZED1393)

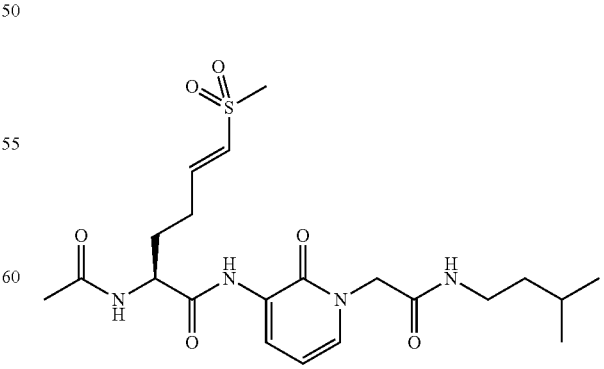

Molecular formula: C21H32N4O6S
Molecular weight: 468.57

251 mg of (S,E)-tert-butyl 1-(1-(2-(isopentylamino)-2-oxoethyl)-2-oxo-1,2-dihydropyridin-3-ylamino)-6-(methylsulfonyl)-1-oxohex-5-en-2-ylcarbamate (ZED1025, 0.48 mmol) are dissolved in a mixture of 10 mL of dichloromethane and 10 mL of TFA and stirred for 1 h at RT, before the volatile components are removed in vacuo. The obtained oil is dried under high vacuum and dissolved in 10 mL of DMF and 163 µL of DIPEA (2 eq) as well as 54 µL of acid anhydride (0.58 mmol) are added. By successive addition of DIPEA the pH value is adjusted to ca. 7. It is stirred for 3 h at RT, before the solvent is removed in vacuo. The residue is purified by preparative HPLC (30% ACN in water, 8 mL/min, gradient 1% pro min).

Yield: 130 mg, 0.28 mmol, 58%

ESI-MS: 469.2 [M+H]$^+$ $^1$H-NMR (CDCl$_3$, 500 MHz): δ [ppm]=8.98 (s, 1H), 8.41 (dd, 1H), 7.11 (dd, 1H), 6.86 (dt, 1H, J=15.63; 6.89), 6.80 (s, 1H), 6.33 (t, 1H), 5.78 (d, 1H, J=15.67), 5.11 (s, 1H), 4.56 (m, 2H), 4.43 (s, 1H), 3.27 (m, 2H), 2.87 (s, 3H), 2.30 (m, 2H), 2.09 (m, 1H), 1.87 (s, 3H), 1.84 (m, 1H), 1.58 (m, 1H), 1.33 (m, 2H), 0.87 (d, 6H)

7. Preparation of Example Compound (A78) (ZED1397)

(S,E)-1-Benzyl 7-tert-butyl 6-(bis(tert-butoxycarbonyl)amino)hept-2-enedioate (ZED818)

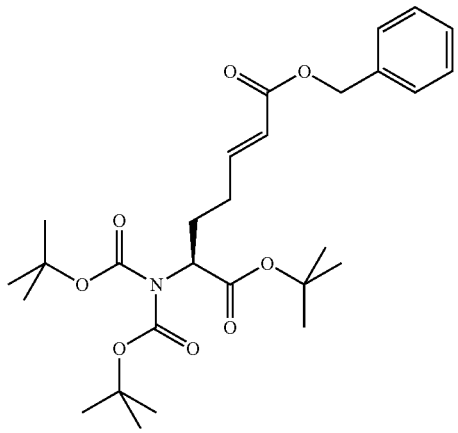

Molecular formula: C28H41NO8
Molecular weight: 519.63

100 mg of Boc$_2$-Glu(H)—OtBu (0.26 mmol) are provided in 3 mL of dried benzene and under argon atmosphere at RT a solution of 109 mg of benzyl(triphenylphosphoranylidene)acetate (0.26 mmol) in 2 mL of benzene is dropped. After stirring overnight, the solvent is removed in vacuo. The obtained residue is purified by chromatography on silica gel (column: 28*2.3 cm, dichloromethane/methanol 99:1).

Column chromatography: collected in 50 mL fractions, product: fractions 7-9

TLC control: Dichloromethane/Methanol 99:1, R$_f$=0.30

Yield: 94 mg, 0.18 mmol, 70%

ESI-MS: 520.2 [M+H]$^+$ (S,E)-7-(Benzyloxy)-2-(tert-butoxycarbonylamino)-7-oxohept-5-enoic acid (ZED1394)

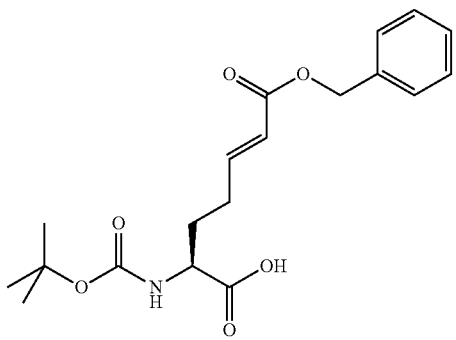

Molecular formula: C19H25NO6
Molecular weight: 363.40

94 mg of (S,E)-1-benzyl 7-tert-butyl 6-(bis(tert-butoxycarbonyl)amino)hept-2-enedioate (ZED818, 0.18 mmol) are dissolve in 2 mL of dichloromethane and to this solution 2 mL of trifluoroacetic acid is added. It is stirred at RT for 1.5 h. The solvent is removed in vacuo and the residue is dried under high vacuum. The obtained oil is further reacted without purification.

The oil is taken up in 2 mL DMF and treated with 61 µL of DIPEA (2 eq). By successive addition of DIPEA the pH value is adjusted to ca. 7. 43 mg of Boc-OSu (0.20 mmol, 1.1 eq) are added and stirred at RT overnight. The solvent is removed in vacuo and the residue is purified by preparative HPLC (35% ACN in water, 8 mL/min, gradient 1% pro min).

Yield: 60 mg, 0.16 mmol, 91%

ESI-MS: 364.1 [M+H]$^+$ (S,E)-Benzyl 6-(tert-butoxycarbonylamino)-7-(1-(2-(isopentylamino)-2-oxoethyl)-2-oxo-1,2-dihydropyridin-3-ylamino)-7-oxohept-2-enoate (ZED1396)

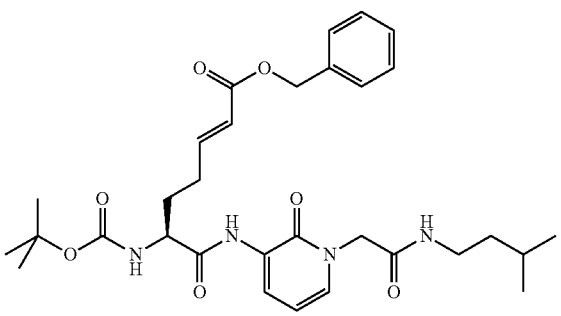

Molecular formula: C31H42N4O7
Molecular weight: 582.69

A solution of 38 mg of 2-(3-amino-2-oxopyridin-1(2H)-yl)-N-iso-pentylacetamide (ZED1022, 0.16 mmol) in 2 mL of DMF is provided. To this solution, a solution of 60 mg of (S,E)-7-(benzyloxy)-2-(tert-butoxycarbonylamino)-7-oxo-hept-5-enoic acid (ZED1394, 0.16 mmol), 61 mg of HATU (0.16 mmol) and 54 µL of DIPEA (2 eq) in 2 mL of DMF is added. By successive addition of DIPEA the pH value is adjusted to ca. 7. The reaction mixture is stirred at 40° C. for 3 h as well as at RT overnight, before the solvent is removed in vacuo. The obtained residue is taken up in 40 mL of ethyl acetate and subsequently washed each three times with 10% citric acid, saturated NaHCO₃ solution and brine. The organic phase is dried over Na₂SO₄, filtered and concentrated in vacuo in dryness. The residue is further used without purification.

Yield: 86 mg, 0.15 mmol, 92%
ESI-MS: 583.3 [M+H]⁺

(S,E)-Benzyl 6-acetamido-7-(1-(2-(isopentylamino)-2-oxoethyl)-2-oxo-1,2-dihydropyridin-3-ylamino)-7-oxohept-2-enoate A78 (ZED1397)

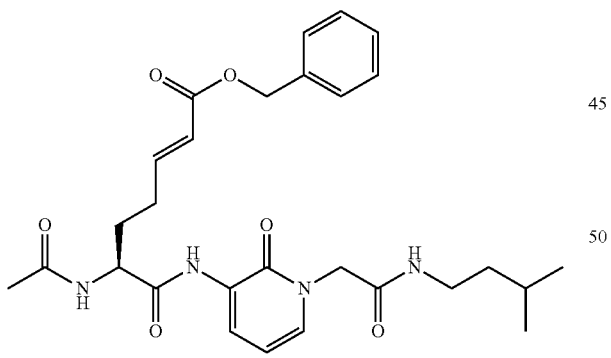

Molecular formula: C28H36N4O6
Molecular weight: 524.61

86 mg of (S,E)-benzyl 6-(tert-butoxycarbonylamino)-7-(1-(2-(isopentylamino)-2-oxoethyl)-2-oxo-1,2-dihydropyridin-3-ylamino)-7-oxohept-2-enoate (ZED1396, 0.15 mmol) are dissolved in a mixture of 3 mL of dichloromethane and 3 mL of TFA and stirred for 1 h at RT, before the volatile components are removed in vacuo. The obtained oil is dried under high vacuum and dissolved in 4 mL of DMF and 51 µL of DIPEA (2 eq) as well as 14 µL of acid anhydride (0.58 mmol) are added. By successive addition of DIPEA the pH value is adjusted to ca. 7. It is stirred for 4 h at RT, before the solvent is removed in vacuum. The residue is purified by preparative HPLC (35% ACN in water, 8 mL/min, gradient 1% pro min).

Yield: 49 mg, 0.09 mmol, 62%
ESI-MS: 525.3 [M+H]⁺
¹H-NMR (CDCl₃, 500 MHz): δ [ppm]=8.96 (s, 1H), 8.39 (dd, 1H), 7.37 (m, 5H), 7.10 (dd, 1H), 6.87 (dt, 1H, J=15.64; 6.85), 6.80 (s, 1H), 6.32 (t, 1H), 5.80 (d, 1H, J=15.68), 5.14 (s, 1H), 5.08 (s, 1H), 4.58 (m, 2H), 4.40 (s, 1H), 3.27 (m, 2H), 2.31 (m, 2H), 2.10 (m, 1H), 1.85 (s, 3H), 1.82 (m, 1H), 1.57 (m, 1H), 1.32 (m, 2H), 0.87 (d, 6H)

8. Execution Examples of Compounds According to the Invention (S,E)-Ethyl 6-(benzyloxycarbonylamino)-7-oxo-7-(2-oxo-1-(2-oxo-2-(2,4,6-trimethylphenethylamino)ethyl)-1,2-dihydropyridin-3-ylamino)hept-2-enoate (A1)

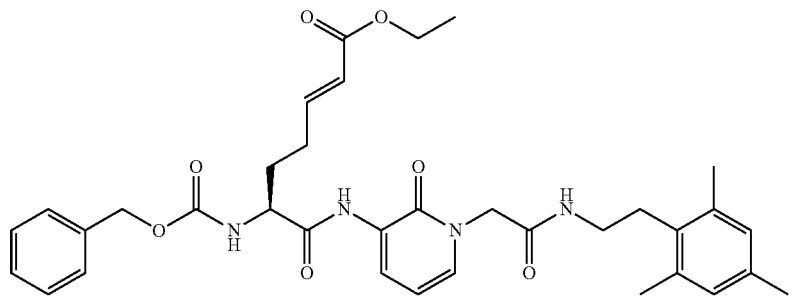

Molecular formula: C35H42N4O7
Molecular weight: 630.73

ESI-MS: 583.3 [M+H]⁺

(S,E)-Ethyl 6-(benzyloxycarbonylamino)-7-(1-(2-(isopentylamino)-2-oxoethyl)-6-methyl-2-oxo-1,2-dihydropyridin-3-ylamino)-7-oxohept-2-enoate (A2)

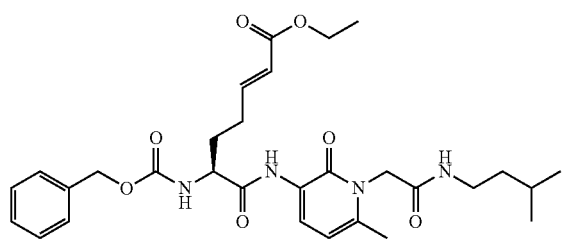

Molecular formula: C30H40N4O7
Molecular weight: 568.66

ESI-MS: 569.3 [M+H]⁺

63

(S,E)-Ethyl 6-(benzyloxycarbonylamino)-7-(1-(2-(isopentylamino)-2-oxoethyl)-2-oxo-1,2-dihydropyridin-3-ylamino)-7-oxohept-2-enoate (A3)

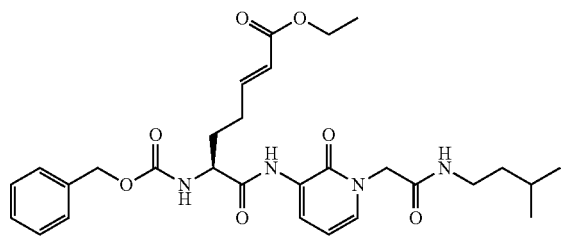

Molecular formula: C29H38N4O7
Molecular weight: 554.63

ESI-MS: 555.3 [M+H]$^+$ (S,E)-Ethyl 6-acetamido-7-(1-(2-(isopentylamino)-2-oxoethyl)-6-methyl-2-oxo-1,2-dihydropyridin-3-ylamino)-7-oxohept-2-enoate (A4)

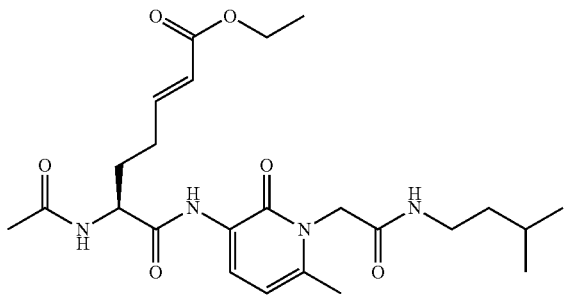

Molecular formula: C24H36N4O6
Molecular weight: 476.57

ESI-MS: 555.3 [M+H]$^+$

500-MHz-$^1$H-NMR-cosy (DMSO$_{d6}$): δ [ppm]=8.19 (d, 1H, H-3), 7.88 (d, 1H, H-6), 7.47 (d, 1H, H-14), 7.37-7.31 (m, 5H, Aryl-H), 6.87 (dt, 1H, H-10, J$_{10/9}$=6.6 Hz, J$_{11/10}$=15.4 Hz), 5.81 (d, 1H, H-11, J$_{11/10}$=15.4 Hz), 5.02 (s, 2H, Benzyl-CH$_2$), 4.37-4.28 (m, 2H, H-5, H-4), 4.28-4.20 (m, 1H, H-2), 4.10 (q, 2H, H-12$_a$, H-12$_b$), 4.08-4.00 (m, 1H, H-7), 3.73-3.67 (m, 1H, H-4c$_a$), 3.61 (s, 3H, OMe), 3.60-3.52 (m, 1H, H-4c$_b$), 2.27-2.15 (m, 2H, H-9$_a$, H-9$_b$), 2.10-2.00 (m, 1H, H-4$_{a/1}$), 2.00-1.90 (m, 2H, H-4$_{b/1}$, Methine-H (Val)), 1.88-1.78 (m, 3H, H-4$_{a/2}$, H-4$_{b/2}$), 1.78-1.65 (m, 2H, H-8$_a$, Methine-H (Leu)), 1.65-1.60 (m, 1H, H-8$_b$), 1.58-1.50 (m, 1H, CH$_{2a}$-Leu), 1.50-1.43 (m, 1H, CH$_{2b}$-Leu), 1.22 (t, 3H, CH$_3$-16), 0.89 (dd, 6H, 2×CH$_3$-Val), 0.84 (dd, 6H, 2×CH$_3$-Leu).

64

3-(2-(3-((S,E)-2-(Benzyloxycarbonylamino)-7-ethoxy-7-oxohept-5-enamido)-6-methyl-2-oxopyridin-1(2H)-yl)acetamido)-5-methylhexanoic acid (A5)

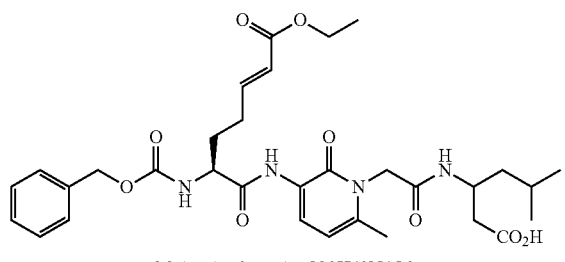

Molecular formula: C32H42N4O9
Molecular weight: 626.70

ESI-MS: 627.3 [M+H]$^+$ (S,E)-Ethyl 6-acetamido-7-(1-(2-(isopentylamino)-2-oxoethyl)-2-oxo-1,2-dihydropyridin-3-ylamino)-7-oxohept-2-enoate (A7)

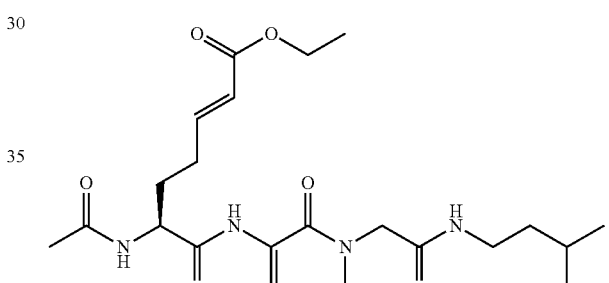

Molecular formula: C23H34N4O6
Molecular weight: 462.54

ESI-MS: 463.3 [M+H]$^+$ (S,E)-Ethyl 7-(6-methyl-2-oxo-1-(2-oxo-2-(phenethylamino)ethyl)-1,2-dihydropyridin-3-ylamino)-6-(nicotinamido)-7-oxohept-2-enoate (A8)

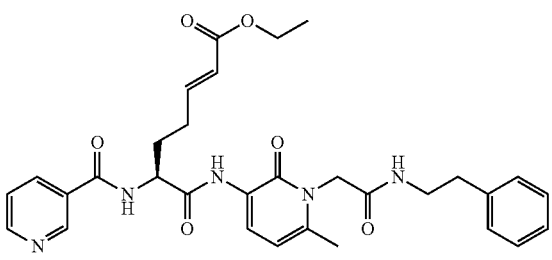

Molecular formula: C31H35N5O6
Molecular weight: 573.64

ESI-MS: 574.4 [M+H]$^+$

65

(S,E)-ethyl 6-((4-chlorophenyl)methylsulfonamido)-7-(1-(2-(isopentylamino)-2-oxoethyl)-2-oxo-1,2-dihydropyridin-3-ylamino)-7-oxohept-2-enoate (A9)

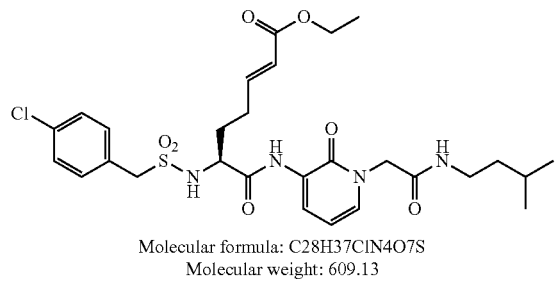 [SMILES: CCOC(=O)/C=C/CC[C@H](NS(=O)(=O)Cc1ccc(Cl)cc1)C(=O)Nc1cccn(CC(=O)NCCC(C)C)c1=O]

Molecular formula: C28H37ClN4O7S
Molecular weight: 609.13

ESI-MS: 609.2 [M+H]+

(S,E)-Ethyl 6-benzamido-7-(1-(2-(isopentylamino)-2-oxoethyl)-2-oxo-1,2-dihydropyridin-3-ylamino)-7-oxohept-2-enoate (A10)

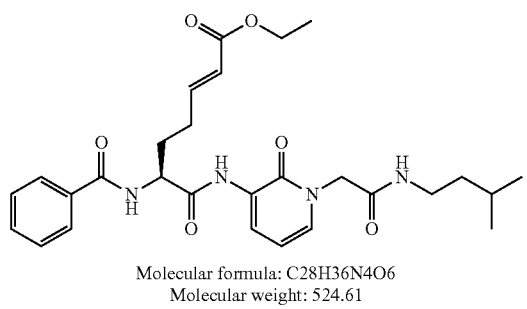 [SMILES: CCOC(=O)/C=C/CC[C@H](NC(=O)c1ccccc1)C(=O)Nc1cccn(CC(=O)NCCC(C)C)c1=O]

Molecular formula: C28H36N4O6
Molecular weight: 524.61

ESI-MS: 525.3 [M+H]+

(S,E)-Ethyl 6-(furan-3-carboxamido)-7-(1-(2-(isopentylamino)-2-oxoethyl)-2-oxo-1,2-dihydropyridin-3-ylamino)-7-oxohept-2-enoate (A11)

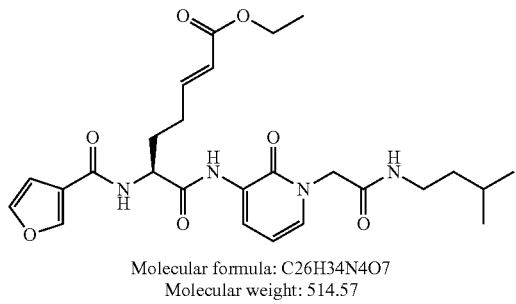 [SMILES: CCOC(=O)/C=C/CC[C@H](NC(=O)c1ccoc1)C(=O)Nc1cccn(CC(=O)NCCC(C)C)c1=O]

Molecular formula: C26H34N4O7
Molecular weight: 514.57

ESI-MS: 515.2 [M+H]+

66

(S,E)-Ethyl 7-(1-(2-(isopentylamino)-2-oxoethyl)-2-oxo-1,2-dihydropyridin-3-ylamino)-7-oxo-6-(thiophene-3-carboxamido)hept-2-enoate (A12)

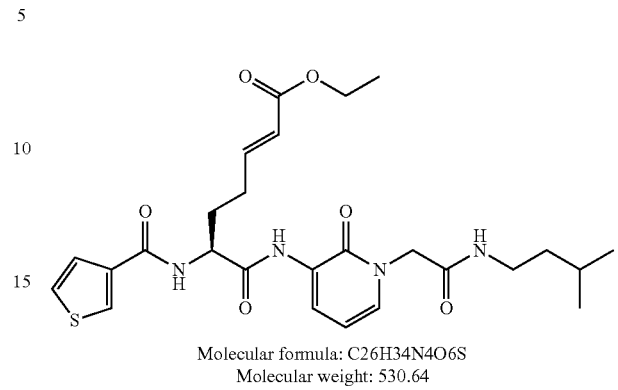

Molecular formula: C26H34N4O6S
Molecular weight: 530.64

ESI-MS: 531.2 [M+H]+

(S,E)-Ethyl 6-(furan-3-sulfonamido)-7-(1-(2-(isopentylamino)-2-oxoethyl)-2-oxo-1,2-dihydropyridin-3-ylamino)-7-oxohept-2-enoate (A13)

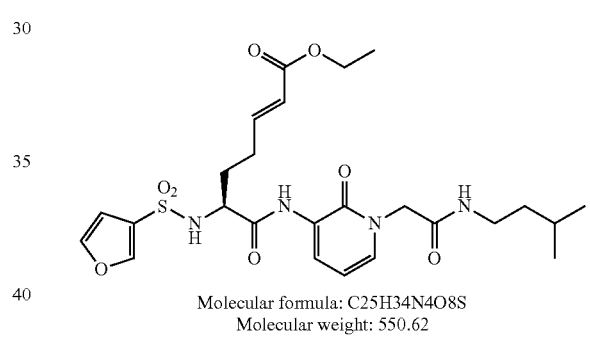

Molecular formula: C25H34N4O8S
Molecular weight: 550.62

ESI-MS: 551.2 [M+H]+

(S,E)-Ethyl 7-(1-(2-(isopentylamino)-2-oxoethyl)-2-oxo-1,2-dihydropyridin-3-ylamino)-7-oxo-6-(4-sulfamoylbenzamido)hept-2-enoate (A14)

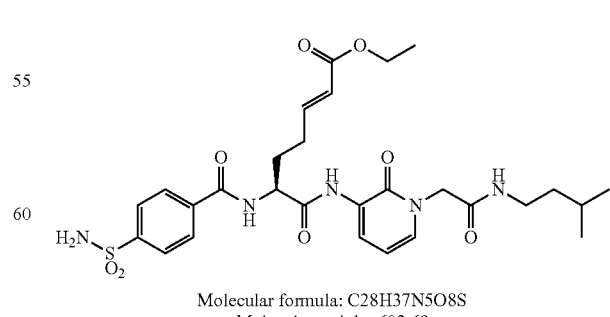

Molecular formula: C28H37N5O8S
Molecular weight: 603.69

ESI-MS: 604.3 [M+H]+

67

(S,E)-Ethyl 7-(1-(2-(isopentylamino)-2-oxoethyl)-2-oxo-1,2-dihydropyridin-3-ylamino)-6-(5-methylthiazole-4-carboxamido)-7-oxohept-2-enoate (A15)

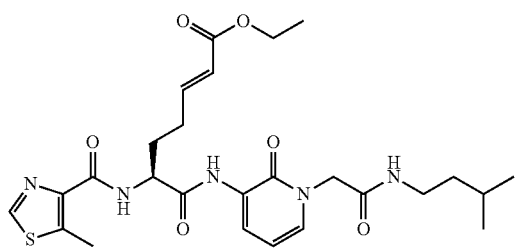

Molecular formula: C26H35N5O6S
Molecular weight: 545.65

ESI-MS: 546.2 [M+H]$^+$ (S,E)-Ethyl 7-(1-(2-(isopentylamino)-2-oxoethyl)-2-oxo-1,2-dihydropyridin-3-ylamino)-6-(nicotinamido)-7-oxohept-2-enoate (A16)

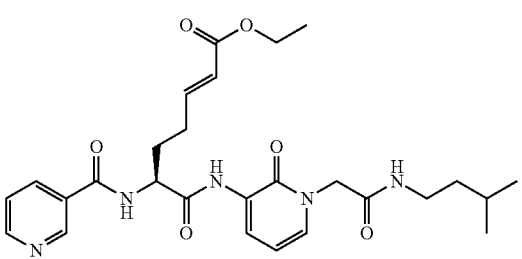

Molecular formula: C27H35N5O6
Molecular weight: 525.60

ESI-MS: 526.3 [M+H]$^+$ (S,E)-Ethyl 6-(3,5-bis(trifluoromethyl)benzamido)-7-(1-(2-(isopentylamino)-2-oxoethyl)-2-oxo-1,2-dihydropyridin-3-ylamino)-7-oxohept-2-enoate (A17)

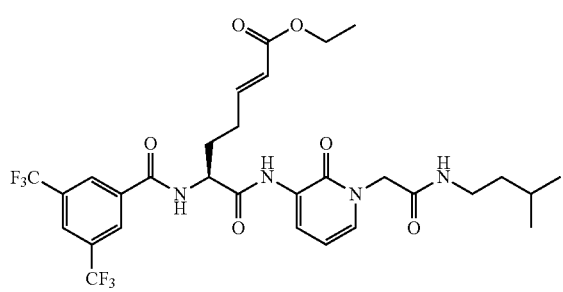

Molecular formula: C30H34F6N4O6
Molecular weight: 660.60

ESI-MS: 661.3 [M+H]$^+$

68

(S,E)-Ethyl 7-(1-(2-(isopentylamino)-2-oxoethyl)-2-oxo-1,2-dihydropyridin-3-ylamino)-7-oxo-6-(4-(piperidin-1-yl)benzamido)hept-2-enoate (A18)

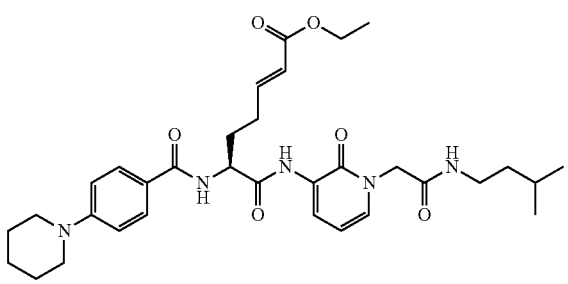

Molecular formula: C33H45N5O6
Molecular weight: 607.74

ESI-MS: 608.3 [M+H]$^+$ (S,E)-Ethyl 7-(1-(2-(isopentylamino)-2-oxoethyl)-2-oxo-1,2-dihydropyridin-3-ylamino)-6-(1-methyl-1H-imidazole-5-carboxamido)-7-oxohept-2-enoate (A19)

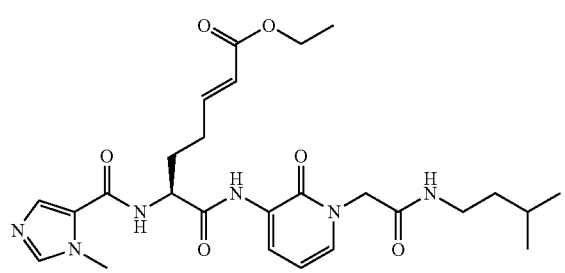

Molecular formula: C26H36N6O6
Molecular weight: 528.60

ESI-MS: 529.3 [M+H]$^+$ (S,E)-Ethyl 7-(1-(2-(isopentylamino)-2-oxoethyl)-2-oxo-1,2-dihydropyridin-3-ylamino)-6-(4-(4-methyl-piperazin-1-yl)benzamido)-7-oxohept-2-enoate (A20)

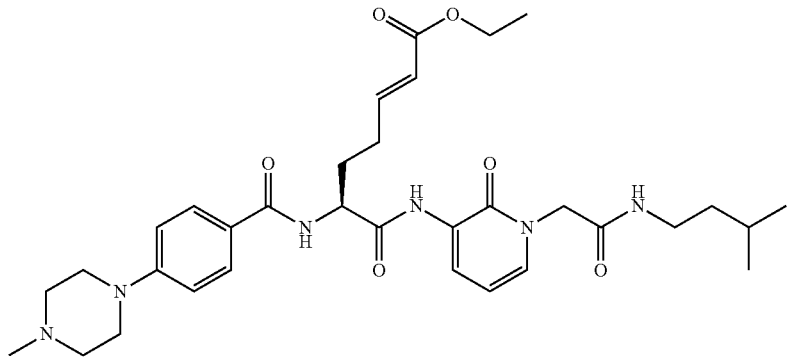

Molecular formula: C23H46N6O6
Molecular weight: 622.75

ESI-MS: 623.4 [M+H]⁺

(S,E)-Ethyl 7-(1-(2-(isopentylamino)-2-oxoethyl)-2-oxo-1,2-dihydropyridin-3-ylamino)-6-(4-methyl-3,4-dihydro-2H-benzo[b][1,4]oxazine-7-carboxamido)-7-oxohept-2-enoate (A21)

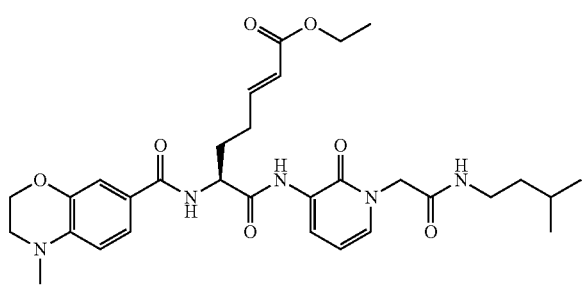

Molecular formula: C31H41N5O7
Molecular weight: 595.69

ESI-MS: 596.3 [M+H]⁺

(S,E)-Ethyl 7-(1-(2-(isopentylamino)-2-oxoethyl)-2-oxo-1,2-dihydropyridin-3-ylamino)-7-oxo-6-(phenylsulfonamido)hept-2-enoate (A22)

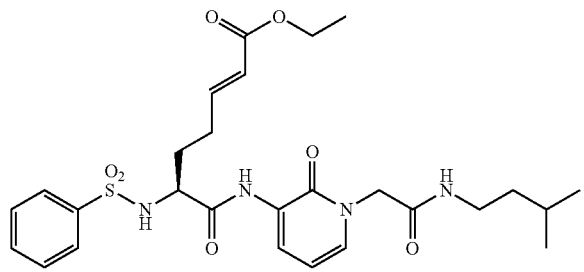

Molecular formula: C27H36N4O7S
Molecular weight: 560.66

ESI-MS: 561.3 [M+H]⁺

(S,E)-5-(N-(7-Ethoxy-1-(1-(2-(isopentylamino)-2-oxoethyl)-2-oxo-1,2-dihydropyridin-3-ylamino)-1,7-dioxohept-5-en-2-yl)sulfamoyl)-2-hydroxybenzoic acid (A23)

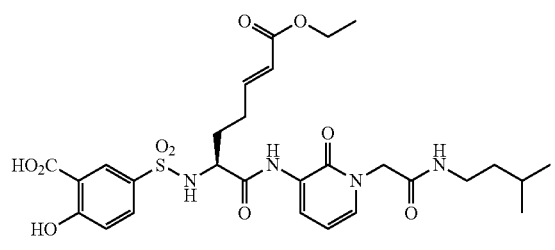

Molecular formula: C28H36N4O10S
Molecular weight: 620.67

ESI-MS: 621.2 [M+H]⁺

(S,E)-4-(7-Ethoxy-1-(1-(2-(isopentylamino)-2-oxoethyl)-2-oxo-1,2-dihydropyridin-3-ylamino)-1,7-dioxohept-5-en-2-ylamino)-4-oxobutanoic acid (A24)

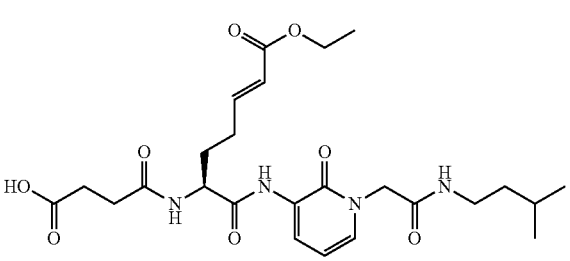

Molecular formula: C25H36N4O8
Molecular weight: 520.58

ESI-MS: 521.2 [M+H]⁺

71

(S,E)-Ethyl 6-acetamido-7-(1-(2-(2-(diethylamino)ethylamino)-2-oxoethyl)-2-oxo-1,2-dihydropyridin-3-ylamino)-7-oxohept-2-enoate (A25)

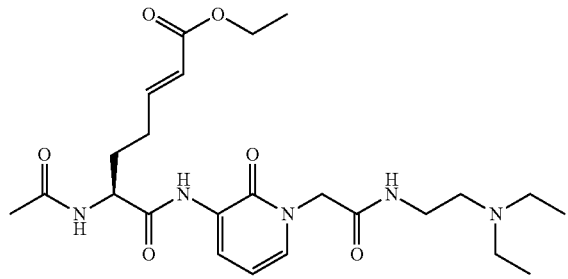

Molecular formula: C24H37N5O6
Molecular weight: 491.58

ESI-MS: 492.3 [M+H]+

(S,E)-4-(1-(1-(2-(2-(Diethylamino)ethylamino)-2-oxoethyl)-2-oxo-1,2-dihydropyridin-3-ylamino)-7-ethoxy-1,7-dioxohept-5-en-2-ylamino)-4-oxobutanoic acid (A26)

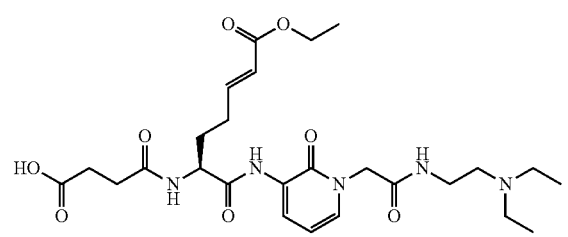

Molecular formula: C26H39N5O8
Molecular weight: 549.62

ESI-MS: 550.3 [M+H]+

(S,E)-Ethyl 6-acetamido-7-(1-(2-(2-(dimethylamino)ethylamino)-2-oxoethyl)-2-oxo-1,2-dihydropyridin-3-ylamino)-7-oxohept-2-enoate (A27)

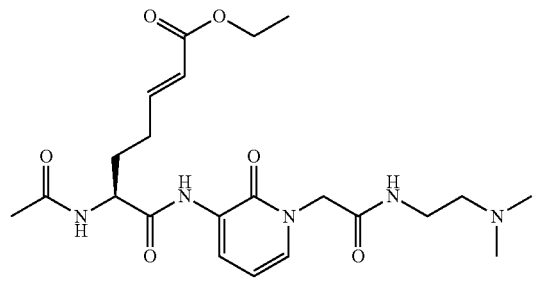

Molecular formula: C22H33N5O6
Molecular weight: 463.53

ESI-MS: 464.2 [M+H]+

72

(S,E)-Methyl 6-acetamido-7-(1-(2-(isopentylamino)-2-oxoethyl)-2-oxo-1,2-dihydropyridin-3-ylamino)-7-oxohept-2-enoate (A28)

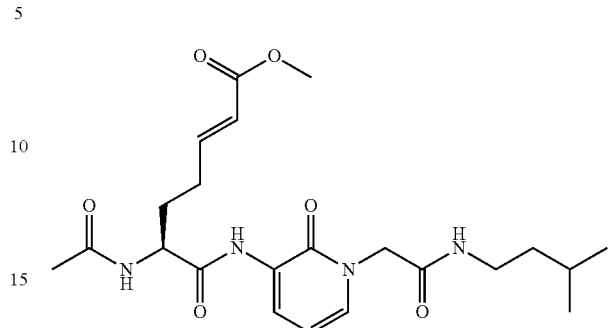

Molecular formula: C22H32N4O6
Molecular weight: 448.51

ESI-MS: 449.2 [M+H]+

(S,E)-4-(7-Ethoxy-1-(1-(2-(2-ethylbutylamino)-2-oxoethyl)-2-oxo-1,2-dihydropyridin-3-ylamino)-1,7-dioxohept-5-en-2-ylamino)-4-oxobutanoic acid (A30)

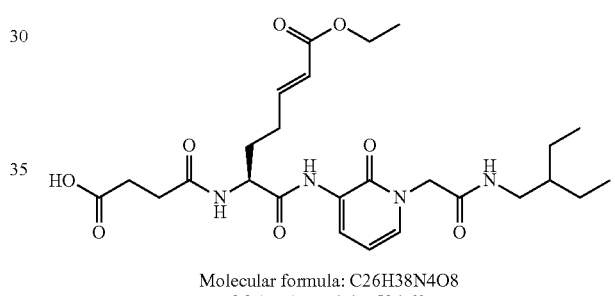

Molecular formula: C26H38N4O8
Molecular weight: 534.60

ESI-MS: 535.3 [M+H]+

(S,E)-Ethyl 6-acetamido-7-(1-(2-((S)-1-methoxy-4-methyl-1-oxopentan-2-ylamino)-2-oxoethyl)-2-oxo-1,2-dihydropyridin-3-ylamino)-7-oxohept-2-enoate (A31)

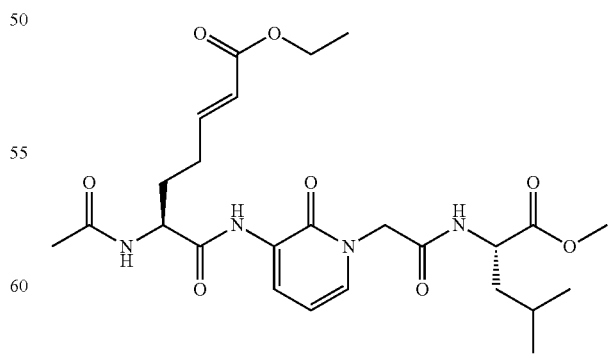

Molecular formula: C25H36N4O8
Molecular weight: 520.58

ESI-MS: 521.3 [M+H]+

73

4-((S,E)-7-Ethoxy-1-(1-(2-((S)-1-methoxy-4-methyl-1-oxopentan-2-ylamino)-2-oxoethyl)-2-oxo-1,2-dihydropyridin-3-ylamino)-1,7-dioxohept-5-en-2-ylamino)-4-oxobutanoic acid (A32)

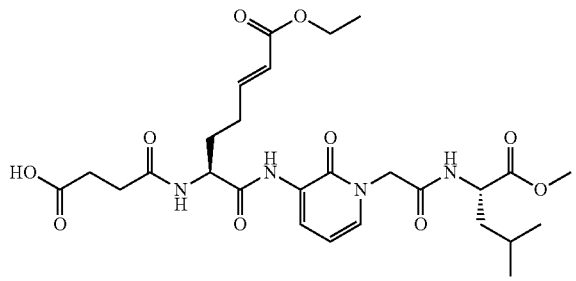

Molecular formula: C27H38N4O10
Molecular weight: 578.61

ESI-MS: 579.3 [M+H]+

(S,E)-Ethyl 6-acetamido-7-(1-(2-((R)-1-methoxy-4-methyl-1-oxopentan-2-ylamino)-2-oxoethyl)-2-oxo-1,2-dihydropyridin-3-ylamino)-7-oxohept-2-enoate (A33)

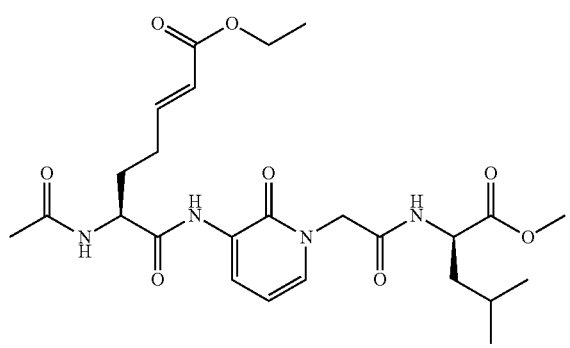

Molecular formula: C25H36N4O8
Molecular weight: 520.58

ESI-MS: 521.3 [M+H]+

4-((S,E)-7-Ethoxy-1-(1-(2-((R)-1-methoxy-4-methyl-1-oxopentan-2-ylamino)-2-oxoethyl)-2-oxo-1,2-dihydropyridin-3-ylamino)-1,7-dioxohept-5-en-2-ylamino)-4-oxobutanoic acid (A34)

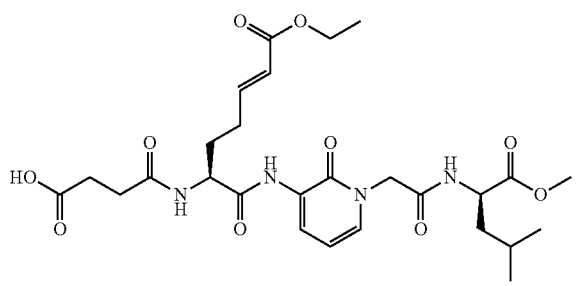

Molecular formula: C27H38N4O10
Molecular weight: 578.61

ESI-MS: 579.3 [M+H]+

74

(S,E)-ethyl 6-acetamido-7-(1-(2-((2S,3R)-1-methoxy-3-methyl-1-oxopentan-2-ylamino)-2-oxoethyl)-2-oxo-1,2-dihydropyridin-3-ylamino)-7-oxohept-2-enoate (A35)

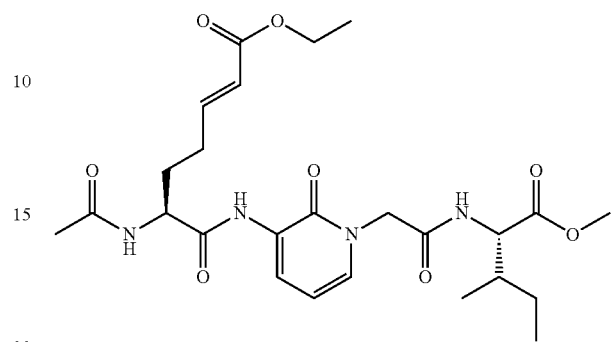

Molecular formula: C25H36N4O8
Molecular weight: 520.58

ESI-MS: 521.3 [M+H]+

4-((S,E)-7-Ethoxy-1-(1-(2-((2S,3R)-1-methoxy-3-methyl-1-oxopentan-2-ylamino)-2-oxoethyl)-2-oxo-1,2-dihydropyridin-3-ylamino)-1,7-dioxohept-5-en-2-ylamino)-4-oxobutanoic acid (A36)

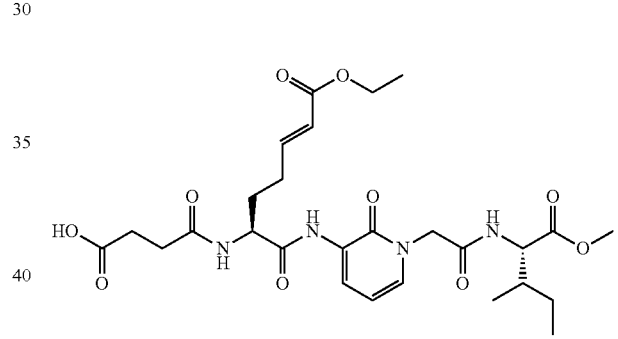

Molecular formula: C27H38N4O10
Molecular weight: 578.61

ESI-MS: 579.3 [M+H]+

(S,E)-4-(7-Ethoxy-1,7-dioxo-1-(2-oxo-1-(2-oxo-2-(4-(trifluoromethyl)benzylamino)ethyl)-1,2-dihydropyridin-3-ylamino)hept-5-en-2-ylamino)-4-oxobutanoic acid (A37)

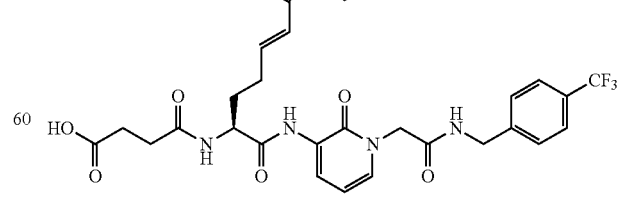

Molecular formula: C28H31F3N4O8
Molecular weight: 608.56

ESI-MS: 609.2 [M+H]+

75

(S,E)-4-(1-(1-(2-(3,3-Dimethylbutylamino)-2-oxo-ethyl)-2-oxo-1,2-dihydropyridin-3-ylamino)-7-ethoxy-1,7-dioxohept-5-en-2-ylamino)-4-oxobutanoic acid (A38)

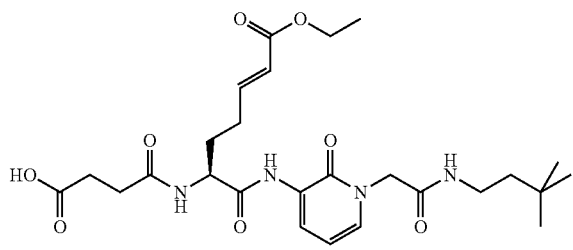

Molecular formula: C26H38N4O8
Molecular weight: 534.60

ESI-MS: 535.3 [M+H]+

(S,E)-Ethyl 6-acetamido-7-(1-(2-(3,3-dimethylbutylamino)-2-oxoethyl)-2-oxo-1,2-dihydropyridin-3-ylamino)-7-oxohept-2-enoate (A39)

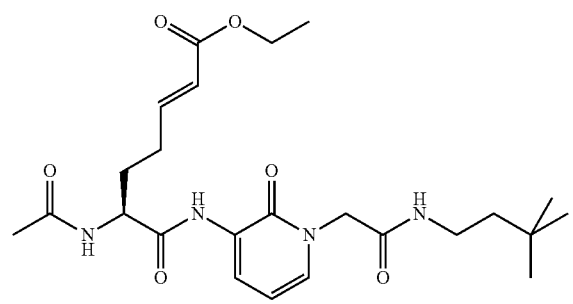

Molecular formula: C24H36N4O6
Molecular weight: 476.57

ESI-MS: 477.3 [M+H]+

(S,E)-Ethyl 6-acetamido-7-(1-(2-((S)-1-methoxy-4,4-dimethyl-1-oxopentan-2-ylamino)-2-oxoethyl)-2-oxo-1,2-dihydropyridin-3-ylamino)-7-oxohept-2-enoate (A40)

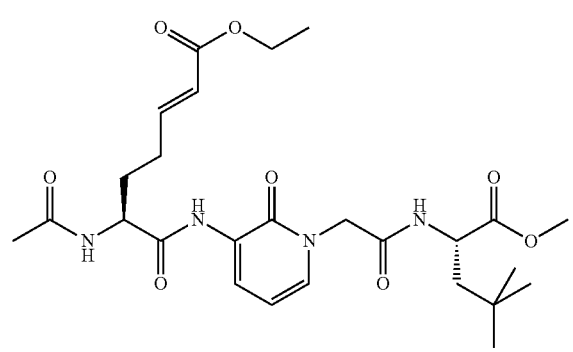

Molecular formula: C26H38N4O8
Molecular weight: 534.60

ESI-MS: 535.3 [M+H]+

76

4-((S,E)-7-Ethoxy-1-(1-(2-((S)-1-methoxy-4,4-dimethyl-1-oxopentan-2-ylamino)-2-oxoethyl)-2-oxo-1,2-dihydropyridin-3-ylamino)-1,7-dioxohept-5-en-2-ylamino)-4-oxobutanoic acid (A41)

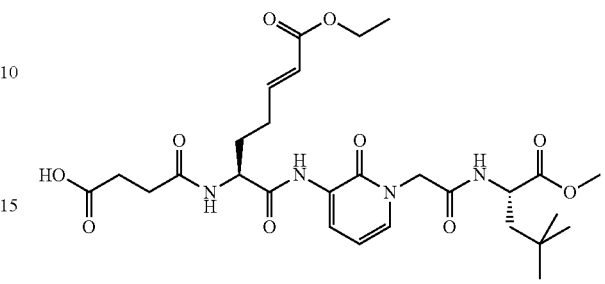

Molecular formula: C28H40N4O10
Molecular weight: 592.64

ESI-MS: 593.3 [M+H]+

(S,E)-ethyl 6-acetamido-7-(1-(2-(3-ethylpentylamino)-2-oxoethyl)-2-oxo-1,2-dihydropyridin-3-ylamino)-7-oxohept-2-enoate (A42)

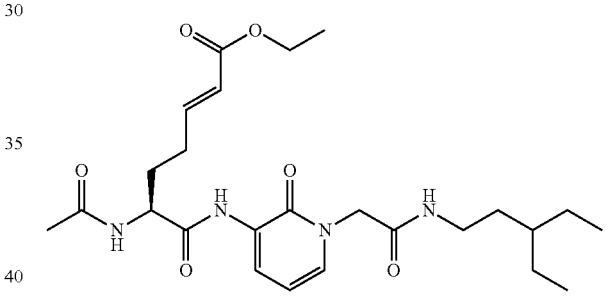

Molecular formula: C25H38N4O6
Molecular weight: 490.59

ESI-MS: 491.3 [M+H]+

(S,E)-4-(7-Ethoxy-1-(1-(2-(3-ethylpentylamino)-2-oxoethyl)-2-oxo-1,2-dihydropyridin-3-ylamino)-1,7-dioxohept-5-en-2-ylamino)-4-oxobutanoic acid (A43)

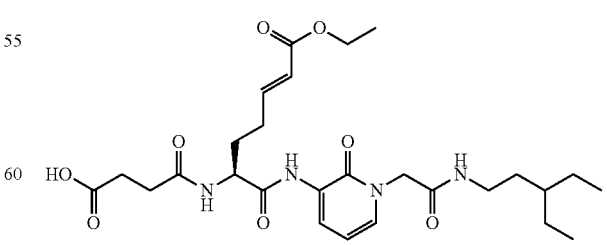

Molecular formula: C27H40N4O8
Molecular weight: 548.63

ESI-MS: 549.3 [M+H]+

77

(S,E)-4-(7-Ethoxy-1,7-dioxo-1-(2-oxo-1-(2-oxo-2-(2-(trifluoromethyl)benzylamino)ethyl)-1,2-dihydropyridin-3-ylamino)hept-5-en-2-ylamino)-4-oxobutanoic acid (A44)

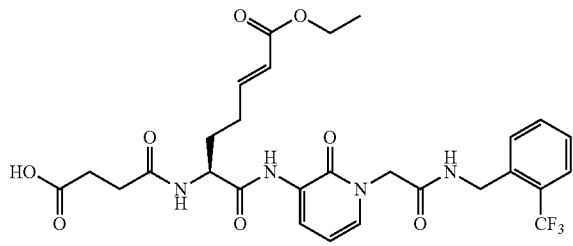

Molecular formula: C28H31F3N4O8
Molecular weight: 608.56

ESI-MS: 609.2 [M+H]$^+$ (S,E)-4-(7-Ethoxy-1,7-dioxo-1-(2-oxo-1-(2-oxo-2-(4-(trifluoromethyl)piperidin-1-yl)ethyl)-1,2-dihydropyridin-3-ylamino)hept-5-en-2-ylamino)-4-oxobutanoic acid (A45)

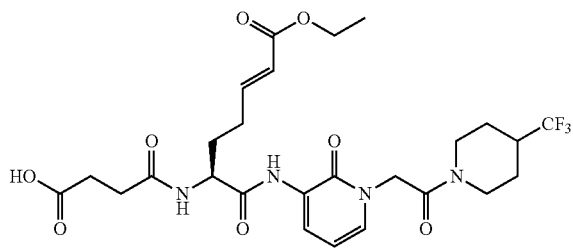

Molecular formula: C26H33F3N4O8
Molecular weight: 586.56

ESI-MS: 587.2 [M+H]$^+$ (S,E)-Ethyl 6-acetamido-7-oxo-7-(2-oxo-1-(2-oxo-2-(pyrrolidin-1-yl)ethylamino)ethyl)-1,2-dihydropyridin-3-ylamino)hept-2-enoate (A46)

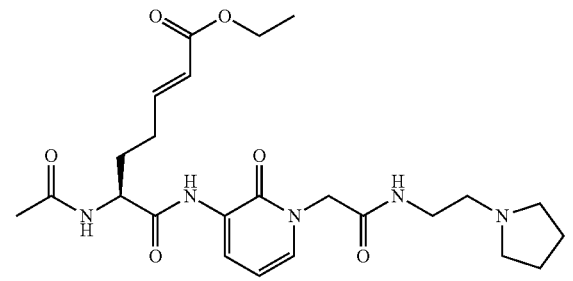

Molecular formula: C24H35N5O6
Molecular weight: 489.56

ESI-MS: 490.3 [M+H]$^+$

78

(S,E)-4-(7-Ethoxy-1,7-dioxo-1-(2-oxo-1-(2-oxo-2-(2-(thiophen-2-yl)ethylamino)ethyl)-1,2-dihydropyridin-3-ylamino)hept-5-en-2-ylamino)-4-oxobutanoic acid (A47)

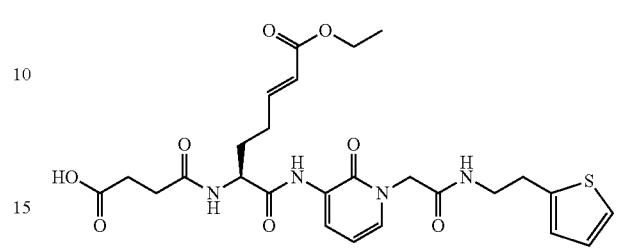

Molecular formula: C26H32N4O8S
Molecular weight: 560.62

ESI-MS: 561.2 [M+H]$^+$ (S,E)-Ethyl 6-acetamido-7-(1-(2-((1-ethylpiperidin-4-yl)methylamino)-2-oxoethyl)-2-oxo-1,2-dihydropyridin-3-ylamino)-7-oxohept-2-enoate (A48)

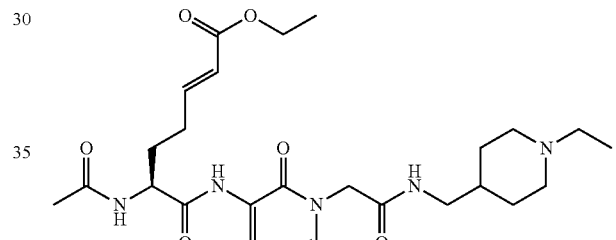

Molecular formula: C26H39N5O6
Molecular weight: 517.62

ESI-MS: 518.3 [M+H]$^+$ (S,E)-4-(7-Ethoxy-1,7-dioxo-1-(2-oxo-1-(2-oxo-2-(2-(2-oxoimidazolidin-1-yl)ethylamino)ethyl)-1,2-dihydropyridin-3-ylamino)hept-5-en-2-ylamino)-4-oxobutanoic acid (A49)

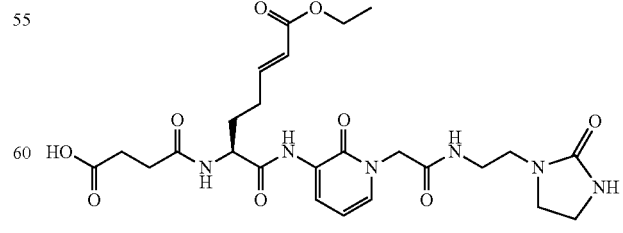

Molecular formula: C25H34N6O9
Molecular weight: 562.57

ESI-MS: 563.2 [M+H]$^+$

79

(6S,E)-Ethyl 6-acetamido-7-(1-(2-(2-methylbutylamino)-2-oxoethyl)-2-oxo-1,2-dihydropyridin-3-ylamino)-7-oxohept-2-enoate (A50)

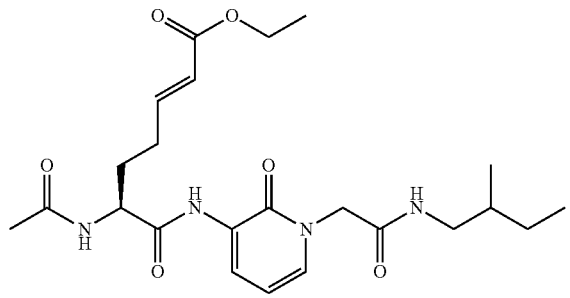

Molecular formula: C23H34N4O6
Molecular weight: 462.54

ESI-MS: 463.3 [M+H]$^+$ 4-((2S,E)-7-Ethoxy-1-(1-(2-(2-methylbutylamino)-2-oxoethyl)-2-oxo-1,2-dihydropyridin-3-ylamino)-1,7-dioxohept-5-en-2-ylamino)-4-oxobutanoic acid (A51)

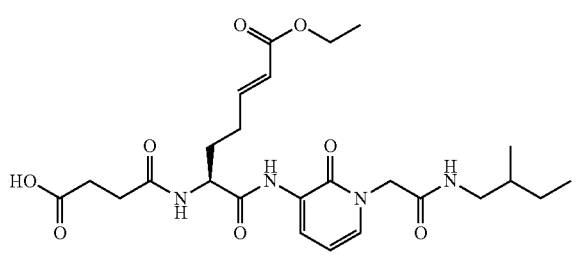

Molecular formula: C25H36N4O8
Molecular weight: 520.58

ESI-MS: 521.3 [M+H]$^+$ (6S,E)-Ethyl 6-acetamido-7-(1-(2-(3-methylpiperidin-1-yl)-2-oxoethyl)-2-oxo-1,2-dihydropyridin-3-ylamino)-7-oxohept-2-enoate (A52)

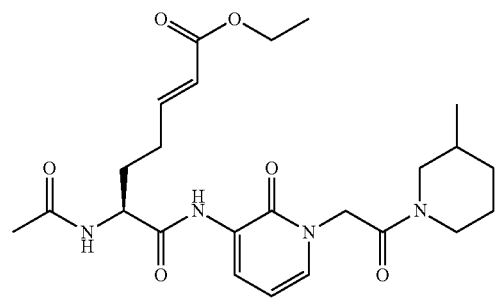

Molecular formula: C24H34N4O6
Molecular weight: 474.55

ESI-MS: 475.3 [M+H]$^+$

80

(2S,3R)-2-(2-(3-((S,E)-7-Ethoxy-2-(1-methyl-1H-imidazole-5-carboxamido)-7-oxohept-5-enamido)-2-oxopyridin-1(2H)-yl)acetamido)-3-methylpentanoic acid (A53)

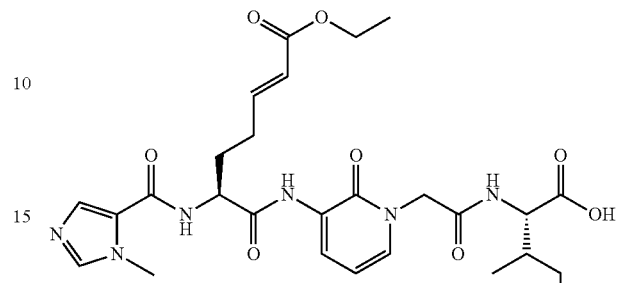

Molecular formula: C27H36N6O8
Molecular weight: 572.61

ESI-MS: 573.3 [M+H]$^+$ (S,E)-Ethyl 6-acetamido-7-(1-(2-(isobutylamino)-2-oxoethyl)-2-oxo-1,2-dihydropyridin-3-ylamino)-7-oxohept-2-enoate (A54)

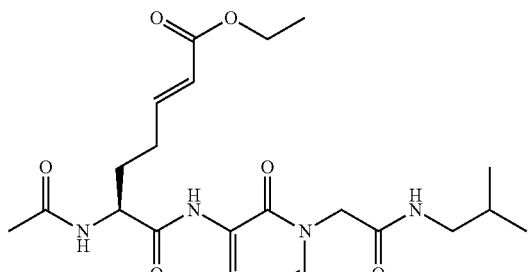

Molecular formula: C22H32N4O6
Molecular weight: 448.51

ESI-MS: 449.2 [M+H]$^+$ (6S,E)-Ethyl 6-acetamido-7-(1-(2-(3-methylbutan-2-ylamino)-2-oxoethyl)-2-oxo-1,2-dihydropyridin-3-ylamino)-7-oxohept-2-enoate (A55)

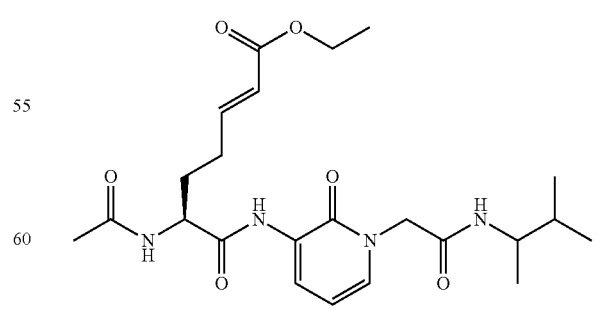

Molecular formula: C23H34N4O6
Molecular weight: 462.54

ESI-MS: 463.3 [M+H]$^+$

81

(S,E)-Ethyl 7-(1-(2-(isopentylamino)-2-oxoethyl)-2-oxo-1,2-dihydropyridin-3-ylamino)-7-oxo-6-(3-ureidopropanamido)hept-2-enoate (A56)

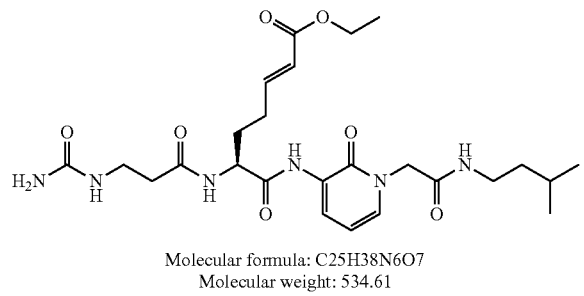 [SMILES: CCOC(=O)/C=C/CC[C@H](NC(=O)CCNC(N)=O)C(=O)Nc1cccn(CC(=O)NCCC(C)C)c1=O]

Molecular formula: C25H38N6O7
Molecular weight: 534.61

ESI-MS: 535.3 [M+H]+

(S,E)-Ethyl 6-acetamido-7-(1-(2-((S)-1-methoxy-3-methyl-1-oxobutan-2-ylamino)-2-oxoethyl)-2-oxo-1,2-dihydropyridin-3-ylamino)-7-oxohept-2-enoate (A57)

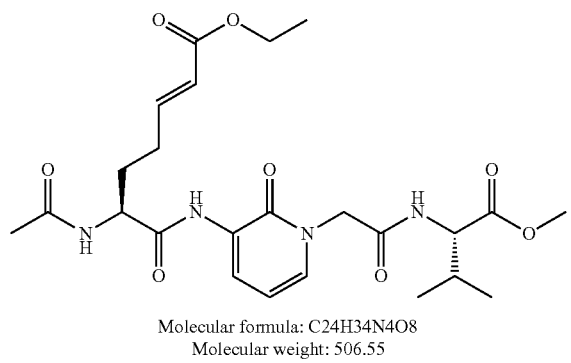 [SMILES: CCOC(=O)/C=C/CC[C@H](NC(C)=O)C(=O)Nc1cccn(CC(=O)N[C@H](C(=O)OC)C(C)C)c1=O]

Molecular formula: C24H34N4O8
Molecular weight: 506.55

ESI-MS: 507.2 [M+H]+

(2S,3R)-2-(2-(3-((S,E)-2-Benzamido-7-ethoxy-7-oxohept-5-enamido)-2-oxopyridin-1(2H)-yl)acetamido)-3-methylpentanoic acid (A59)

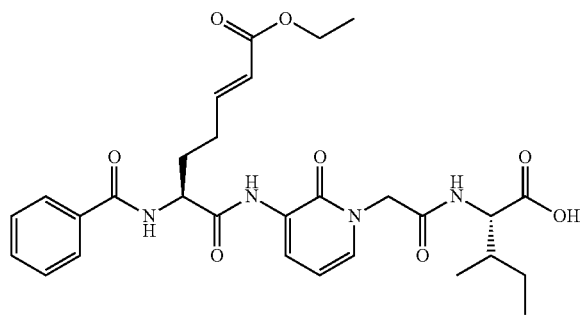

Molecular formula: C29H36N4O8
Molecular weight: 568.62

ESI-MS: 569.3 [M+H]+

82

(2S,3R)-2-(2-(3-((S,E)-7-Methoxy-2-(1-methyl-1H-imidazole-5-carboxamido)-7-oxohept-5-enamido)-2-oxopyridin-1(2H)-yl)acetamido)-3-methylpentanoic acid (A60)

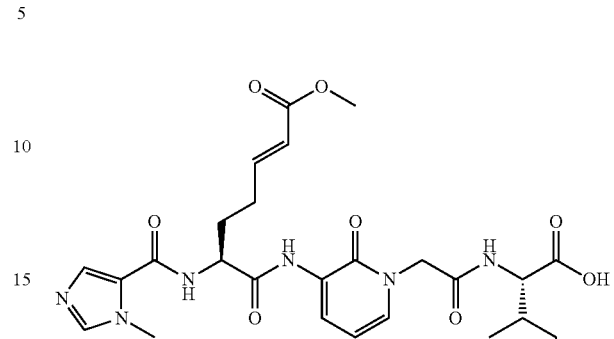

Molecular formula: C26H34N6O8
Molecular weight: 558.58

ESI-MS: 559.3 [M+H]+

(S,E)-Ethyl 6-acetamido-7-(1-(2-(2-ethylbutylamino)-2-oxoethyl)-2-oxo-1,2-dihydropyridin-3-ylamino)-7-oxohept-2-enoate (A62)

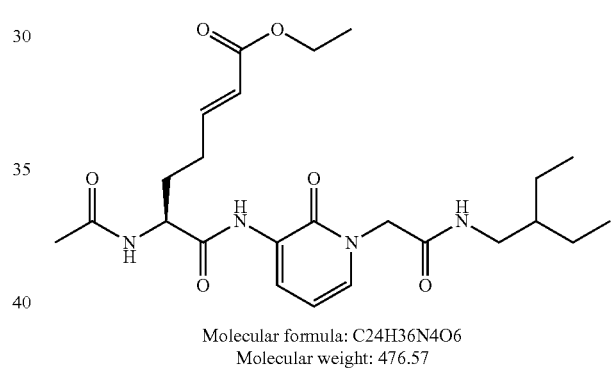

Molecular formula: C24H36N4O6
Molecular weight: 476.57

ESI-MS: 477.3 [M+H]+

(6S,E)-Methyl 6-acetamido-7-(1-(2-(3-methylpiperidin-1-yl)-2-oxoethyl)-2-oxo-1,2-dihydropyridin-3-ylamino)-7-oxohept-2-enoate (A64)

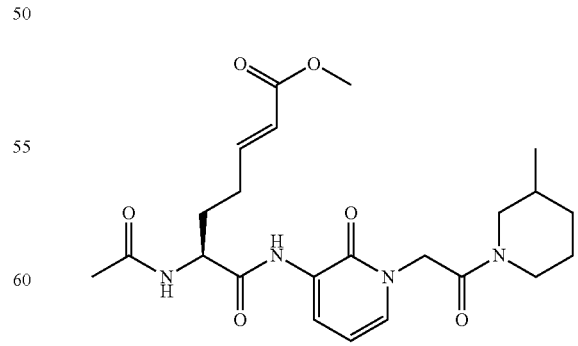

Molecular formula: C23H32N4O6
Molecular weight: 460.52

ESI-MS: 560.3 [M+H]+

83

(S,E)-Methyl 6-acetamido-7-oxo-7-(2-oxo-2-(4-(trifluoromethyl)piperidin-1-yl)ethyl)-1,2-dihydropyridin-3-ylamino)hept-2-enoate (A65)

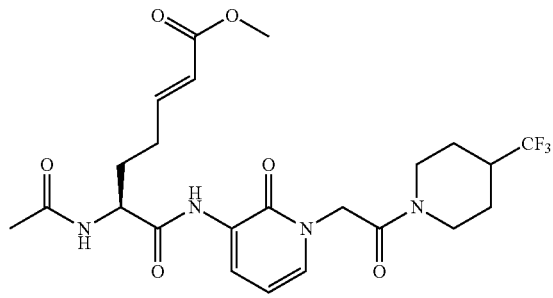

Molecular formula: C23H29F3N4O6
Molecular weight: 514.49

ESI-MS: 515.2 [M+H]+

(6S,E)-Methyl 6-acetamido-7-oxo-7-(2-oxo-1-(2-oxo-2-(3-(trifluoromethyl)piperidin-1-yl)ethyl)-1,2-dihydropyridin-3-ylamino)hept-2-enoate (A66)

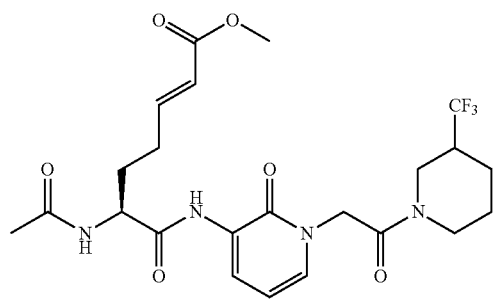

Molecular formula: C23H29F3N4O6
Molecular weight: 514.49

ESI-MS: 515.2 [M+H]+

(S,E)-Methyl 7-(1-(2-(2-ethylbutylamino)-2-oxoethyl)-2-oxo-1,2-dihydropyridin-3-ylamino)-6-(nicotinamido)-7-oxohept-2-enoate (A67)

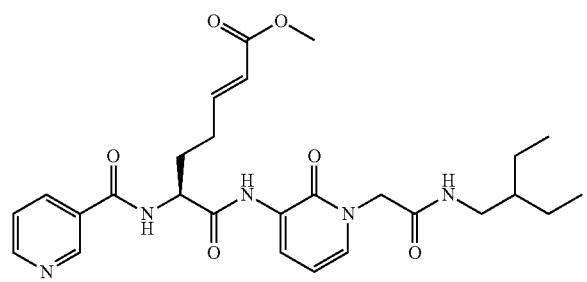

Molecular formula: C27H35N5O6
Molecular weight: 525.60

ESI-MS: 526.3 [M+H]+

84

(6S,E)-Methyl 6-(2-aminopropanamido)-7-(1-(2-(2-ethylbutylamino)-2-oxoethyl)-2-oxo-1,2-dihydropyridin-3-ylamino)-7-oxohept-2-enoate 2,2,2-trifluoroacetate (A68)

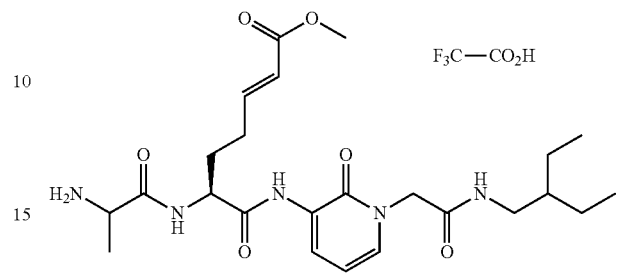

Molecular formula: C26H38F3N5O8
Molecular weight: 605.60

ESI-MS: 492.3 [M+H]+

(S,E)-Methyl 6-(2-aminoacetamido)-7-(1-(2-(2-ethylbutylamino)-2-oxoethyl)-2-oxo-1,2-dihydropyridin-3-ylamino)-7-oxohept-2-enoate 2,2,2-trifluoroacetate (A69)

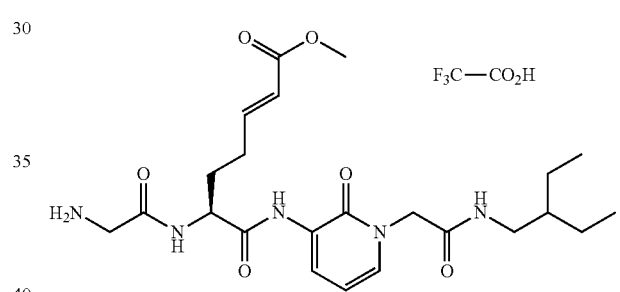

Molecular formula: C25H36F3N5O8
Molecular weight: 591.58

ESI-MS: 478.3 [M+H]+

(S,E)-Methyl 6-(2-aminobenzamido)-7-(1-(2-(2-ethylbutylamino)-2-oxoethyl)-2-oxo-1,2-dihydropyridin-3-ylamino)-7-oxohept-2-enoate 2,2,2-trifluoroacetate (A70)

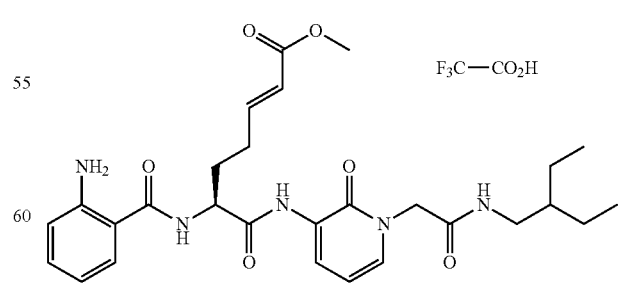

Molecular formula: C30H38N5O8
Molecular weight: 653.65

ESI-MS: 540.3 [M+H]+

(S,E)-Methyl 6-(3',6'-bis(dimethylamino)-3-oxo-3H-spiro[isobenzofuran-1,9'-xanthene]-5-ylcarbox-amido)-7-(1-(2-(2-ethylbutylamino)-2-oxoethyl)-2-oxo-1,2-dihydropyridin-3-ylamino)-7-oxohept-2-enoate (A71)

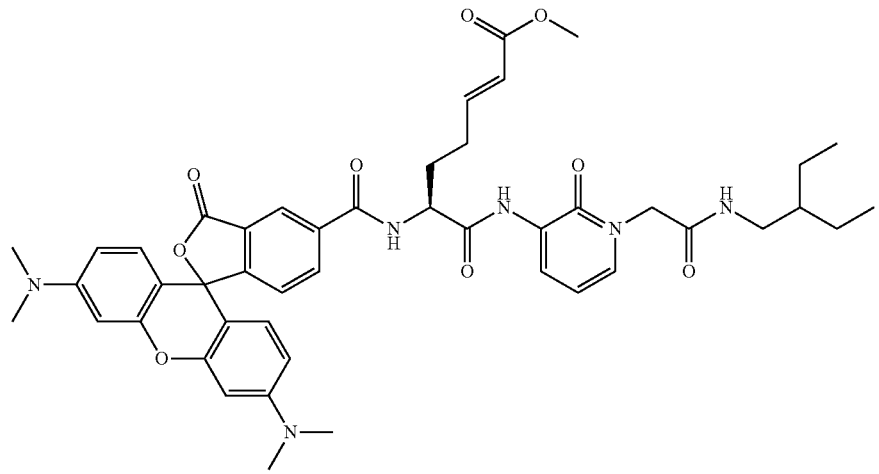

Molecular formula: C46H52N6O9
Molecular weight: 832.94

ESI-MS: 833.4 [M+H]+

(S,E)-Ethyl 6-acetamido-7-(1-(2-(isopentylamino)-2-oxoethyl)-2-oxo-1,2-dihydropyridin-3-ylamino)-7-oxohept-2-enoate (A72)

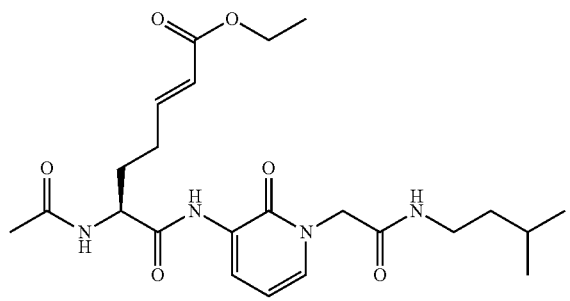

Molecular formula: C23H43N4O6
Molecular weight: 462.54

ESI-MS: 463.3 [M+H]+

(S,E)-Methyl 6-acetamido-7-(1-(2-(isopentylamino)-2-oxoethyl)-2-oxo-1,2-dihydropyridin-3-ylamino)-7-oxohept-2-enoate (A73)

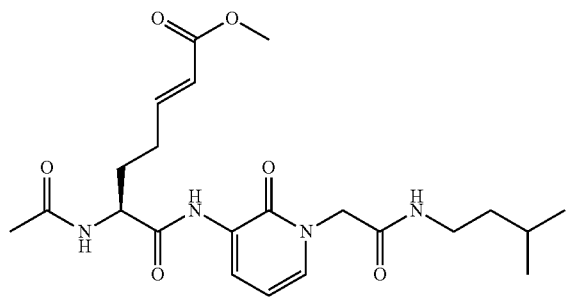

Molecular formula: C22H32N4O6
Molecular weight: 448.51

ESI-MS: 449.2 [M+H]+

(S,E)-Ethyl 7-(1-(2-(2-ethylbutylamino)-2-oxo-ethyl)-2-oxo-1,2-dihydropyridin-3-ylamino)-6-(1-methyl-1H-imidazole-5-carboxamido)-7-oxohept-2-enoate (A74)

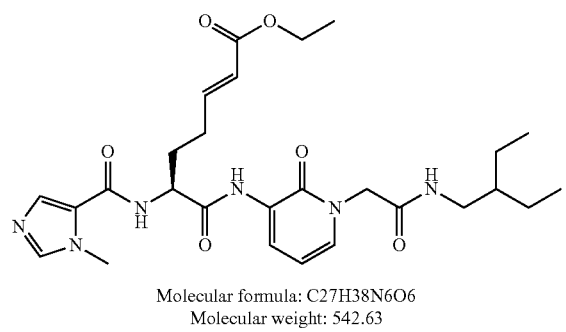 [SMILES: CCOC(=O)/C=C/CC[C@H](NC(=O)c1cncn1C)C(=O)Nc1cccn(CC(=O)NCC(CC)CC)c1=O]

Molecular formula: C27H38N6O6
Molecular weight: 542.63

ESI-MS: 543.3 [M+H]+

(2S,3R)-2-(2-(3-((S,E)-2-Benzamido-7-methoxy-7-oxohept-5-enamido)-2-oxopyridin-1(2H)-yl)acet-amido)-3-methylpentanoic acid (A75)

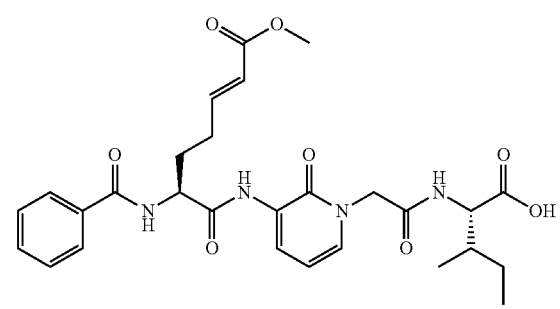

Molecular formula: C28H34N4O8
Molecular weight: 554.59

ESI-MS: 555.2 [M+H]+

(R,E)-Methyl 7-(1-(2-(2-ethylbutylamino)-2-oxo-ethyl)-2-oxo-1,2-dihydropyridin-3-ylamino)-6-(1-methyl-1H-imidazole-5-carboxamido)-7-oxohept-2-enoate (A76)

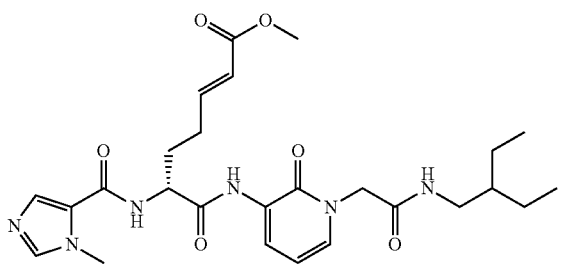

Molecular formula: C26H36N6O6
Molecular weight: 528.60

ESI-MS: 529.3 [M+H]$^+$ (S,E)-Methyl 6-acetamido-7-(1-(2-(2-ethylbutylamino)-2-oxoethyl)-2-oxo-1,2-dihydropyridin-3-ylamino)-7-oxohept-2-enoate (A79)

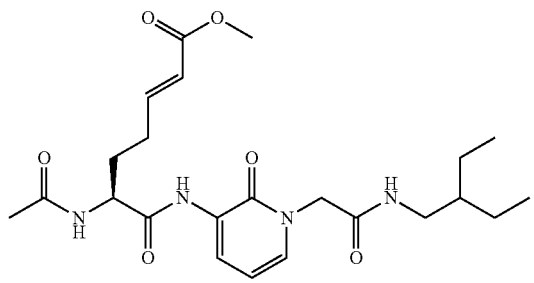

Molecular formula: C23H34N4O6
Molecular weight: 462.54

ESI-MS: 463.3 [M+H]$^+$

9. Inhibitory Effect of the Compounds According to the Invention

General Method for Inactivation of Human Tissue Transglutaminase

250 μg lyophilized His tagged recombinant human tissue transglutaminase (His$_6$-rh-TG2, Zedira product T002) are reconstituted by adding 150 μl water (resulting buffer 50 mM NaH$_2$PO$_4$, 150 mM NaCl, pH=8.0).

A 10 mM inhibitor stock solution in DMSO is prepared and is diluted with buffer (50 mM Tris-HCl, 10 mM CaCl$_2$, 5 mM DTT, pH=7.5) each to the twentyfold of the concentration desired in the preparation (but at least 1/50 dilution resulting in a 2% DMSO concentration).

900 μl of an assay-solution consisting of 55.56 mM Tris, 11.11 mM CaCl$_2$, 0.11% PEG$_{8000}$, 5.56 mM DTT, 5.56 mM glycine methyl ester and 50 μM Abz-APE(CAD-DNP)QEA-OH, (Zedira product A102; patent No.: EP 1781807B1), pH=7.5 are added to a cuvette and heated in a measuring cell of a spectrophotometer to 37° C. 50 μl of the particular inhibitor solution are added to this solution (resulting in a concentration of less than 0.2% DMSO in the mixture).

7 μl of the transglutaminase solution reconstituted above are diluted with 51 μl buffer (50 mM Tris, 100 mM NaCl, 5 mM DTT, pH=7.5). 50 μl of this enzyme solution (10 μg His$_6$-rhTG2) are added to the assay-solution containing the particular inhibitor concentration. It is incubated 5 min at 37° C. before measuring starts ($\lambda_{exc}$=313 nm and $\lambda_{em}$=418 nm, t=15 to 30 min).

The comparative determination of different transglutaminases to determine the selectivity was made with casein and dansylcadaverine as substrates. Therefore, the kit T036 (Zedira, Darmstadt; Refs: Lorand et al, Anal Biochem, 1971, 44:221-31) as well as transglutaminase products T009 (transglutaminase 1), T012 (transglutaminase 3), T021 (transglutaminase 6) and T027 (plasma transglutaminase, factor XIII) are used. Therefore, two different IC$_{50}$ values for the compounds are given.

The evaluation of the resulting enzyme activity is done using the slope of the straight line obtained by the increase in fluorescence.

To determine the non-inhibited enzyme activity, DMSO instead of inhibitor stock solution is used. IC$_{50}$ values are determined by plotting the resulting enzyme activity against the logarithm of the inhibitor concentration. IC$_{50}$ is defined as the concentration of inhibitor resulting in 50% of enzyme activity.

The inhibitory activity of the inventive compounds in regard to tissue transglutaminase (TG2) is shown in the following table using IC$_{50}$-values.

| compound | IC$_{50}$ TG2 |
|---|---|
| A1 | 100 nM |
| A2 | 100 nM |
| A3 | 96 nM |
| A4 | 119 nM |
| A5 | 130 nM |
| A6 | 532 nM |
| A7 | 126 nM |
| A8 | 251 nM |
| A9 | 708 nM |
| A10 | 73 nM |
| A11 | 104 nM |
| A12 | 84 nM |
| A13 | 83 nM |
| A14 | 137 nM |
| A15 | 92 nM |
| A16 | 104 nM |
| A17 | 63 nM |
| A18 | 175 nM |
| A19 | 80 nM |
| A20 | 202 nM |
| A21 | 111 nM |
| A22 | 133 nM |
| A23 | 475 nM |
| A24 | 173 nM |
| A25 | 4.8 μM |
| A26 | 5.4 μM |
| A27 | 5.2 μM |
| A28 | 32 nM |
| A29 | 32 nM |
| A30 | 116 nM |
| A31 | 124 nM |
| A32 | 194 nM |
| A33 | 493 nM |
| A34 | 640 nM |
| A35 | 55 nM |
| A36 | 88 nM |
| A37 | 340 nM |
| A38 | 175 nM |
| A39 | 115 nM |
| A40 | 131 nM |
| A41 | 166 nM |
| A42 | 147 nM |

-continued

| compound | IC$_{50}$ TG2 |
|---|---|
| A43 | 145 nM |
| A44 | 240 nM |
| A45 | 1.23 µM |
| A46 | 3.3 µM |
| A47 | 480 nM |
| A48 | 1.7 µM |
| A49 | 1.8 µM |
| A50 | 119 nM |
| A51 | 166 nM |
| A52 | 0.7 µM |
| A53 | 60 nM |
| A54 | 191 nM |
| A55 | 153 nM |
| A56 | 139 nM |
| A57 | 84 nM |
| A58 | 76 nM |
| A59 | 43 nM |
| A60 | 54 nM |
| A61 | 25 nM |
| A62 | 93 nM |
| A63 | 45 nM |
| A64 | 141 nM |
| A65 | 132 nM |
| A66 | 310 nM |
| A67 | 55 nM |
| A68 | 53 nM |
| A69 | 71 nM |
| A70 | 81 nM |
| A71 | 97 nM |
| A72 | 1.15 µM |
| A73 | 157 nM |
| A74 | 554 nM |
| A75 | 136 nM |
| A76 | 54.7 µM |
| A77 | 469 nM |
| A78 | 627 nM |
| A79 | 34 nM |

The selectivity of the inhibitory activity of selected compounds of the invention in regard to the tissue transglutaminase (TG2) is given on the basis of IC$_{50}$ values against the transglutaminases TG1, TG6, TG3 and FXIII in the table below. It should be noted that it was measured here against casein as substrate, which is why other apparent inhibition values (IC$_{50}$ value) result.

| A7 | IC$_{50}$ | A19 | IC$_{50}$ | A24 | IC$_{50}$ |
|---|---|---|---|---|---|
| TG2 | 3.6 µM | TG2 | 2.39 µM | TG2 | 7.5 µM |
| TG1 | 28.8 µM | TG1 | 96.0 µM | TG1 | 91.9 µM |
| TG6 | 51.0 µM | TG6 | 54.3 µM | TG6 | 38.5 µM |
| TG3 | 84.1 µM | TG3 | 128 µM | TG3 | 119 µM |
| FXIII | 105 µM | FXIII | 81.1 µM | FXIII | 133 µM |

| A29 | IC$_{50}$ | A30 | IC$_{50}$ | A35 | IC$_{50}$ |
|---|---|---|---|---|---|
| TG2 | 0.4 µM | TG2 | 3.26 µM | TG2 | 1.0 µM |
| TG1 | 28.1 µM | TG1 | 113 µM | TG1 | 87.1 µM |
| TG6 | 83.3 µM | TG6 | 32.8 µM | TG6 | 21.3 µM |
| TG3 | 70.9 µM | TG3 | 69.0 µM | TG3 | 95.8 µM |
| FXIII | 67.4 µM | FXIII | 90.9 µM | FXIII | 70.7 µM |

| A42 | IC$_{50}$ | A53 | IC$_{50}$ | A58 | IC$_{50}$ |
|---|---|---|---|---|---|
| TG2 | 7.1 µM | TG2 | 833 nM | TG2 | 1.54 µM |
| TG1 | 86.0 µM | TG1 | 68.9 µM | TG1 | 97.5 µM |
| TG6 | 36.7 µM | TG6 | 26.2 µM | TG6 | 66.0 µM |
| TG3 | 104 µM | TG3 | 72.6 µM | TG3 | 109 µM |
| FXIII | 109 µM | FXIII | 77.7 µM | FXIII | 120 µM |

| A59 | IC$_{50}$ | A60 | IC$_{50}$ | A61 | IC$_{50}$ |
|---|---|---|---|---|---|
| TG2 | 461 nM | TG2 | 112 nM | TG2 | 79 nM |
| TG1 | 37.1 µM | TG1 | 31.1 µM | TG1 | 15.3 µM |
| TG6 | 9.3 µM | TG6 | 11.5 µM | TG6 | 4.3 µM |
| TG3 | 41.1 µM | TG3 | 42.3 µM | TG3 | 17.6 µM |
| FXIII | 79.6 µM | FXIII | 73.2 µM | FXIII | 63.4 µM |

| A62 | IC$_{50}$ | A63 | IC$_{50}$ | A64 | IC$_{50}$ |
|---|---|---|---|---|---|
| TG2 | 1.96 µM | TG2 | 218 nM | TG2 | 3.0 µM |
| TG1 | 133 µM | TG1 | 51.8 µM | TG1 | 122 µM |
| TG6 | 47.0 µM | TG6 | 31.5 µM | TG6 | 109 µM |
| TG3 | 99.7 µM | TG3 | 73.9 µM | TG3 | 125 µM |
| FXIII | 122 µM | FXIII | 89.0 µM | FXIII | 120 µM |

| A65 | IC$_{50}$ | A79 | IC$_{50}$ |
|---|---|---|---|
| TG2 | 2.9 µM | TG2 | 397 nM |
| TG1 | 120 µM | TG1 | 80.7 µM |
| TG6 | 37.7 µM | TG6 | 47.8 µM |
| TG3 | 100 µM | TG3 | 59.6 µM |
| FXIII | 156 µM | FXIII | 78.2 µM |

10. Detection of Tissue Transglutaminase (TG2)-Inhibition

30 BALB/c mice were divided into 4 groups: control group (3 animals) and 3 inhibitor groups (9 animals each). After starving the animals for 6 hours, 500 µl inhibitor solution A63 (ZED1227), A29 (ZED1098) or A61 (ZED1219)) or buffer were administered orally by gavage. The dose per animal was 5 mg/kg body weight. After 30 min the animals were given again access to food. After 3, 8 or 24 hours each 3 mice per inhibitor group were sacrificed and the small intestine was dissected.

After 24 h the small intestine of the control mice was dissected and cryoconserved.

Using the microtome cryosections of the small intestine preparations were made. The quality of the sections was ensured by hematoxylin/eosin staining.

The respective methods are known to the skilled person.

This was followed by the staining protocol described below: The cryosections were fixed in acetone (100%, ice cold) for 10 min, and subsequently blocked with 1% BSA in 0.1 M Tris-HCl. After a washing step (1% BSA in PBS buffer), incubation was carried out with 4 µg/ml of the TG2 substrate biotinyl-TVQQEL (Zedira, product number B001) in the presence of 5 mM CaCl$_2$ for 2 h at room temperature. The reaction was stopped with 25 mM EDTA. After one further washing, blocking, and washing step, the primary antibody against human TG2 was added (Zedira, product number A018, 25 µg/ml) and incubated for one hour at room temperature. After four wash steps, streptavidin-FITC (2 µg/ml, streptavidin-fluorescein-isothiocyanate) and Cy3-labeled goat anti-rabbit IgG antibodies (22.5 µg/ml) were added and incubated in the dark at room temperature for 40 min. TG2 was thus visible in the fluorescence microscope as red color (Cy3), whereas biotinyl-TVQQEL incorporated by transglutaminase activity was visualized by green staining (FITC). The superposition of both images led to a yellow color when active transglutaminase was present.

Within the evaluable sections of the control mice no inhibition of TG2 was present, this means, up to the tips of the villi active TG2 could be detected. In contrast, the activity of the TG2 in the sections of mice to which the inhibitor was administered decreased significantly. Particularly in sections of mice sacrificed after 24 h, the TG2 inhibition was detectable up to the entire mucosa of the small intestine.

The experiments show that the tested inhibitors are able in vivo to inhibit the TG2 in the mucosa of the small intestine.

11. Ex Vivo-Testing of Inhibitors A63 (ZED1227) and A61 (ZED1219)

After fixation, sections (approximately 5-7 µM thick) of a control mouse of example 7 were pre-incubated with 0.2 mg/ml, 0.02 mg/ml, 0.002 mg/ml and 0.0 mg/ml inhibitor (A63 (ZED1227) or A61 (ZED1219)). Then the staining protocol as described in example 10 was carried out. In the control sections with 0.0 mg/ml inhibitor yellow staining in the mucosa of the small intestinal was detected, which is due to active TG2. After addition of inhibitor, with 0.002 µg/ml inhibitor transglutaminase activity was still detected. At the higher concentrations of inhibitor TG2 was completely inhibited. The results show that A63 (ZED1227) as well as A61 (ZED1219) are able to inhibit TG2 in tissue sections.

12. Determination of Cytotoxicity of Transglutaminase-Inhibitors

Huh 7 (human hepatome-cell line) and CaCo2 (human colon carcinoma-cell line) were seeded to 96 well plates in Dulbecco's Modified Eagle's Medium (DMEM)/10% fetal calf serum (FCS) and cultivated. The method is known to the skilled person.

After one hour the inhibitors A63 (ZED1227), A29 (ZED1098) and A61 (ZED1219) were added in the concentrations 0.1 µM to 1 µM. The determination of the proliferation was carried out using the Cell Proliferation ELISA, BrdU (Roche 11 647 229 001): 24 hours after incubation of the cells with the inhibitor BrdU was added. The colorimetric development of the test was made after further 48 hours according to manufacturer's information. The extinction was measured at 450 nm. For determination of the metabolic activity using the EZ4U-Assay (Biomedica B1-5000) the tetrazolium substrate was added to the cells 48 hours after addition of the inhibitor. The capacity for reaction of the cells was measured every hour over a period of 4 hours at 450 nm against a reference filter of 630 nm. DMEM without inhibitor was added as reference in both experiments, as positive control cycloheximide (2.5 µg/ml) and camptothecin (0.2 µg/ml). While the two positive controls result in a significant reduction in proliferation and metabolic activity, both, of the CaCo2 and the Huh7 cells, no effect on metabolic activity and proliferation could be measured with the tested inhibitors A63 (ZED1227), A29 (ZED1098) and A61 (ZED1219) up to the highest measured concentration of 1 mM.

The inhibitors A63 (ZED1227), A29 (ZED1098) and A61 (ZED1219) therefore show no cytotoxic activity.

The invention claimed is:

1. A compound of the following general formula (I):

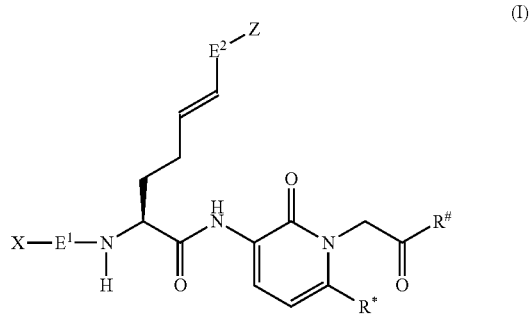

wherein $E^1$ and $E^2$ are each independently —CO— or —$SO_2$—;

R* is selected from the group consisting of —H, —$CH_3$, —$C_2H_5$, —$C_3H_7$, —CH($CH_3$)$_2$, and —$C_4H_9$;

R# is selected from the group consisting of NYY', —OH, —OY, —NH—$CH_2$—COOH, —NH—CH($CH_3$)—COOH, —NH—CH($CH_2CH_2SCH_3$)—COOH, —NH—CH($CH_2OH$)—COOH, —NH—CH($CH_2SH$)—COOH, —NH—CH($CH_2CONH_2$)—COOH, —NH—CH($CH_2CH_2CONH_2$)—COOH, —NH—CH($CH_2CH(CH_3)_2$)—$CH_2$COOH, —NH—CH($CH_2$Ph)-COOH, —NH—CH($CH_2$COOH)—COOH, —NH—CH($CH_2CH_2$COOH)—COOH, —NH—CH(COOH)—CH($CH_3$)$_2$, —NH—CH(COOH)—$CH_2CH(CH_3)_2$, —NH—$CH_2$—COOY', —NH—CH($CH_3$)—COOY', —NH—CH($CH_2CH_2SCH_3$)—COOP', —NH—CH($CH_2OH$)—COOY', —NH—CH($CH_2SH$)—COOY', —NH—CH($CH_2CONH_2$)—COOY', —NH—CH($CH_2CH_2CONH_2$)—COOY', —NH—CH($CH_2CH(CH_3)_2$)—$CH_2$COOY', —NH—CH($CH_2$Ph)-COOY', —NH—CH($CH_2$COOH)—COOY', —NH—CH($CH_2$COOY')—COOH, —NH—CH($CH_2$COOY)—COOY', —NH—CH($CH_2CH_2$COOY)—COOY', —NH—CH(COOH)—CH($CH_3$)$_2$, —NH—CH(COOH)—$CH_2CH(CH_3)_2$,

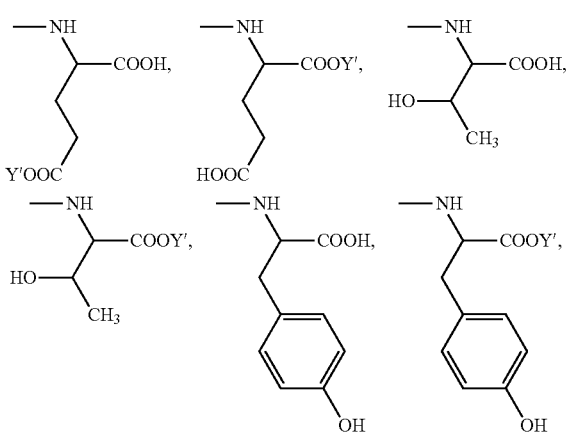

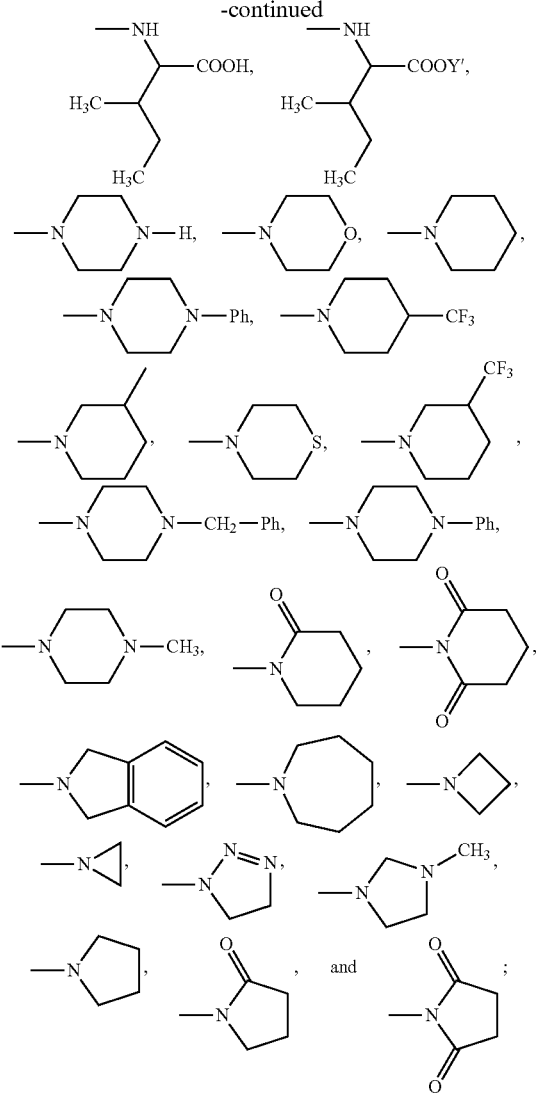

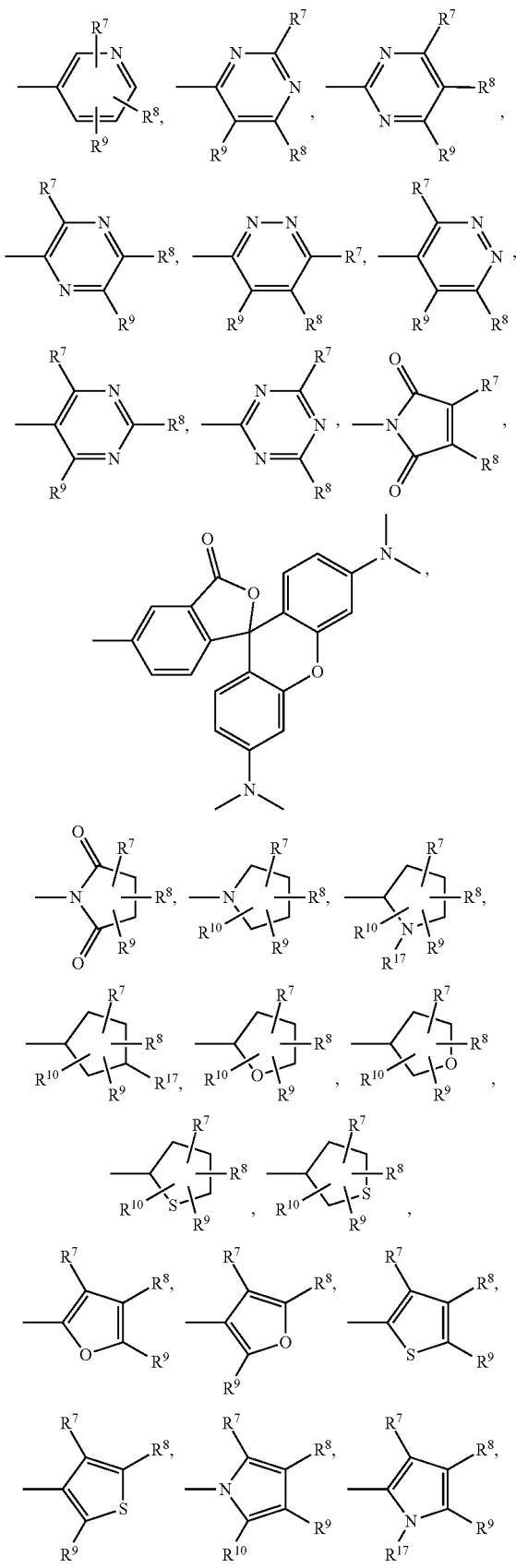

Y is selected from the group consisting of: —CH$_2$R$^1$, —CHR$^1$—CH$_2$R$^2$, —CHR$^1$—CHR$^2$—CH$_2$R$^3$, —CHR$^1$—CHR$^2$—CHR$^3$—CH$_2$R$^4$, —CHR$^1$—CHR$^2$—CHR$^3$—CHR$^4$—CH$_2$R$^5$, —CHR$^1$—CHR$^2$—CHR$^3$—CHR$^4$—CHR$^5$—CH$_2$R$^6$ Y', R$^{17}$, R$^{18}$, R$^{19}$, and R$^{20}$ are each independently selected from the group consisting of: —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, and —C$_2$H$_4$—CH(CH$_3$)$_2$;

X is selected from the group consisting of —CR$^7$R$^8$R$^9$, —CH$_2$R$^7$, —CHR$^7$—CH$_2$R$^8$, —O—CH$_2$R$^7$, —O—CR$^7$R$^8$R$^9$, —O—CHR$^7$—CH$_2$R$^8$,

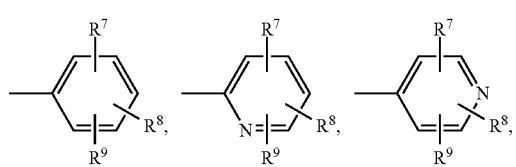

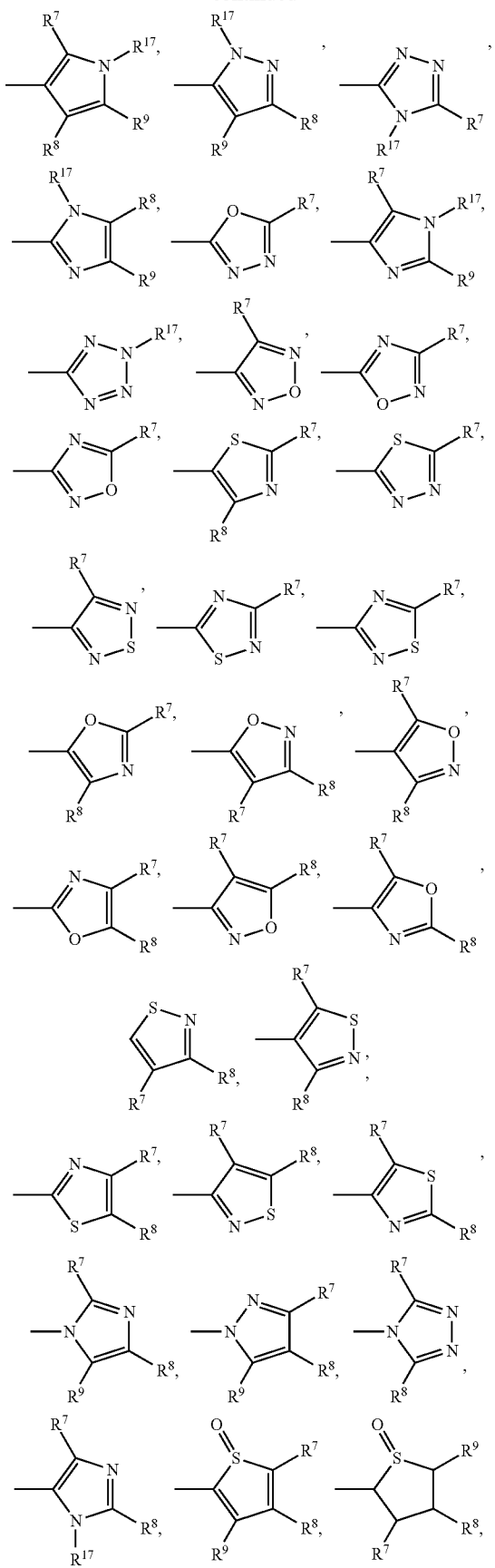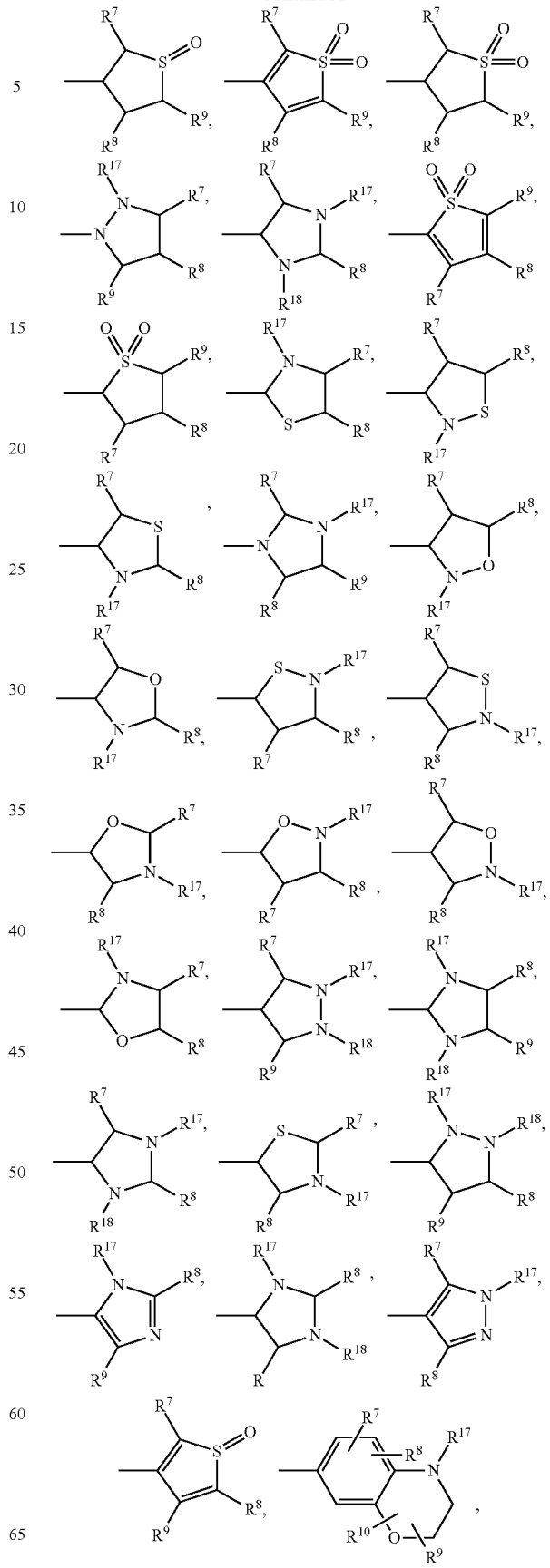

-continued

[Chemical structures with R7, R8, R9, R10, R17, R18 substituents on various bicyclic ring systems containing O, S, N heteroatoms]

Z is selected from the group consisting of: —CH₃, —C₂H₅, —C₃H₇, —CH(CH₃)₂, —C₄H₉, -Ph, —CH₂-Ph, —OCH₃, —OC₂H₅, —OC₃H₇, —OCH(CH₃)₂, —OC₄H₉, —OPh, —OCH₂-Ph, —OCH=CH₂, and —OCH₂—CH=CH₂;

R¹, R², R³, R⁴, R⁵, R⁶, R⁷, R⁸, R⁹, and R¹⁰ are each independently selected from the group consisting of: —H, —OH, —OCH₃, —OC₂H₅, —OC₃H₇, —O-cyclo-C₃H₅, —OCH(CH₃)₂, —OC(CH₃)₃, —OC₄H₉, —OPh, —OCH₂-Ph, —OCPh₃, —SH, —NO₂, —F, —Cl, —Br, —I, —N₃, —CN, —OCN, —NCO, —SCN, —NCS, —CHO, —COCH₃, —COC₂H₅, —COC₃H₇, —CO-cyclo-C₃H₅, —COCH(CH₃)₂, —COC(CH₃)₃, —COOH, —COCN, —COOCH₃, —COOC₂H₅, —COOC₃H₇, —COO-cyclo-C₃H₅, —COOCH(CH₃)₂, —COOC(CH₃)₃, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —NHCOCH₃, —NHCOC₂H₅, —NHCOC₃H₇, —NHCO-cyclo-C₃H₅, —NHCO—CH(CH₃)₂, —NHCO—C(CH₃)₃, —NHCO—OCH₃, —NHCO—OC₂H₅, —NHCO—OC₃H₇, —NHCO—O-cyclo-C₃H₅, —NHCO—OCH(CH₃)₂, —NHCO—OC(CH₃)₃, —NH₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —N[C(CH₃)₃]₂, —SOCH₃, —SOC₂H₅, —SOC₃H₇, —SO-cyclo-C₃H₅, —SOCH(CH₃)₂, —SOC(CH₃)₃, —SO₂CH₃, —SO₂C₂H₅, —SO₂C₃H₇, —SO₂-cyclo-C₃H₅, —SO₂CH(CH₃)₂, —SO₂C(CH₃)₃, —SO₃H, —SO₃CH₃, —SO₃C₂H₅, —SO₃C₃H₇, —SO₃-cyclo-C₃H₅, —SO₃CH(CH₃)₂, —SO₃C(CH₃)₃, —SO₂NH₂, —OCF₃, —OC₂F₅, —O—COOCH₃, —O—COOC₂H₅, —O—COOC₃H₇, —O—COO-cyclo-C₃H₅, —O—COOCH(CH₃)₂, —O—COOC(CH₃)₃, —NH—CO—NH₂, —NH—CO—NHCH₃, —NH—CO—NHC₂H₅, —NH—CO—NHC₃H₇, —NH—CO—NH-cyclo-C₃H₅, —NH—CO—NH[CH(CH₃)₂], —NH—CO—NH[C(CH₃)₃], —NH—CO—N(CH₃)₂, —NH—CO—N(C₂H₅)₂, —NH—CO—N(C₃H₇)₂, —NH—CO—N(cyclo-C₃H₅)₂, —NH—CO—N[CH(CH₃)₂]₂, —NH—CO—N[C(CH₃)₃]₂, —NH—C S-Nh₂, —NH—C S-NhCH₃, —NH—C S-NhC₂H₅, —NH—C S-NhC₃H₇, —NH—CS—NH-cyclo-C₃H₅, —NH—C S-Nh[CH(CH₃)₂], —NH—C S-Nh[C(CH₃)₃], —NH—CS—N(CH₃)₂, —NH—CS—N(C₂H₅)₂, —NH—CS—N(C₃H₇)₂, —NH—CS—N(cyclo-C₃H₅)₂, —NH—CS—N[CH(CH₃)₂]₂, —NH—CS—N[C(CH₃)₃]₂, —NH₂*HOOCCF₃, —CH₂F, —CF₂Cl, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, cyclo-C₃H₅, cyclo-C₄H₇, cyclo-c₅H₉, cyclo-C₆H₁₁, cyclo-C₇H₁₃, cyclo-C₈H₁₅, -Ph, —CH₂-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂, —C₇H₁₅, —C₈H₁₇, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, CH₂CH=CH—CH=CH₂, —CH=CH CH=CH—CH₃, CH₂NH₂, —CH₂OH, —CH₂SH, —CH₂—CH₂NH₂, —CH₂—CH₂SH, —C₆H₄—OCH₃, —C₆H₄—OH, —CH₂—C₆H₄—OCH₃, —CH₂—CH₂OH, —CH₂—OCH₃, —CH₂—C₆H₄—OCH₃, —CH₂—C₆H₄—OH, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇,
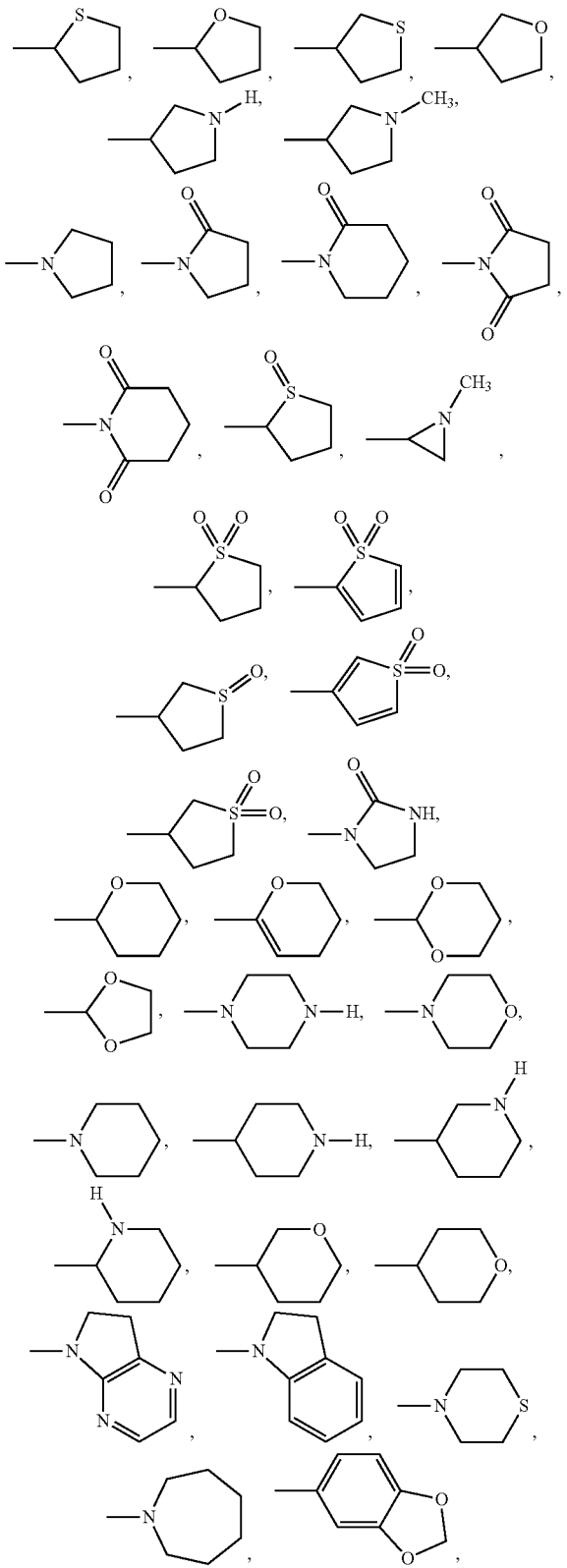
-continued
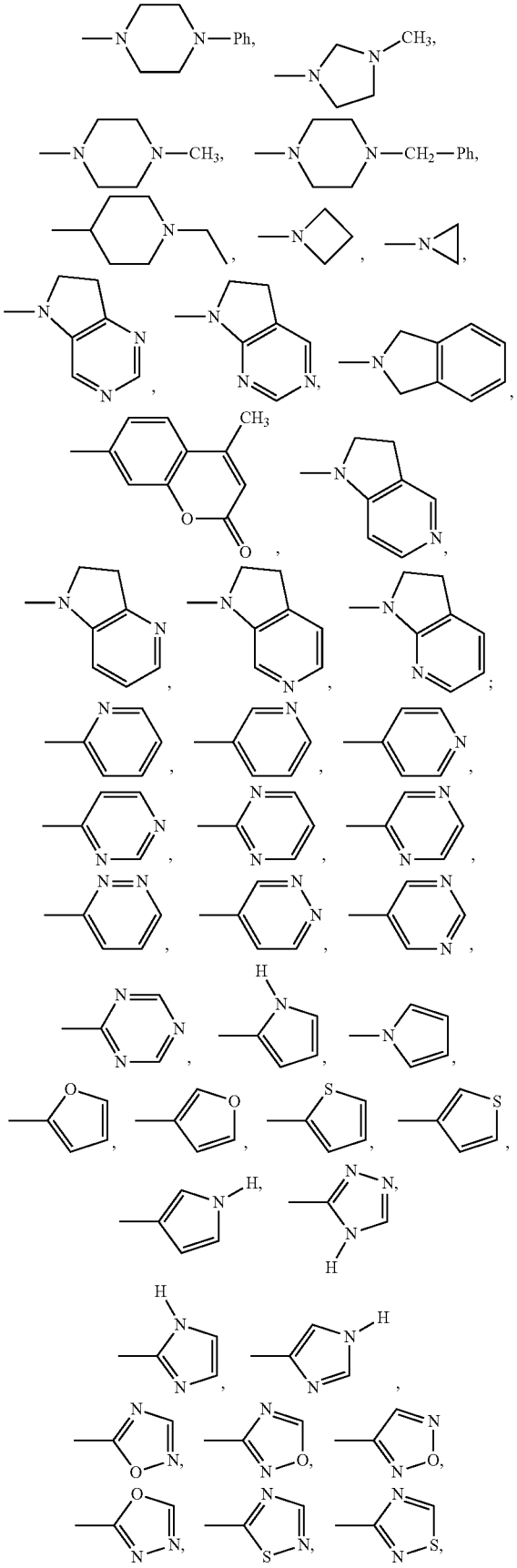

101
-continued
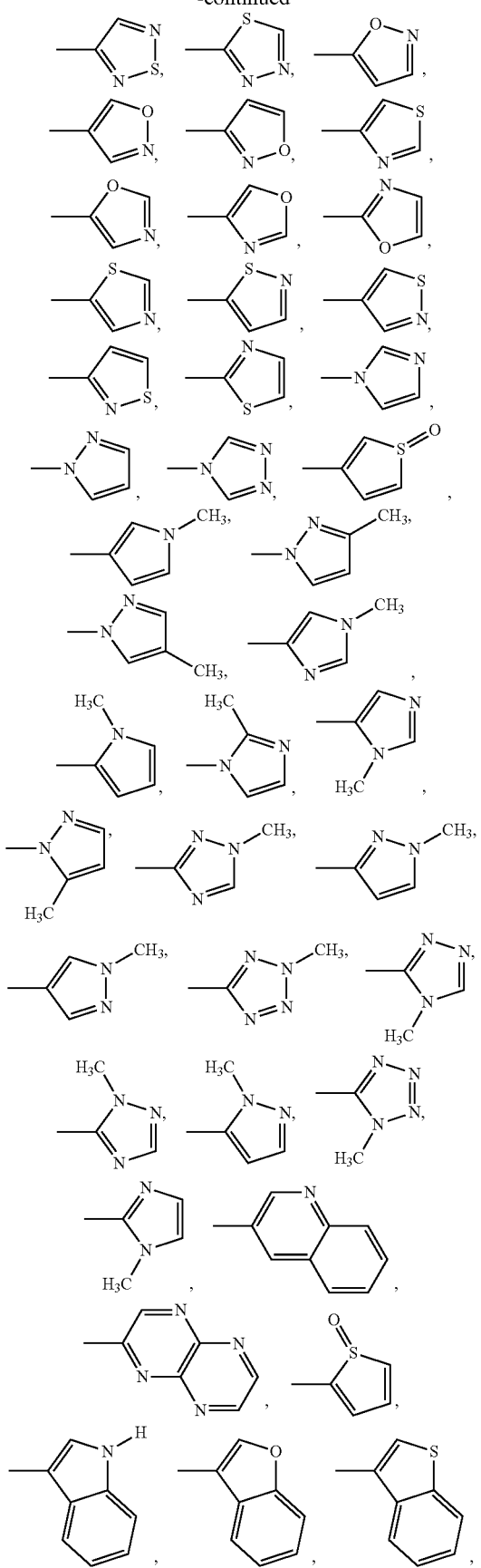
102
-continued
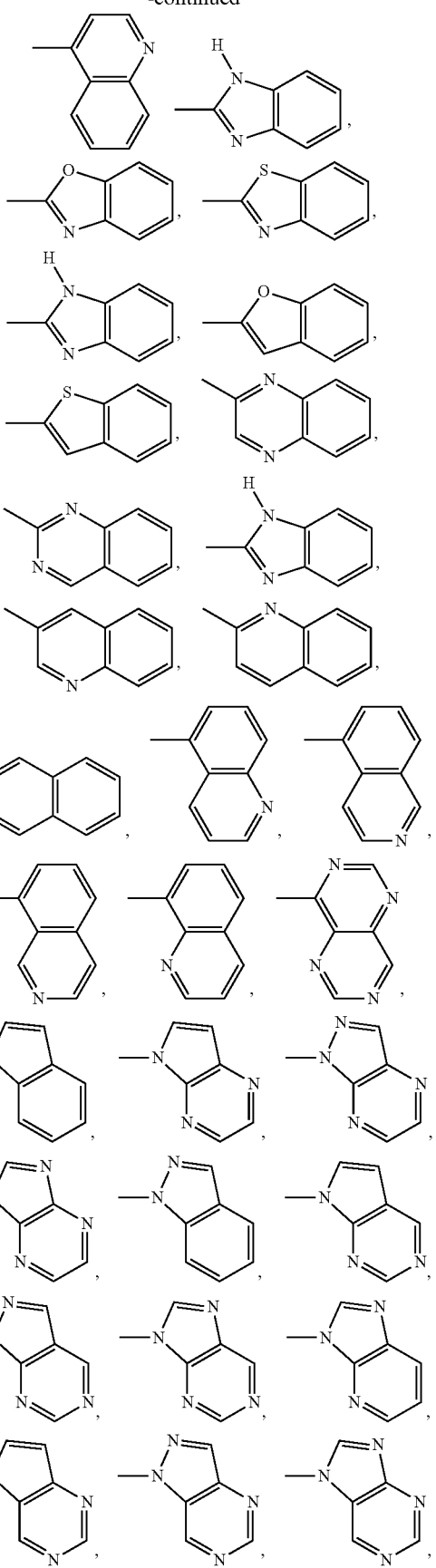

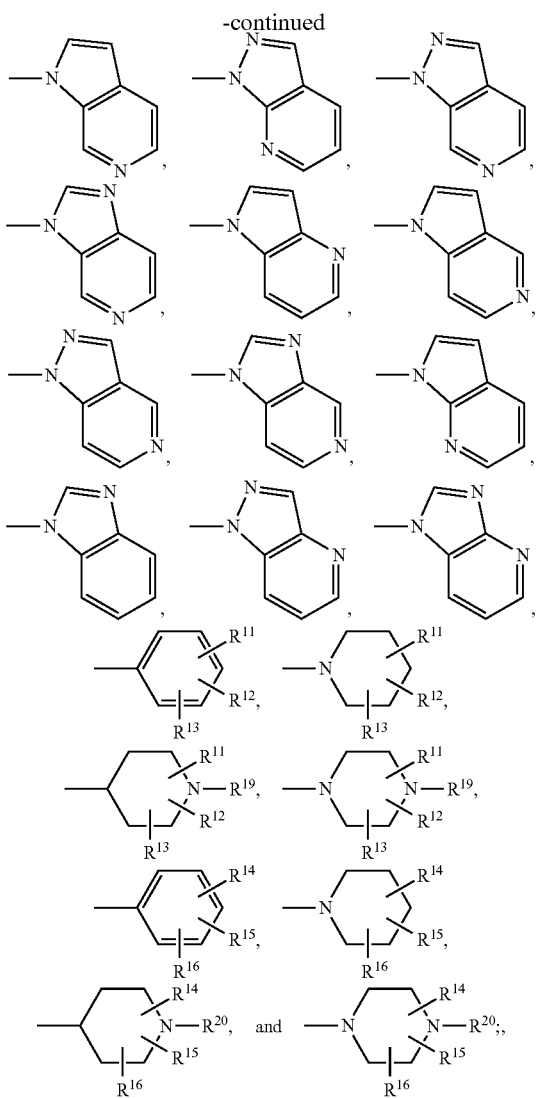

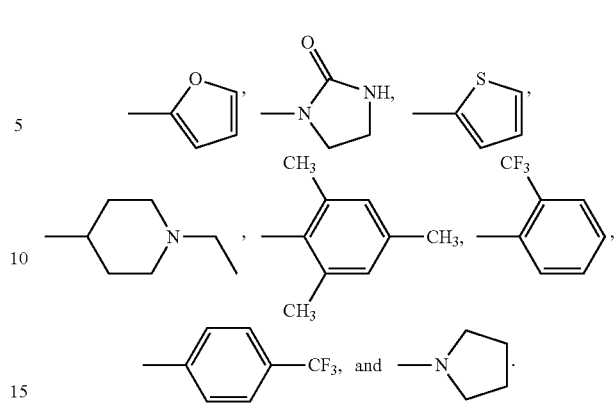

$R^{11}$, $R^{12}$, $R^{13}$, $R^{14}$, $R^{15}$, and $R^{16}$ are each independently selected from the group consisting of: —H, —NH$_2$, —OH, —OCH$_3$, —OC$_2$H$_5$, —OC$_3$H$_7$, —OCF$_3$, —CF$_3$, —F, —Cl, —Br, —I, —CH$_3$, —C$_2$H$_5$, —C$_3$H$_7$, —CH(CH$_3$)$_2$, -Ph, and —CN; and stereoisomeric forms, E/Z isomers, enantiomers, mixtures of enantiomers, diastereomers, mixtures of diastereomers, racemates, tautomers, anomers, keto-enol-forms, betaine forms, prodrugs, solvates, hydrates, and pharmaceutically acceptable salts of the above mentioned compounds.

2. The compound of claim 1, wherein
Z is —OCH$_3$, —OCH$_2$CH$_3$, —OCH(CH$_3$)$_2$, or —OCH$_2$-Ph;
R* is —H or —CH$_3$; and
R$^\#$ represents —NHY.

3. The compound of claim 2, wherein
Y is selected from the group consisting of —CH$_2$R$^1$, —CHR$^1$—CH$_2$R$^2$, —CHR$^1$—CHR$^2$—CH$_2$R$^3$, —CHR$^1$—CHR$^2$—CHR$^3$—CH$_2$R$^4$, and —CHR$^1$—CHR$^2$—CHR$^3$—CHR$^4$—CH$_2$R$^5$; and
R$^1$, R$^2$, R$^3$, R$^4$, and R$^5$ are each independently selected from the group consisting of: —COOH, —COOCH$_3$, —N(CH$_3$)$_2$, —N(C$_2$H$_5$)$_2$, -Ph, —CH$_3$, —C$_2$H$_5$, 4. The compound of claim 1, wherein
Y is selected from the group consisting of —CH$_3$, —C$_2$H$_5$, —C$_3$H$_7$, —C$_4$H$_9$, —C$_5$H$_{11}$, —C$_2$H$_4$—CH(CH$_3$)$_2$,

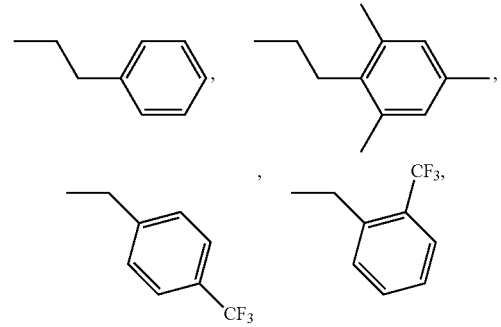

—CH(CH$_3$)—CH$_2$—CH(CH$_3$)$_2$, —CH$_2$—CH(C$_2$H$_5$)$_2$, —CH$_2$—CH(CH$_3$)—C$_2$H$_5$, —C$_2$H$_4$—C(CH$_3$)$_3$, and —C$_2$H$_4$—CH(C$_2$H$_5$)$_2$.

5. The compound of claim 1, wherein
X is —CH$_2$R$^7$, —CHR$^7$—CH$_2$R$^8$,

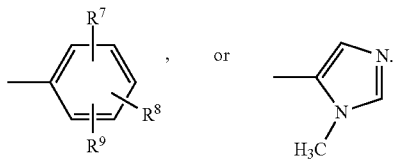

6. The compound of claim 1, wherein
Z is —OCH$_3$, —OCH$_2$CH$_3$, or —OCH$_2$-Ph;
E$^1$ is —CO— or —SO$_2$—;
E$^2$ is —CO—;
R* is —H or —CH$_3$;
R$^\#$ is selected from the group consisting of: —NYY',

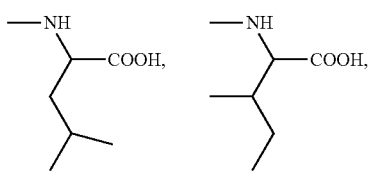

-continued

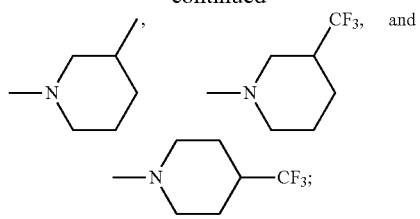

Y' is —H;

Y is selected from the group consisting of —CH$_2$R$^1$, —CHR$^1$—CH$_2$R$^2$, —CHR$^1$—CHR$^2$—CH$_2$R$^3$, —CHR$^1$—CHR$^2$—CHR$^3$—CH$_2$R$^4$, and —CHR$^1$—CHR$^2$—CHR$^3$—CHR$^4$—CH$_2$R$^5$;

R$^1$, R$^2$, R$^3$, R$^4$, and R$^5$ are each independently selected from the group consisting of:

—H, —CH$_3$, —C$_2$H$_5$, -Ph, —CH$_2$—CH(CH$_3$)$_2$, —N(CH$_3$)$_2$, —N(C$_2$H$_5$)$_2$, —COOH, —COOCH$_3$, —C(CH$_3$)$_3$,

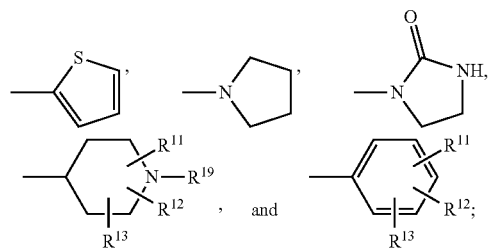

R$^{11}$, R$^{12}$, and R$^{13}$ are each independently —H, —CH$_3$, —C$_2$H$_5$, or —CF$_3$;

R$^{19}$ is —C$_2$H$_5$;

X is selected from the group consisting of —CH$_2$R$^7$, —CHR$^7$—CH$_2$R$^8$, —O—CH$_2$R$^7$,

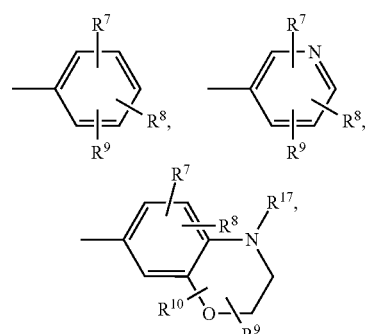

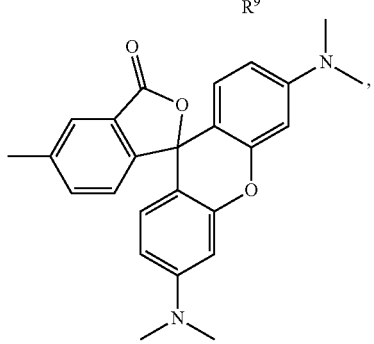

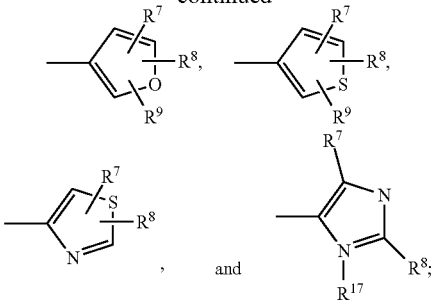

R$^7$, R$^8$, R$^9$, and R$^{10}$ are each independently selected from the group consisting of —H, —OH, —COOH, —SO$_2$NH$_2$, —CH$_3$, —CF$_3$, —NH$_2$·HOOCCF$_3$, —NH$_2$,

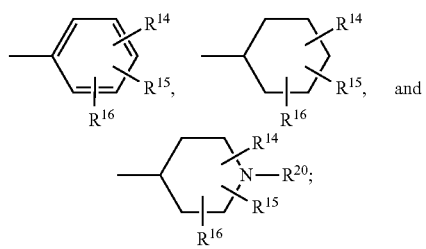

R$^{14}$, R$^{15}$, and R$^{16}$ are each independently —H, —Cl, or —CH$_3$; and R$^{17}$, R$^{18}$, R$^{19}$, and R$^{20}$ are each —CH$_3$.

7. The compound of claim 1 represented by general formula (II):

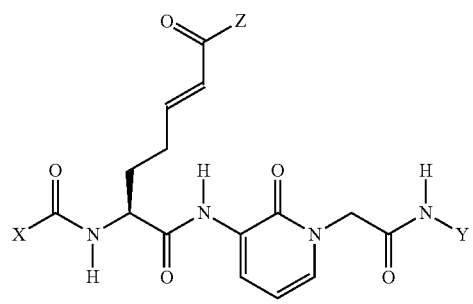

wherein X, Y and Z are as defined in claim 1.

8. The compound of claim 1 selected from the group consisting of:
(S,E)-ethyl 6-(benzyloxycarbonylamino)-7-oxo-7-(2-oxo-1-(2-oxo-2-(2,4,6-trimethylphenethylamino)ethyl)-1,2-dihydropyridin-3-ylamino)hept-2-enoate,
(S,E)-ethyl 6-(benzyloxycarbonylamino)-7-(1-(2-(isopentylamino)-2-oxoethyl)-6-methyl-2-oxo-1,2-dihydropyridin-3-ylamino)-7-oxohept-2-enoate,
(S,E)-ethyl 6-(benzyloxycarbonylamino)-7-(1-(2-(isopentylamino)-2-oxoethyl)-2-oxo-1,2-dihydropyridin-3-ylamino)-7-oxohept-2-enoate,
(S,E)-ethyl 6-acetamido-7-(1-(2-(isopentylamino)-2-oxoethyl)-6-methyl-2-oxo-1,2-dihydropyridin-3-ylamino)-7-oxohept-2-enoate, 3-(2-(3-4S,E)-2-(benzyloxycarbonylamino)-7-ethoxy-7-oxohept-5-enamido)-6-methyl-2-oxopyridin-1(2H)-yl)acetamido)-5-methylhexanoic acid, (S,E)-isopropyl 6-acetamido-7-(1-(2-(isopentylamino)-2-oxoethyl)-2-oxo-1,2-dihydropyridin-3-ylamino)-7-oxohept-2-enoate, (S,E)-ethyl 6-acetamido-7-(1-(2-(isopentylamino)-2-oxoethyl)-2-oxo-1,2-dihydropyridin-3-ylamino)-7-oxohept-2-enoate, (S,E)-ethyl 7-(6-methyl-2-oxo-1-(2-oxo-2-(phenethylamino)ethyl)-1,2-dihydropyridin-3-ylamino)-6-(nicotinamido)-7-oxohept-2-enoate, (S,E)-ethyl 6-((4-chlorophenyl)methylsulfonamido)-7-(1-(2-(isopentylamino)-2-oxoethyl)-2-oxo-1,2-dihydropyridin-3-ylamino)-7-oxohept-2-enoate, (S,E)-ethyl 6-benzamido-7-(1-(2-(isopentylamino)-2-oxoethyl)-2-oxo-1,2-dihydropyridin-3-ylamino)-7-oxohept-2-enoate, (S,E)-ethyl 6-(furan-3-carboxamido)-7-(1-(2-(isopentylamino)-2-oxoethyl)-2-oxo-1,2-dihydropyridin-3-ylamino)-7-oxohept-2-enoate, (S,E)-ethyl 7-(1-(2-(isopentylamino)-2-oxoethyl)-2-oxo-1,2-dihydropyridin-3-ylamino)-7-oxo-6-(thiophene-3-carboxamido)hept-2-enoate, (S,E)-ethyl 6-(furan-3-sulfonamido)-7-(1-(2-(isopentylamino)-2-oxoethyl)-2-oxo-1,2-dihydropyridin-3-ylamino)-7-oxohept-2-enoate, (S,E)-ethyl 7-(1-(2-(isopentylamino)-2-oxoethyl)-2-oxo-1,2-dihydropyridin-3-ylamino)-7-oxo-6-(4-sulfamoylbenzamido)hept-2-enoate, (S,E)-ethyl 7-(1-(2-(isopentylamino)-2-oxoethyl)-2-oxo-1,2-dihydropyridin-3-ylamino)-6-(5-methylthiazole-4-carboxamido)-7-oxohept-2-enoate, (S,E)-ethyl 7-(1-(2-(isopentylamino)-2-oxoethyl)-2-oxo-1,2-dihydropyridin-3-ylamino)-6-(nicotinamido)-7-oxohept-2-enoate, (S,E)-ethyl 6-(3,5-bis(trifluoromethyl)benzamido)-7-(1-(2-(isopentylamino)-2-oxoethyl)-2-oxo-1,2-dihydropyridin-3-ylamino)-7-oxohept-2-enoate, (S,E)-ethyl 7-(1-(2-(isopentylamino)-2-oxoethyl)-2-oxo-1,2-dihydropyridin-3-ylamino)-7-oxo-6-(4-(piperidin-1-yl)benzamido)hept-2-enoate, (S,E)-ethyl 7-(1-(2-(isopentylamino)-2-oxoethyl)-2-oxo-1,2-dihydropyridin-3-ylamino)-6-(1-methyl-1H-imidazole-5-carboxamido)-7-oxohept-2-enoate, (S,E)-ethyl 7-(1-(2-(isopentylamino)-2-oxoethyl)-2-oxo-1,2-dihydropyridin-3-ylamino)-6-(4-(4-methylpiperazin-1-yl)benzamido)-7-oxohept-2-enoate, (S,E)-ethyl 7-(1-(2-(isopentylamino)-2-oxoethyl)-2-oxo-1,2-dihydropyridin-3-ylamino)-6-(4-methyl-3,4-dihydro-2H-benzo[b][1,4]oxazine-7-carboxamido)-7-oxohept-2-enoate, (S,E)-ethyl 7-(1-(2-(isopentylamino)-2-oxoethyl)-2-oxo-1,2-dihydropyridin-3-ylamino)-7-oxo-6-(phenylsulfonamido)hept-2-enoate, (S,E)-5-(N-(7-ethoxy-1-(1-(2-(isopentylamino)-2-oxoethyl)-2-oxo-1,2-dihydropyridin-3-ylamino)-1,7-dioxohept-5-en-2-yl)sulfamoyl)-2-hydroxybenzoic acid, (S,E)-4-(7-ethoxy-1-(1-(2-(isopentylamino)-2-oxoethyl)-2-oxo-1,2-dihydropyridin-3-ylamino)-1,7-dioxohept-5-en-2-ylamino)-4-oxobutanoic acid, (S,E)-ethyl 6-acetamido-7-(1-(2-(2-(diethylamino)ethylamino)-2-oxoethyl)-2-oxo-1,2-dihydropyridin-3-ylamino)-7-oxohept-2-enoate, (S,E)-4-(1-(1-(2-(2-(diethylamino)ethylamino)-2-oxoethyl)-2-oxo-1,2-dihydropyridin-3-ylamino)-7-ethoxy-1, 7-dioxohept-5-en-2-ylamino)-4-oxobutanoic acid, (S,E)-ethyl 6-acetamido-7-(1-(2-(2-(dimethylamino)ethylamino)-2-oxoethyl)-2-oxo-1,2-dihydropyridin-3-ylamino)-7-oxohept-2-enoate, (S,E)-methyl 6-acetamido-7-(1-(2-(isopentylamino)-2-oxoethyl)-2-oxo-1,2-dihydropyridin-3-ylamino)-7-oxohept-2-enoate, (S,E)-methyl 6-acetamido-7-(1-(2-(isopentylamino)-2-oxoethyl)-2-oxo-1,2-dihydropyridin-3-ylamino)-7-oxohept-2-enoate, (S,E)-4-(7-ethoxy-1-(1-(2-(2-ethylbutylamino)-2-oxoethyl)-2-oxo-1,2-dihydropyridin-3-ylamino)-1,7-dioxohept-5-en-2-ylamino)-4-oxobutanoic acid, (S,E)-ethyl 6-acetamido-7-(1-(2-((S)-1-methoxy-4-methyl-1-oxopentan-2-ylamino)-2-oxoethyl)-2-oxo-1,2-dihydropyridin-3-ylamino)-7-oxohept-2-enoate, 4-((S,E)-7-ethoxy-1-(1-(2-((S)-1-methoxy-4-methyl-1-oxopentan-2-ylamino)-2-oxoethyl)-2-oxo-1,2-dihydropyridin-3-ylamino)-1,7-dioxohept-5-en-2-ylamino)-4-oxobutanoic acid, (S,E)-ethyl 6-acetamido-7-(1-(2-((R)-1-methoxy-4-methyl-1-oxopentan-2-ylamino)-2-oxoethyl)-2-oxo-1,2-dihydropyridin-3-ylamino)-7-oxohept-2-enoate, 4-((S,E)-7-ethoxy-1-(1-(2-((R)-1-methoxy-4-methyl-1-oxopentan-2-ylamino)-2-oxoethyl)-2-oxo-1,2-dihydropyridin-3-ylamino)-1,7-dioxohept-5-en-2-ylamino)-4-oxobutanoic acid, (S,E)-ethyl 6-acetamido-7-(1-(2-((2 S,3R)-1-methoxy-3-methyl-1-oxopentan-2-ylamino)-2-oxoethyl)-2-oxo-1,2-dihydropyridin-3-ylamino)-7-oxohept-2-enoate, 4-((S,E)-7-ethoxy-1-(1-(2-((2 S,3R)-1-methoxy-3-methyl-1-oxopentan-2-ylamino)-2-oxoethyl)-2-oxo-1,2-dihydropyridin-3-ylamino)-1,7-dioxohept-5-en-2-ylamino)-4-oxobutanoic acid, (S,E)-4-(7-ethoxy-1,7-dioxo-1-(2-oxo-1-(2-oxo-2-(4-(trifluoromethyl)benzylamino)ethyl)-1,2-dihydropyridin-3-ylamino)hept-5-en-2-ylamino)-4-oxobutanoic acid, (S,E)-4-(1-(1-(2-(3,3-dimethylbutylamino)-2-oxoethyl)-2-oxo-1,2-dihydropyridin-3-ylamino)-7-ethoxy-1,7-dioxohept-5-en-2-ylamino)-4-oxobutanoic acid, (S,E)-ethyl 6-acetamido-7-(1-(2-(3,3-dimethylbutylamino)-2-oxoethyl)-2-oxo-1,2-dihydropyridin-3-ylamino)-7-oxohept-2-enoate, (S,E)-ethyl 6-acetamido-7-(1-(2-((S)-1-methoxy-4,4-dimethyl-1-oxopentan-2-ylamino)-2-oxoethyl)-2-oxo-1,2-dihydropyridin-3-ylamino)-7-oxohept-2-enoate, 4-((S,E)-7-ethoxy-1-(1-(2-((S)-1-methoxy-4,4-dimethyl-1-oxopentan-2-ylamino)-2-oxoethyl)-2-oxo-1,2-dihydropyridin-3-ylamino)-1,7-dioxohept-5-en-2-ylamino)-4-oxobutanoic acid, (S,E)-ethyl 6-acetamido-7-(1-(2-(3-ethylpentylamino)-2-oxoethyl)-2-oxo-1,2-dihydropyridin-3-ylamino)-7-oxohept-2-enoate, (S,E)-4-(7-ethoxy-1-(1-(2-(3-ethylpentylamino)-2-oxoethyl)-2-oxo-1,2-dihydropyridin-3-ylamino)-1,7-dioxohept-5-en-2-ylamino)-4-oxobutanoic acid, (S,E)-4-(7-ethoxy-1,7-dioxo-1-(2-oxo-1-(2-oxo-2-(2-(trifluoromethyl)benzylamino)ethyl)-1,2-dihydropyridin-3-ylamino)hept-5-en-2-ylamino)-4-oxobutanoic acid, (S,E)-4-(7-ethoxy-1,7-dioxo-1-(2-oxo-1-(2-oxo-2-(4-(trifluoromethyl)piperidine-1-yl)ethyl)-1,2-dihydropyridin-3-ylamino)hept-5-en-2-ylamino)-4-oxobutanoic acid, (S,E)-ethyl 6-acetamido-7-oxo-7-(2-oxo-1-(2-oxo-2-(2-(pyrrolidine-1-yl)ethylamino)ethyl)-1,2-dihydropyridin-3-ylamino)hept-2-enoate, (S,E)-4-(7-ethoxy-1,7-dioxo-1-(2-oxo-1-(2-oxo-2-(2-(thiophen-2-yl)ethylamino)ethyl)-1,2-dihydropyridin-3-ylamino)hept-5-en-2-ylamino)-4-oxobutanoic acid,
(S,E)-ethyl 6-acetamido-7-(1-(2-((1-ethylpiperidin-4-yl)methylamino)-2-oxoethyl)-2-oxo-1,2-dihydropyridin-3-ylamino)-7-oxohept-2-enoate,
(S,E)-4-(7-ethoxy-1,7-dioxo-1-(2-oxo-1-(2-oxo-2-(2-(2-oxoimidazolidin-1-yl)ethylamino)ethyl)-1,2-dihydropyridin-3-ylamino)hept-5-en-2-ylamino)-4-oxobutanoic acid,
(6 S,E)-ethyl 6-acetamido-7-(1-(2-(2-methylbutylamino)-2-oxoethyl)-2-oxo-1,2-dihydropyridin-3-ylamino)-7-oxohept-2-enoate,
4-((2S,E)-7-ethoxy-1-(1-(2-(2-methylbutylamino)-2-oxoethyl)-2-oxo-1,2-dihydropyridin-3-ylamino)-1,7-dioxohept-5-en-2-ylamino)-4-oxobutanoic acid,
(6 S,E)-ethyl 6-acetamido-7-(1-(2-(3-methylpiperidin-1-yl)-2-oxoethyl)-2-oxo-1,2-dihydropyridin-3-ylamino)-7-oxohept-2-enoate,
(2 S,3R)-2-(2-(3-((S,E)-7-ethoxy-2-(1-methyl-1H-imidazole-5-carboxamido)-7-oxohept-5-enamido)-2-oxopyridin-1(2H)-yl)acetamido)-3-methylpentanoic acid,
(S,E)-ethyl 6-acetamido-7-(1-(2-(isobutylamino)-2-oxoethyl)-2-oxo-1,2-dihydropyridin-3-ylamino)-7-oxohept-2-enoate,
(6 S,E)-ethyl 6-acetamido-7-(1-(2-(3-methylbutan-2-ylamino)-2-oxoethyl)-2-oxo-1,2-dihydropyridin-3-ylamino)-7-oxohept-2-enoate,
(S,E)-ethyl 7-(1-(2-(isopentylamino)-2-oxoethyl)-2-oxo-1,2-dihydropyridin-3-ylamino)-7-oxo-6-(3-ureidopropanamido)hept-2-enoate,
(S,E)-ethyl 6-acetamido-7-(1-(2-((S)-1-methoxy-3-methyl-1-oxobutan-2-ylamino)-2-oxoethyl)-2-oxo-1,2-dihydropyridin-3-ylamino)-7-oxohept-2-enoate,
(S,E)-ethyl 7-(1-(2-(2-ethylbutylamino)-2-oxoethyl)-2-oxo-1,2-dihydropyridin-3-ylamino)-6-(1-methyl-1H-imidazole-5-carboxamido)-7-oxohept-2-enoate,
(2 S, 3R)-2-(2-(3-((S,E)-2-benzamido-7-ethoxy-7-oxohept-5-enamido)-2-oxopyridin-1 (2H)-yl)acetamido)-3-methylpentanoic acid,
(2 S, 3R)-2-(2-(3-((S,E)-7-methoxy-2-(1-methyl-1H-imidazole-5-carboxamido)-7-oxohept-5-enamido)-2-oxopyridin-1(2H)-yl)acetamido)-3-methylpentanoic acid,
(2 S, 3R)-2-(2-(3-((S,E)-2-benzamido-7-methoxy-7-oxohept-5-enamido)-2-oxopyridin-1 (2H)-yl)acetamido)-3-methylpentanoic acid,
(S,E)-ethyl 6-acetamido-7-(1-(2-(2-ethylbutylamino)-2-oxoethyl)-2-oxo-1,2-dihydropyridin-3-ylamino)-7-oxohept-2-enoate,
(S,E)-methyl 7-(1-(2-(2-ethylbutylamino)-2-oxoethyl)-2-oxo-1,2-dihydropyridin-3-ylamino)-6-(1-methyl-1H-imidazole-5-carboxamido)-7-oxohept-2-enoate,
(6 S,E)-methyl 6-acetamido-7-(1-(2-(3-methylpiperidin-1-yl)-2-oxoethyl)-2-oxo-1,2-dihydropyridin-3-ylamino)-7-oxohept-2-enoate,
(S,E)-methyl 6-acetamido-7-oxo-7-(2-oxo-1-(2-oxo-2-(4-(trifluoromethyl)piperidin-1-yl)ethyl)-1,2-dihydropyridin-3-ylamino)hept-2-enoate,
(6 S,E)-methyl 6-acetamido-7-oxo-7-(2-oxo-1-(2-oxo-2-(3-(trifluoromethyl)piperidin-1-yl)ethyl)-1,2-dihydropyridin-3-ylamino)hept-2-enoate,
(S,E)-methyl 7-(1-(2-(2-ethylbutylamino)-2-oxoethyl)-2-oxo-1,2-dihydropyridin-3-ylamino)-6-(nicotinamido)-7-oxohept-2-enoate,
(6 S,E)-methyl 6-(2-aminopropanamido)-7-(1-(2-(2-ethylbutylamino)-2-oxoethyl)-2-oxo-1,2-dihydropyridin-3-ylamino)-7-oxohept-2-enoate 2,2,2-trifluoroacetate,
(S,E)-Methyl 6-(2-aminoacetamido)-7-1-(2-(2-ethlbutylamino)-2-oxoethyl)-2-oxo-1,2-dihydropyridin-3-ylamino)-7-oxohept-2-enoate 2,2,2-trifluoroacetate,
(S,E)-methyl 6-(2-aminobenzamido)-7-(1-(2-(2-ethylbutylamino)-2-oxoethyl)-2-oxo-1,2-dihydropyridin-3-ylamino)-7-oxohept-2-enoate 2,2,2-trifluoroacetate,
(S,E)-methyl 6-(3',6'-bis(dimethylamino)-3-oxo-3H-spiro[isobenzofuran-1,9'-xanthene]-5-ylcarboxamido)-7-(1-(2-(2-ethylbutylamino)-2-oxoethyl)-2-oxo-1,2-dihydropyridin-3-ylamino)-7-oxohept-2-enoate,
(S,E)-ethyl 6-acetamido-7-(1-(2-(isopentylamino)-2-oxoethyl)-2-oxo-1,2-dihydropyridin-3-ylamino)-7-oxohept-2-enoate,
(S,E)-methyl 6-acetamido-7-(1-(2-(isopentylamino)-2-oxoethyl)-2-oxo-1,2-dihydropyridin-3-ylamino)-7-oxohept-2-enoate,
(S,E)-ethyl 7-(1-(2-(2-ethylbutylamino)-2-oxoethyl)-2-oxo-1,2-dihydropyridin-3-ylamino)-6-(1-methyl-1H-imidazole-5-carboxamido)-7-oxohept-2-enoate,
(2 S,3R)-2-(2-(3-((S,E)-2-benzamido-7-methoxy-7-oxohept-5-enamido)-2-oxopyridin-1 (2H)-yl)acetamido)-3-methylpentanoic acid,
(R,E)-methyl 7-(1-(2-(2-ethylbutylamino)-2-oxoethyl)-2-oxo-1,2-dihydropyridin-3-ylamino)-6-(1-methyl-1H-imidazole-5-carboxamido)-7-oxohept-2-enoate,
(S,E)-2-acetamido-N-(1-(2-(isopentylamino)-2-oxoethyl)-2-oxo-1,2-dihydropyridin-3-yl)-6-(methylsulfonyl)hex-5-enamide,
(S,E)-benzyl 6-acetamido-7-(1-(2-(isopentylamino)-2-oxoethyl)-2-oxo-1,2-dihydropyridin-3-ylamino)-7-oxohept-2-enoate, and
(S,E)-methyl 6-acetamido-7-(1-(2-(2-ethylbutylamino)-2-oxoethyl)-2-oxo-1,2-dihydropyridin-3-ylamino)-7-oxohept-2-enoate.

9. A method of inhibiting transglutaminase 2 comprising contacting the transglutaminase 2 with the compound of claim 1.

10. A method for the treatment of coeliac disease comprising administering the compound of claim 1 to a subject.

11. A pharmaceutical composition comprising at least one compound of claim 1 and at least one pharmacologically acceptable carrier, excipient, or solvent thereof.

12. The pharmaceutical composition according to claim 11, further comprising an active agent selected from the group consisting of vitamins, inflammation inhibitors, peptidases, proteases, monoclonal antibodies immune modulators, and tight junctions modulators.

13. A method for preparing the compound of claim 1 according to the following synthesis scheme:

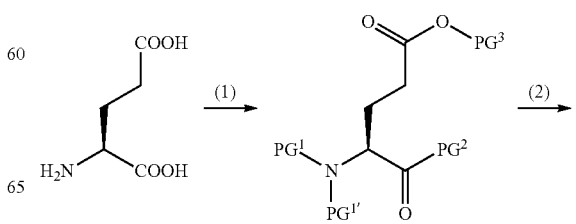

-continued

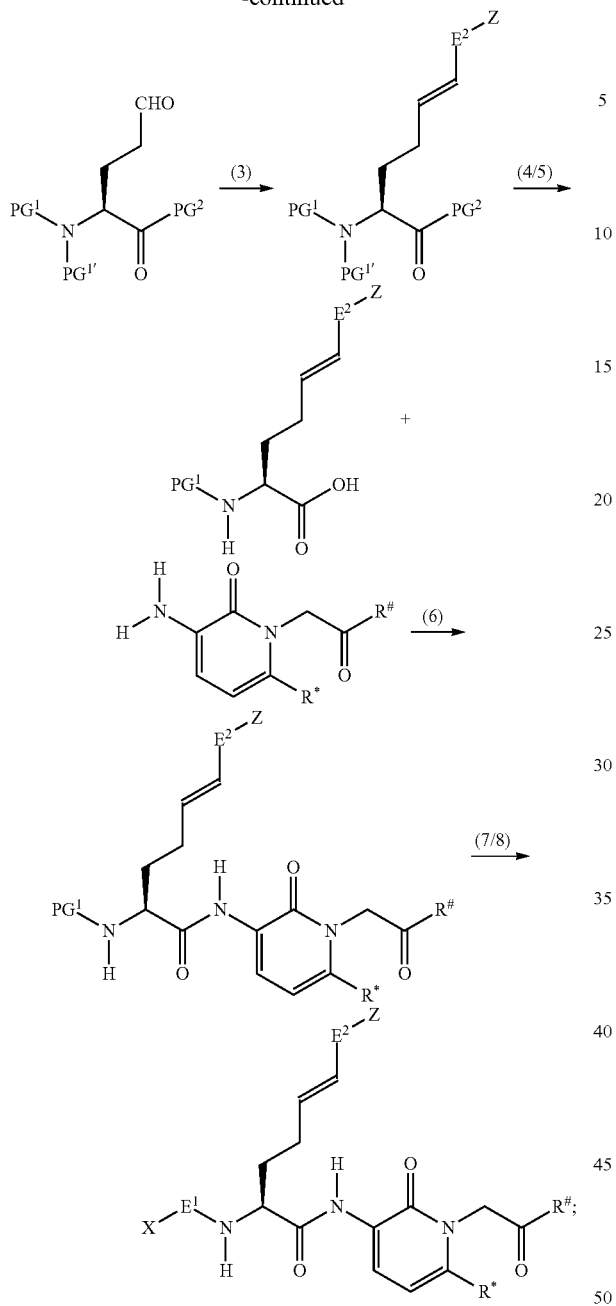

wherein the method comprises:
(0) providing a glutamic acid having a C-terminal end, an N-terminal end, and a side chain;
(1) attaching PG² at the C-terminal end, attaching PG¹ and PG¹' at the N-terminal end, and attaching PG³ at a carboxylic function of the side chain, wherein PG¹, PG¹', PG², and PG³ are each a protecting group;
(2) reducing the carboxylic function of the side chain to an aldehyde;
(3) converting the resulting aldehyde to an acceptor-substituted electrophilic double bond;
(4) removing PG¹' at the N-terminal end;
(5) removing PG² at the C-terminal end;
(6) extending the C-terminal end with a pyridinone fragment;
(7) removing the PG¹ at the N-terminal end; and
(8) extending the N-terminal end;
or

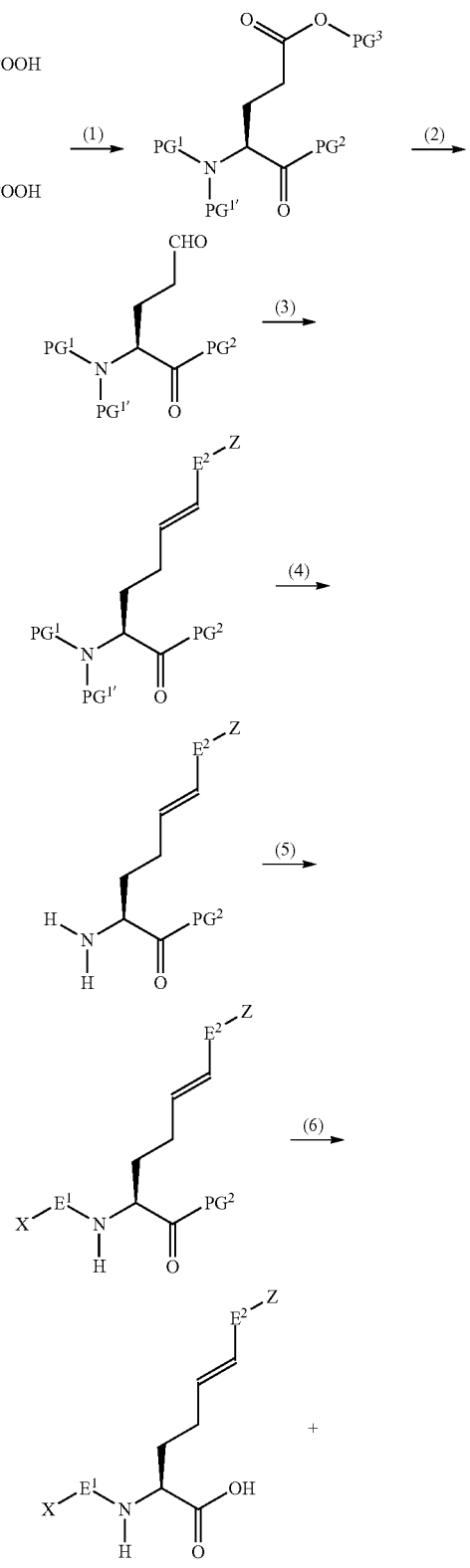

-continued

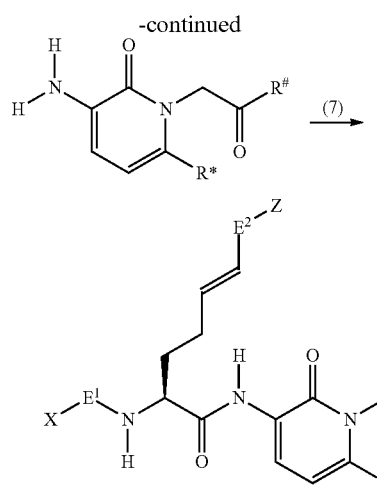

wherein the steps comprises:
(0) providing a glutamic acid acid having a C-terminal end, an N-terminal end, and a side chain;
(1) attaching $PG^2$ at the C-terminal end, attaching $PG^1$ and $PG^{1'}$ at the N-terminal end, and attaching $PG^2$ at a carboxylic function of the site chain;
(2) reducing the carboxylic function of the side chain to an aldehyde;
(3) converting the resulting aldehyde to an acceptor-substituted electrophilic double bond;
(4) removing $PG^1$ and $PG^{1'}$ at the N-terminal end;
(5) extending the N-terminal end;
(6) removing $PG^2$ at the C-terminal end;
(7) extending the C-terminal end with a pyridinone fragment; and
wherein X, Z, $E^1$, $E^2$, $R^\#$ and R* are as defined in claim 1.

* * * * *

UNITED STATES PATENT AND TRADEMARK OFFICE
CERTIFICATE OF CORRECTION

PATENT NO.        : 9,434,763 B2                                   Page 1 of 4
APPLICATION NO.   : 14/415374
DATED             : September 6, 2016
INVENTOR(S)       : Christian Buchold It is certified that error appears in the above-identified patent and that said Letters Patent is hereby corrected as shown below:

In the Specification

Column 7 Line 57, Change "—$OCH_2$—CH=CH," to -- —$OCH_2$—CH=CH;--.

Column 8 Line 48, After "—$C_7H_{15}$" insert -- —$C_8H_{17}$--.

Column 13 Line 12, Change "—ON;" to -- —CN;--.

Column 15 Lines 41-42 (approx.), Change "$CHR^1CHR^2CHR^3CHR^4CH_2R^5$ and $CHR^1CHR^2CHR^3CHR^4CHR^5CH_2R^6$," to -- —$CHR^1$—$CHR^2$—$CHR^3$—$CHR^4$—$CH_2R^5$ and —$CHR^1$—$CHR^2$—$CHR^3$—$CHR^4$—$CHR^5$—$CH_2R^6$,--.

Column 15 Line 45, Change "$CHR^1CHR^2CHR^3CHR^4CH_2R^5$," to
-- —$CHR^1$—$CHR^2$—$CHR^3$—$CHR^4$—$CH_2R^5$,--.

Column 16 Line 14, Change "$CHR^1CHR^2CHR^3CH_2R^4$," to -- —$CHR^1$—$CHR^2$—$CHR^3$—$CH_2R^4$,--.

Column 16 Line 15, Change "$CHR^1CHR^2CHR^3CHR^4CH_2R^5$," to
-- —$CHR^1$—$CHR^2$—$CHR^3$—$CHR^4$—$CH_2R^5$,--.

Column 16 Lines 35-40 (approx.), Change " 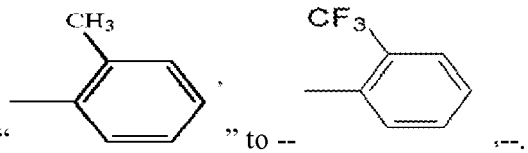 " to -- ,--.

Column 19 Lines 3-4, Change "$CHR^1CHR^2CHR^3CH_2R^4$ or $CHR^1CHR^2CHR^3CHR^4CH_2R^9$;" to
-- —$CHR^1$—$CHR^2$—$CHR^3$—$CH_2R^4$ or —$CHR^1$—$CHR^2$—$CHR^3$—$CHR^4$—$CH_2R^5$;--.

Column 24 Line 46, Change "(5,E)" to --(S,E)--.

Signed and Sealed this
Nineteenth Day of December, 2017

Joseph Matal
*Performing the Functions and Duties of the
Under Secretary of Commerce for Intellectual Property and
Director of the United States Patent and Trademark Office*

CERTIFICATE OF CORRECTION (continued)

Column 25 Line 62, Change "(6S, E)-ethyl" to --(6S,E)-ethyl--.

Column 26 Line 4, Change "(6S, E)-ethyl" to --(6S,E)-ethyl--.

Column 26 Line 30, Change "A63" to --(A63)--.

Column 26 Line 31, Change "(6S, E)-methyl" to --(6S,E)-methyl--.

Column 26 Line 37, Change "(6S, E)-methyl" to --(6S,E)-methyl--.

Column 26 Line 43, Change "(6S, E)-methyl" to --(6S,E)-methyl--.

Column 27 Line 4, Change "(5,E)" to --(S,E)--.

Column 29 Line 20, Change "site" to --side--.

Column 36 Line 64, Change "Julia-Lytgoe" to --Julia-Lythgoe--.

Column 37 Line 8, Change "Sigam-Aldrich)" to --Sigma-Aldrich)--.

Column 37 Line 25, Change "derivates." to --derivatives.--.

Column 38 Line 21, Change "387.47" to --317.38--.

Column 39 Line 55 (approx.), Change "codestillation" to --codistillation--.

Column 42 Line 14, Change "358.59" to --358.39--.

Column 42 Line 61, Change "trifloroacetic" to --trifluoroacetic--.

Column 46 Lines 15-17, Delete "$Na_2SO_4$ and concentrated in vacuo in dryness. The residue is purified by chromatography on silica gel (bed: 13×6 cm, eluent: toluene/acetone=7/3)." and insert the same on Column 46, Line 14, as a continuation of the same paragraph.

Column 46 Line 27 (approx.), Change "A63" to --(A63)--.

Column 51 Lines 49-58 (approx.), Delete "137 mg (0.23 mmol) of the obtained oil are dissolved in 2.5 ml of DMF. To this 15 solution a solution of 87 mg of HATU (0.23 mmol), 23 mg of benzoic acid (0.23 mmol) and 78 μL of DIPEA (2 eq) in 2 ml of DMF is added. By successive addition of DIPEA the pH value is adjusted to ca. 7. It is stirred overnight at RT, before the solvent is removed in vacuo. The residue is purified by preparative HPLC (30% ACN in water, 8 mL/min, gradient 1% pro min)." and insert the same on Column 51, Line 50, as a new paragraph.

Column 69 at Line 22 (approx.), Change "C23H46N6O6" to --C33H46N6O6--.

Column 84 at Line 64 (approx.), Change "C30H38N5O8" to --C30H38F3N5O8--.

CERTIFICATE OF CORRECTION (continued)

Column 88 Line 11, Change "al," to --al.--.

In the Claims

Column 92 Line 26, Claim 1, Change "NYY'," to -- —NYY',--.

Column 92 Lines 37-38, Claim 1, Change "—NH—CH(CH$_2$CH$_2$SCH$_3$)—COOP'," to -- —NH—CH(CH$_2$CH$_2$SCH$_3$)—COOY',--.

Column 98 Lines 31-32, Claim 1, Change "—NH—C S—Nh$_2$, —NH—C S—NhCH$_3$, —NH—C S—NhC$_2$H$_5$, —NH—C S—NhC$_3$H$_7$," to -- —NH—CS—NH$_2$, —NH—CS—NHCH$_3$, —NH—CS—NHC$_2$H$_5$, —NH—CS—NHC$_3$H$_7$--.

Column 98 Lines 33-34, Claim 1, Change "—NH—C S—Nh[CH(CH$_3$)$_2$], —NH—C S—Nh[C(CH$_3$)$_3$]," to -- —NH—CS—NH[CH(CH$_3$)$_2$], —NH—CS—NH[C(CH$_3$)$_3$],--.

Column 98 Lines 62-63, Claim 1, Change "CH=CH—C$_3$H$_7$, CH$_2$CH=CH—CH=CH$_2$, CH=CH CH=CH—CH$_3$, CH$_2$NH$_2$," to -- —CH=CH—C$_3$H$_7$, —CH$_2$CH=CH—CH=CH$_2$, —CH=CH—CH=CH—CH$_3$, —CH$_2$NH$_2$,--.

Column 103 Line 66, Claim 3, after "—C$_2$H$_5$," insert -- —CH$_2$—CH(CH$_3$)$_2$, —C(CH$_3$)$_3$,— --.

Column 106 Line 17, Claim 6, after "—CF$_3$" insert -- —NH—CO—NH$_2$--.

Column 106 Lines 20-25, Claim 6, Change " 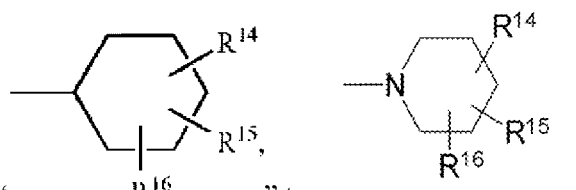 " to -- ,--.

Column 107 Line 1, Claim 8, Change "3-(2-(3-4S,E)" to --3-(2-(3-((S,E)"--.

Column 108 Line 28, Claim 8, Change "((2 S,3R)" to --((2S,3R)--.

Column 108 Line 32, Claim 8, Change "((2 S,3R)" to --((2S,3R)--.

Column 109 Line 11, Claim 8, Change "(6 S,E)-ethyl" to --(6S,E)-ethyl--.

Column 109 Line 17, Claim 8, Change "(6 S,E)-ethyl" to --(6S,E)-ethyl--.

Column 109 Line 20, Claim 8, Change "(2 S,3R)" to --(2S,3R)--.

Column 109 Line 26, Claim 8, Change "(6 S,E)-ethyl" to --(6S,E)-ethyl--.

Column 109 Line 38, Claim 8, Change "((2 S, 3R)" to --((2S,3R)--.

CERTIFICATE OF CORRECTION (continued)
U.S. Pat. No. 9,434,763 B2

Column 109 Line 39, Claim 8, Change "1 (2H)" to --1(2H)--.

Column 109 Line 41, Claim 8, Change "((2 S, 3R)" to --((2S,3R)--.

Column 109 Line 44, Claim 8, Change "((2 S, 3R)" to --((2S,3R)--.

Column 109 Line 45, Claim 8, Change "1 (2H)" to --1(2H)--.

Column 109 Line 45, Claim 8, Change "1 (2H)" to --1(2H)--.

Column 109 Line 53, Claim 8, Change "(6 S,E)-methyl" to --(6S,E)-methyl--.

Column 109 Line 59, Claim 8, Change "(6 S,E)-methyl" to --(6S,E)-methyl--.

Column 109 Line 65, Claim 8, Change "(6 S,E)-methyl" to --(6S,E)-methyl--.

Column 110 Line 1, Claim 8, Change "(S,E)-Methyl" to --(S,E)-methyl--.

Column 110 Line 1, Claim 8, Change "(2-ethlbuty-" to --(2-ethylbutyl- --.

Column 110 Line 23, Claim 8, Change "((2 S,3R)" to --((2S,3R)--.

Column 110 Line 24, Claim 8, Change "1 (2H)" to --1(2H)--.

Column 114 Line 2, Claim 13, Change "acid acid" to --acid--.

Column 114 Line 6, Claim 13, Change "site" to --side--.